US009308016B2

(12) United States Patent
Escudero et al.

(10) Patent No.: US 9,308,016 B2
(45) Date of Patent: *Apr. 12, 2016

(54) DEVICES, SYSTEMS, AND METHODS FOR PERFORMING ATHERECTOMY INCLUDING DELIVERY OF A BIOACTIVE MATERIAL

(71) Applicant: AtheroMed, Inc., Menlo Park, CA (US)

(72) Inventors: Paul Quentin Escudero, Redwood City, CA (US); John To, Newark, CA (US); Christopher James Danek, San Carlos, CA (US); Uriel Hiran Chee, Santa Cruz, CA (US); August Christopher Pombo, Redwood City, CA (US); Torrey Smith, Redwood City, CA (US); Brenda Hann, Menlo Park, CA (US)

(73) Assignee: AtheroMed, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,870

(22) Filed: Dec. 14, 2012

(65) Prior Publication Data

US 2013/0103063 A1    Apr. 25, 2013

Related U.S. Application Data

(60) Continuation of application No. 12/932,371, filed on Feb. 24, 2011, now abandoned, which is a division of application No. 12/215,752, filed on Jun. 30, 2008, now abandoned, and a continuation-in-part of (Continued)

(51) Int. Cl.
*A61B 17/3207* (2006.01)
*A61B 17/00* (2006.01)

(Continued)

(52) U.S. Cl.
CPC ..... *A61B 17/3207* (2013.01); *A61B 17/320758* (2013.01); *A61B 2017/003* (2013.01);

(Continued)

(58) Field of Classification Search
CPC ............... A61B 17/3207; A61B 17/320758; A61B 2017/320766; A61B 2017/320775; A61B 17/32002; A61B 2017/32004; A61B 2017/320024; A61M 25/0051; A61M 25/0054; A61M 25/0138
USPC .......................................... 606/159, 170, 180
See application file for complete search history.

(56) References Cited

U.S. PATENT DOCUMENTS

| 3,358,472 A | 12/1967 | Klipping |
| 4,167,944 A | 9/1979 | Banko |

(Continued)

FOREIGN PATENT DOCUMENTS

| EP | 0 254 414 A1 | 1/1988 |
| EP | 0 817 594 B1 | 6/2002 |

(Continued)

OTHER PUBLICATIONS

Ex-Parte Quayle Action mailed on Mar. 30, 2012, for U.S. Appl. No. 11/567,715, filed Dec. 6, 2006, 6 pages.

(Continued)

*Primary Examiner* — Sarah W Aleman
(74) *Attorney, Agent, or Firm* — Thomas C. Meyers; Brown Rudnick LLP

(57) ABSTRACT

Devices, systems, and methods are employed to perform an atherectomy in an identified region to restore patency to arterial lesions. A bioactive material is introduced into the identified region before, after or during performing the atherectomy. The bioactive material can be introduced, e.g., on a balloon coated with the bioactive material, which is expanded in contact with the identified region to deliver the bioactive material. The bioactive material can be, e.g., at least one of a restenosis-inhibiting agent, a thrombus-inhibiting agent, and an anti-inflammatory agent.

6 Claims, 42 Drawing Sheets

Related U.S. Application Data application No. 11/771,865, filed on Jun. 29, 2007, now abandoned, which is a continuation-in-part of application No. 11/567,715, filed on Dec. 6, 2006, now Pat. No. 8,361,094, which is a continuation of application No. 11/551,191, filed on Oct. 19, 2006, now Pat. No. 8,920,448.

(60) Provisional application No. 60/981,735, filed on Oct. 22, 2007, provisional application No. 61/043,998, filed on Apr. 10, 2008, provisional application No. 60/806,417, filed on Jun. 30, 2006, provisional application No. 60/820,475, filed on Jul. 26, 2006.

(51) Int. Cl.
*A61B 17/22* (2006.01)
*A61B 17/29* (2006.01)
*A61B 17/32* (2006.01)

(52) U.S. Cl.
CPC ............... *A61B2017/00309* (2013.01); *A61B 2017/00685* (2013.01); *A61B 2017/22039* (2013.01); *A61B 2017/22044* (2013.01); *A61B 2017/22068* (2013.01); *A61B 2017/22094* (2013.01); *A61B 2017/2929* (2013.01); *A61B 2017/320032* (2013.01); *A61B 2017/320775* (2013.01)

(56) References Cited

U.S. PATENT DOCUMENTS

| | | | |
|---|---|---|---|
| 4,445,509 A | 5/1984 | Auth | |
| 4,598,710 A | 7/1986 | Kleinberg et al. | |
| 4,631,052 A | 12/1986 | Kensey | |
| 4,669,469 A | 6/1987 | Gifford, III et al. | |
| 4,690,140 A | 9/1987 | Mecca | |
| 4,696,667 A | 9/1987 | Masch | |
| 4,770,652 A | 9/1988 | Mahurkar | |
| 4,781,186 A | 11/1988 | Simpson et al. | |
| 4,790,812 A | 12/1988 | Hawkins, Jr. et al. | |
| 4,804,364 A | 2/1989 | Dieras et al. | |
| 4,808,153 A | 2/1989 | Parisi | |
| 4,844,064 A | 7/1989 | Thimsen et al. | |
| 4,857,045 A | 8/1989 | Rydell | |
| 4,857,046 A | 8/1989 | Stevens et al. | |
| 4,886,490 A | 12/1989 | Shiber | |
| 4,887,599 A | 12/1989 | Muller | |
| 4,894,051 A | 1/1990 | Shiber | |
| 4,911,148 A | 3/1990 | Sosnowski et al. | |
| 4,950,277 A | 8/1990 | Farr | |
| 4,994,067 A | 2/1991 | Summers | |
| 5,074,841 A | 12/1991 | Ademovic et al. | |
| 5,100,426 A | 3/1992 | Nixon | |
| 5,114,399 A * | 5/1992 | Kovalcheck | 604/22 |
| 5,231,989 A | 8/1993 | Middleman et al. | |
| 5,242,461 A | 9/1993 | Kortenbach et al. | |
| 5,267,955 A | 12/1993 | Hanson | |
| 5,282,813 A | 2/1994 | Redha | |
| 5,282,821 A | 2/1994 | Donahue | |
| 5,312,427 A | 5/1994 | Shturman | |
| 5,314,438 A | 5/1994 | Shturman | |
| 5,320,635 A | 6/1994 | Smith | |
| 5,334,211 A * | 8/1994 | Shiber | 606/159 |
| 5,356,418 A | 10/1994 | Shturman | |
| 5,358,472 A | 10/1994 | Vance et al. | |
| 5,360,432 A | 11/1994 | Shturman | |
| 5,370,609 A | 12/1994 | Drasler et al. | |
| 5,372,587 A | 12/1994 | Hammerslag et al. | |
| 5,409,454 A | 4/1995 | Fischell et al. | |
| 5,423,799 A | 6/1995 | Shiu | |
| 5,429,604 A | 7/1995 | Hammersmark et al. | |
| 5,429,617 A | 7/1995 | Hammersmark et al. | |
| 5,431,173 A | 7/1995 | Chin et al. | |
| 5,456,680 A | 10/1995 | Taylor et al. | |
| 5,474,532 A | 12/1995 | Steppe | |
| 5,489,291 A | 2/1996 | Wiley | |
| 5,501,653 A | 3/1996 | Chin | |
| 5,520,609 A | 5/1996 | Moll et al. | |
| 5,529,580 A | 6/1996 | Kusunoki et al. | |
| 5,540,706 A | 7/1996 | Aust et al. | |
| 5,554,163 A | 9/1996 | Shturman | |
| 5,556,408 A | 9/1996 | Farhat | |
| 5,569,197 A | 10/1996 | Helmus et al. | |
| 5,569,275 A * | 10/1996 | Kotula et al. | 606/159 |
| 5,584,843 A | 12/1996 | Wulfman et al. | |
| 5,618,294 A | 4/1997 | Aust et al. | |
| 5,626,562 A | 5/1997 | Castro | |
| 5,632,755 A | 5/1997 | Nordgren et al. | |
| 5,634,883 A | 6/1997 | Chin et al. | |
| 5,643,178 A | 7/1997 | Moll et al. | |
| 5,643,251 A | 7/1997 | Hillsman et al. | |
| 5,643,297 A | 7/1997 | Nordgren et al. | |
| 5,643,298 A | 7/1997 | Nordgren et al. | |
| 5,649,941 A | 7/1997 | Lary | |
| 5,665,062 A | 9/1997 | Houser | |
| 5,665,098 A | 9/1997 | Kelly et al. | |
| 5,669,926 A | 9/1997 | Aust et al. | |
| 5,690,634 A | 11/1997 | Muller et al. | |
| 5,690,643 A | 11/1997 | Wijay | |
| 5,695,506 A | 12/1997 | Pike et al. | |
| 5,716,327 A | 2/1998 | Warner et al. | |
| 5,725,543 A | 3/1998 | Redha | |
| 5,728,129 A | 3/1998 | Summers | |
| 5,733,297 A | 3/1998 | Wang | |
| 5,743,456 A | 4/1998 | Jones et al. | |
| 5,746,758 A | 5/1998 | Nordgren et al. | |
| 5,755,731 A | 5/1998 | Grinberg | |
| 5,766,196 A | 6/1998 | Griffiths | |
| 5,779,721 A | 7/1998 | Nash | |
| 5,782,834 A | 7/1998 | Lucey et al. | |
| 5,820,592 A | 10/1998 | Hammerslag | |
| 5,843,103 A | 12/1998 | Wulfman | |
| 5,851,208 A | 12/1998 | Trolt | |
| 5,851,212 A | 12/1998 | Zirps et al. | |
| 5,873,882 A | 2/1999 | Straub et al. | |
| 5,876,414 A | 3/1999 | Straub | |
| 5,882,329 A | 3/1999 | Patterson et al. | |
| 5,882,333 A | 3/1999 | Schaer et al. | |
| 5,895,399 A | 4/1999 | Barbut et al. | |
| 5,897,566 A | 4/1999 | Shturman et al. | |
| 5,902,263 A | 5/1999 | Patterson et al. | |
| 5,902,313 A | 5/1999 | Redha | |
| 5,941,869 A | 8/1999 | Patterson et al. | |
| 5,941,893 A | 8/1999 | Saadat | |
| 6,001,112 A | 12/1999 | Taylor | |
| 6,015,420 A | 1/2000 | Wulfman et al. | |
| 6,027,514 A | 2/2000 | Stine et al. | |
| 6,042,593 A | 3/2000 | Storz et al. | |
| 6,053,923 A | 4/2000 | Veca et al. | |
| 6,066,153 A | 5/2000 | Lev | |
| 6,080,170 A | 6/2000 | Nash et al. | |
| 6,090,118 A | 7/2000 | McGuckin, Jr. | |
| 6,132,444 A | 10/2000 | Shturman et al. | |
| 6,139,557 A | 10/2000 | Passafaro et al. | |
| 6,142,955 A | 11/2000 | Farascioni et al. | |
| 6,146,395 A | 11/2000 | Kanz et al. | |
| 6,152,938 A | 11/2000 | Curry | |
| 6,156,046 A * | 12/2000 | Passafaro et al. | 606/159 |
| 6,165,209 A | 12/2000 | Patterson et al. | |
| 6,183,487 B1 * | 2/2001 | Barry et al. | 606/159 |
| 6,206,898 B1 | 3/2001 | Honeycutt et al. | |
| 6,238,405 B1 | 5/2001 | Findlay, III et al. | |
| 6,241,744 B1 | 6/2001 | Imran et al. | |
| 6,258,098 B1 | 7/2001 | Taylor et al. | |
| 6,264,630 B1 | 7/2001 | Mickley et al. | |
| 6,299,622 B1 | 10/2001 | Snow et al. | |
| 6,319,242 B1 | 11/2001 | Patterson et al. | |
| 6,355,027 B1 | 3/2002 | Le et al. | |
| 6,371,928 B1 | 4/2002 | McFann et al. | |
| 6,406,442 B1 | 6/2002 | McFann et al. | |
| 6,451,036 B1 | 9/2002 | Heitzmann et al. | |
| 6,454,779 B1 | 9/2002 | Taylor | |

(56) References Cited

U.S. PATENT DOCUMENTS

| | | |
|---|---|---|
| 6,482,215 B1 | 11/2002 | Shiber |
| 6,482,217 B1 | 11/2002 | Pintor et al. |
| 6,494,890 B1 | 12/2002 | Shturman et al. |
| 6,497,711 B1 | 12/2002 | Plaia et al. |
| 6,554,846 B2 | 4/2003 | Hamilton et al. |
| 6,562,049 B1 | 5/2003 | Norlander et al. |
| 6,565,588 B1 | 5/2003 | Clement et al. |
| 6,572,630 B1 | 6/2003 | McGuckin, Jr. et al. |
| 6,579,298 B1 | 6/2003 | Bruneau et al. |
| 6,579,299 B2 | 6/2003 | McGuckin, Jr. et al. |
| 6,596,005 B1 | 7/2003 | Drummond et al. |
| 6,602,264 B1 | 8/2003 | McGuckin, Jr. |
| 6,623,495 B2 | 9/2003 | Findlay, III et al. |
| 6,629,953 B1 | 10/2003 | Boyd |
| 6,638,233 B2 | 10/2003 | Corvi et al. |
| 6,638,288 B1 | 10/2003 | Shturman et al. |
| RE38,335 E | 11/2003 | Aust et al. |
| 6,656,195 B2 | 12/2003 | Peters et al. |
| 6,666,854 B1 | 12/2003 | Lange |
| 6,666,874 B2 | 12/2003 | Heitzmann et al. |
| 6,682,545 B1 | 1/2004 | Kester |
| 6,702,830 B1 | 3/2004 | Demarais et al. |
| 6,746,422 B1 | 6/2004 | Noriega et al. |
| 6,758,851 B2 | 7/2004 | Shiber |
| 6,790,215 B2 | 9/2004 | Findlay, III et al. |
| 6,800,085 B2 | 10/2004 | Selmon et al. |
| 6,808,531 B2 | 10/2004 | Lafontaine et al. |
| 6,818,001 B2 | 11/2004 | Wulfman et al. |
| 6,818,002 B2 | 11/2004 | Shiber |
| 6,830,577 B2 | 12/2004 | Nash et al. |
| 6,843,797 B2 | 1/2005 | Nash et al. |
| 6,860,235 B2 | 3/2005 | Anderson et al. |
| 6,876,414 B2 | 4/2005 | Hara et al. |
| 6,936,056 B2 | 8/2005 | Nash et al. |
| 6,997,934 B2 | 2/2006 | Snow et al. |
| 7,008,375 B2 | 3/2006 | Weisel |
| 7,025,751 B2 | 4/2006 | Silva et al. |
| 7,033,357 B2 | 4/2006 | Baxter et al. |
| 7,037,316 B2 | 5/2006 | McGuckin, Jr. et al. |
| RE39,152 E | 6/2006 | Aust et al. |
| 7,172,610 B2 | 2/2007 | Heitzmann et al. |
| 7,235,088 B2 | 6/2007 | Pintor et al. |
| 7,344,546 B2 * | 3/2008 | Wulfman et al. ............. 606/159 |
| 7,344,548 B2 | 3/2008 | Toyota et al. |
| 7,381,198 B2 * | 6/2008 | Noriega et al. ............... 606/194 |
| 7,399,307 B2 | 7/2008 | Evans et al. |
| 7,479,147 B2 | 1/2009 | Honeycutt et al. |
| 7,534,249 B2 | 5/2009 | Nash et al. |
| 7,666,161 B2 | 2/2010 | Nash et al. |
| 7,875,018 B2 | 1/2011 | Tockman et al. |
| 7,879,022 B2 | 2/2011 | Bonnette et al. |
| 7,981,128 B2 | 7/2011 | To et al. |
| 8,007,500 B2 | 8/2011 | Lin et al. |
| 8,007,506 B2 | 8/2011 | To et al. |
| 8,070,762 B2 | 12/2011 | Escudero et al. |
| 8,236,016 B2 | 8/2012 | To et al. |
| 8,337,516 B2 | 12/2012 | Escudero et al. |
| 8,361,094 B2 | 1/2013 | To et al. |
| 8,747,350 B2 | 6/2014 | Chin et al. |
| 2001/0005909 A1 | 6/2001 | Findlay, III et al. |
| 2002/0004680 A1 * | 1/2002 | Plaia et al. ................... 623/1.23 |
| 2002/0007190 A1 | 1/2002 | Wulfman et al. |
| 2002/0029057 A1 | 3/2002 | McGuckin, Jr. |
| 2002/0077642 A1 | 6/2002 | Patel et al. |
| 2002/0169467 A1 | 11/2002 | Heitzmann et al. |
| 2002/0198550 A1 | 12/2002 | Nash et al. |
| 2003/0018346 A1 | 1/2003 | Follmer et al. |
| 2003/0078606 A1 | 4/2003 | Lafontaine et al. |
| 2003/0100911 A1 | 5/2003 | Nash et al. |
| 2003/0114869 A1 | 6/2003 | Nash et al. |
| 2003/0125758 A1 | 7/2003 | Simpson et al. |
| 2003/0139802 A1 | 7/2003 | Wulfman et al. |
| 2004/0006358 A1 | 1/2004 | Wulfman et al. |
| 2004/0087988 A1 | 5/2004 | Heitzmann et al. |
| 2004/0097995 A1 | 5/2004 | Nash et al. |
| 2004/0102772 A1 | 5/2004 | Baxter et al. |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0199051 A1 | 10/2004 | Weisel |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0243162 A1 | 12/2004 | Wulfman et al. |
| 2005/0004585 A1 | 1/2005 | Hall et al. |
| 2005/0020974 A1 | 1/2005 | Noriega et al. |
| 2005/0059990 A1 | 3/2005 | Ayala et al. |
| 2005/0113853 A1 | 5/2005 | Noriega et al. |
| 2005/0149084 A1 | 7/2005 | Kanz et al. |
| 2005/0177068 A1 | 8/2005 | Simpson |
| 2005/0197661 A1 | 9/2005 | Carrison et al. |
| 2005/0222519 A1 | 10/2005 | Simpson |
| 2005/0240146 A1 | 10/2005 | Nash et al. |
| 2006/0020327 A1 | 1/2006 | Lashinski et al. |
| 2006/0074442 A1 | 4/2006 | Noriega et al. |
| 2006/0229646 A1 | 10/2006 | Sparks |
| 2006/0239982 A1 | 10/2006 | Simpson |
| 2006/0241564 A1 | 10/2006 | Corcoran et al. |
| 2007/0225739 A1 | 9/2007 | Pintor et al. |
| 2007/0250000 A1 | 10/2007 | Magnin et al. |
| 2007/0282303 A1 | 12/2007 | Nash et al. |
| 2007/0282350 A1 | 12/2007 | Hernest |
| 2007/0282358 A1 | 12/2007 | Remiszewski et al. |
| 2008/0004643 A1 | 1/2008 | To et al. |
| 2008/0004645 A1 | 1/2008 | To et al. |
| 2008/0045986 A1 | 2/2008 | To et al. |
| 2008/0140101 A1 | 6/2008 | Carley et al. |
| 2008/0249364 A1 | 10/2008 | Korner |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024085 A1 | 1/2009 | To et al. |
| 2010/0174302 A1 | 7/2010 | Heitzmann et al. |
| 2010/0324567 A1 | 12/2010 | Root et al. |
| 2010/0324576 A1 | 12/2010 | Pintor et al. |
| 2011/0040315 A1 | 2/2011 | To et al. |
| 2011/0112563 A1 | 5/2011 | To et al. |
| 2011/0152906 A1 | 6/2011 | Escudero et al. |
| 2011/0152907 A1 | 6/2011 | Escudero et al. |
| 2011/0270289 A1 | 11/2011 | To et al. |
| 2011/0301626 A1 | 12/2011 | To et al. |
| 2013/0085515 A1 | 4/2013 | To et al. |
| 2013/0090674 A1 | 4/2013 | Escudero et al. |
| 2013/0103062 A1 | 4/2013 | To et al. |

FOREIGN PATENT DOCUMENTS

| | | |
|---|---|---|
| EP | 0 817 595 B1 | 6/2002 |
| EP | 1 176 915 B1 | 10/2005 |
| EP | 1 158 910 B1 | 10/2007 |
| EP | 1 315 460 B1 | 12/2007 |
| EP | 1 722 694 B1 | 5/2009 |
| EP | 1 870 044 B1 | 7/2009 |
| JP | 1-131653 A | 5/1989 |
| JP | 08-509639 A | 10/1996 |
| JP | 09-508554 A | 9/1997 |
| JP | 11-506358 A | 6/1999 |
| JP | 2001-522631 A | 11/2001 |
| JP | 2004-503265 A | 2/2004 |
| JP | 2004-514463 A | 5/2004 |
| WO | WO-94/24946 A1 | 11/1994 |
| WO | WO-95/21576 A1 | 8/1995 |
| WO | WO-96/29941 A1 | 10/1996 |
| WO | WO-99/23958 A1 | 5/1999 |
| WO | WO-99/35977 A1 | 7/1999 |
| WO | WO-00/54659 A1 | 9/2000 |
| WO | WO-01/74255 A1 | 10/2001 |
| WO | WO-01/76680 A1 | 10/2001 |
| WO | WO-2005/123169 A1 | 12/2005 |
| WO | WO-2007/010389 A1 | 1/2007 |
| WO | WO-2008/005888 A2 | 1/2008 |

(56) References Cited

FOREIGN PATENT DOCUMENTS

| WO | WO-2008/005888 A3 | 1/2008 |
|---|---|---|
| WO | WO-2008/005891 A2 | 1/2008 |
| WO | WO-2008/005891 A3 | 1/2008 |
| WO | WO-2009/005779 A1 | 1/2009 |
| WO | WO-2009/054968 A1 | 4/2009 |
| WO | WO-2009/126309 A2 | 10/2009 |
| WO | WO-2009/126309 A3 | 10/2009 |

OTHER PUBLICATIONS

Ex-Parte Quayle Action mailed on Mar. 30, 2012, for U.S. Appl. No. 12/215,721, filed Jun. 30, 2008, 6 pages.
Final Office Action mailed on Feb. 3, 2010, for U.S. Appl. No. 11/551,193, filed Oct. 19, 2006, 8 pages.
Final Office Action mailed on May 25, 2010, for U.S. Appl. No. 11/551,191, filed Oct. 19, 2006, 11 pages.
Final Office Action mailed on Mar. 11, 2011, for U.S. Appl. No. 11/771,865, filed Jun. 29, 2007, 8 pages.
Final Office Action mailed on Apr. 15, 2011, for U.S. Appl. No. 12/215,854, filed Jun. 30, 2008, 8 pages.
Final Office Action mailed on Apr. 20, 2011, for U.S. Appl. No. 12/215,855, filed Jun. 30, 2008, 8 pages.
Final Office Action mailed on Jul. 13, 2011, for U.S. Appl. No. 12/215,752, filed Jun. 30, 2008, 7 pages.
Final Office Action mailed on Dec. 22, 2011, for U.S. Appl. No. 11/567,715, filed Dec. 6, 2006, 6 pages.
Final Office Action mailed on Dec. 22, 2011, for U.S. Appl. No. 12/215,721, filed Jun. 30, 2008, 6 pages.
Final Office Action mailed on Mar. 22, 2012, for U.S. Appl. No. 11/551,191, filed Oct. 19, 2006, 5 pages.
Final Office Action mailed on Nov. 6, 2012, for U.S. Appl. No. 12/930,077, filed Dec. 27, 2010, 6 pages.
Final Office Action mailed on Jan. 24, 2013, for U.S. Appl. No. 12/925,466, filed Oct. 22, 2010, 8 pages.
Final Office Action mailed on Feb. 6, 2013, for U.S. Appl. No. 13/182,844, filed Jul. 14, 2011, 10 pages.
Final Office Action mailed on Apr. 24, 2013 for U.S. Appl. No. 12/932,370, filed Feb. 24, 2011, 10 pages.
Final Office Action mailed on May 6, 2013 for U.S. Appl. No. 12/215,855, filed Jun. 30, 2008, 8 pages.
Final Office Action mailed on Jun. 13, 2013 for U.S. Appl. No. 12/215,752, filed Jun. 30, 2008, 9 pages.
Ikeno, F. et al. (2004). "Initial Experience with the Novel 6 Fr-Compatible System for Debulking De Novo Coronary Arterial Lesions," *Catheterization and Cardiovascular Interventions* 62:308-317.
International Preliminary Report on Patentability issued on Jan. 6, 2009, for PCT Patent Application No. PCT/US2007/072570, filed on Jun. 29, 2007, 4 pages.
International Preliminary Report on Patentability issued Jan. 6, 2009, for PCT Patent Application No. PCT/US2007/072574, filed on Jun. 29, 2007, 4 pages.
International Preliminary Report on Patentability issued on Jun. 30, 2010, for PCT Patent Application No. PCT/US2008/012012, filed on Oct. 22, 2008, 11 pages.
International Preliminary Report on Patentability issued on Aug. 6, 2010, for PCT Patent Application No. PCT/US2009/002253, filed on Apr. 10, 2009, 12 pages.
International Search Report mailed on Sep. 3, 2008, for PCT Patent Application No. PCT/US2007/72570, filed on Jun. 29, 2007, 1 page.
International Search Report mailed on Sep. 18, 2008, for PCT Patent Application No. PCT/US2007/072574, filed on Jun. 29, 2007, 1 page.
International Search Report mailed on Oct. 29, 2008, for PCT Patent Application No. PCT/US2008/08140, filed on Jun. 30, 2008, 1 page.
International Search Report mailed on Feb. 12, 2009, for PCT Patent Application No. PCT/US2008/12012, filed on Oct. 22, 2008, 1 page.
International Search Report mailed on Aug. 12, 2009, for PCT Patent Application No. PCT/US2009/02253, filed on Apr. 10, 2009, 1 page.

Kanjwal, M.K. et al. (2004). "Peripheral Arterial Disease—The Silent Killer," *JK-Practitioner* 11(4):225-232.
Nakamura, M. et al. (2002). "Efficacy and Feasibility of Helixcision for Debulking Neointimal Hyperplasia for In-Stent Restenosis," *Catheterization and Cardiovascular Interventions* 57:460-466.
Non-Final Office Action mailed on Apr. 3, 2009, for U.S. Appl. No. 11/551,193, filed Oct. 19, 2006, 7 pages.
Non-Final Office Action mailed on May 27, 2009, for U.S. Appl. No. 11/567,715, filed Dec. 6, 2006, 16 pages.
Non-Final Office Action mailed on Jul. 15, 2009, for U.S. Appl. No. 11/551,191, filed Oct. 19, 2006, 18 pages.
Non-Final Office Action mailed on Jun. 25, 2010, for U.S. Appl. No. 11/551,198, filed Oct. 19, 2006, 15 pages.
Non-Final Office Action mailed on Jun. 25, 2010, for U.S. Appl. No. 11/771,865, filed Jun. 29, 2007, 10 pages.
Non-Final Office Action mailed on Aug. 27, 2010, for U.S. Appl. No. 11/551,203, filed Oct. 19, 2006, 19 pages.
Non-Final Office Action mailed on Oct. 5, 2010, for U.S. Appl. No. 12/215,855, filed Jun. 30, 2008, 10 pages.
Non-Final Office action mailed on Oct. 5, 2010, for U.S. Appl. No. 12/215,752, filed Jun. 30, 2008, 8 pages.
Non-Final Office Action mailed on Oct. 12, 2010, for U.S. Appl. No. 12/215,854, filed Jun. 30, 2008, 11 pages.
Non-Final Office Action mailed on Apr. 14, 2011, for U.S. Appl. No. 12/215,721, filed Jun. 30, 2008, 9 pages.
Non-Final Office Action mailed on Aug. 4, 2011, for U.S. Appl. No. 11/551,191, filed Oct. 19, 2006, 6 pages.
Non-Final Office Action mailed on Aug. 4, 2011, for U.S. Appl. No. 11/567,715, filed Dec. 6, 2006, 9 pages.
Non-Final Office Action mailed on Apr. 27, 2012, for U.S. Appl. No. 12/925,466, filed Oct. 22, 2010, 7 pages.
Non-Final Office Action mailed on May 17, 2012, for U.S. Appl. No. 13/182,844, filed Jul. 14, 2011, 12 pages.
Non-Final Office Action mailed on Jun. 20, 2012, for U.S. Appl. No. 13/213,896, filed Aug. 19, 2011, 6 pages.
Non-Final Office Action mailed on Nov. 29, 2012, for U.S. Appl. No. 12/215,752, filed Jun. 30, 2008, 7 pages.
Non-Final Office Action mailed on Dec. 11, 2012, for U.S. Appl. No. 11/771,865, filed Jun. 29, 2007, 7 pages.
Non-Final Office Action mailed on Dec. 14, 2012, for U.S. Appl. No. 12/932,370, filed Feb. 24, 2011, 7 pages.
Non-Final Office Action mailed on Jan. 8, 2013, for U.S. Appl. No. 12/932,371, filed Feb. 24, 2011, 7 pages.
Non-Final Office Action mailed on Jan. 16, 2013, for U.S. Appl. No. 12/215,854, filed Jun. 30, 2008, 7 pages.
Non-Final Office Action mailed on Apr. 26, 2013, for U.S. Appl. No. 13/691,485, filed Nov. 30, 2012, 7 pages.
Non-Final Office Action mailed on May 17, 2013 for U.S. Appl. No. 12/930,077, filed Dec. 27, 2010, 8 pages.
Non-Final Office Action mailed on Jun. 24, 2013 for U.S. Appl. No. 13/715,664, filed Dec. 14, 2012, 9 pages.
Notice of Allowance mailed on Feb. 19, 2010, for U.S. Appl. No. 11/567,715, filed Dec. 6, 2006, 6 pages.
Notice of Allowance mailed on Jun. 18, 2010 for U.S. Appl. No. 11/567,715, filed Dec. 6, 2006, 6 pages.
Notice of Allowance mailed on Nov. 29, 2010, for U.S. Appl. No. 11/567,715, filed Dec. 6, 2006, 6 pages.
Notice of Allowance mailed on Dec. 10, 2010, for U.S. Appl. No. 11/551,193, filed Oct. 19, 2006, 7 pages.
Notice of Allowance mailed on Mar. 3, 2011, for U.S. Appl. No. 11/551,193, filed Oct. 19, 2006, 7 pages.
Notice of Allowance mailed on Jun. 3, 2011, for U.S. Appl. No. 11/551,203, filed Oct. 19, 2006, 10 pages.
Notice of Allowance mailed on Oct. 4, 2011, for U.S. Appl. No. 12/288,593, filed Oct. 22, 2008, 9 pages.
Notice of Allowance mailed on Dec. 13, 2011, for U.S. Appl. No. 12/384,970, filed Apr. 10, 2009, 11 pages.
Notice of Allowance mailed on Aug. 6, 2012, for U.S. Appl. No. 12/215,721, filed Jun. 30, 2008, 8 pages.
Notice of Allowance mailed on Aug. 22, 2012, for U.S. Appl. No. 13/309,986, filed Dec. 2, 2011, 10 pages.

(56) References Cited

OTHER PUBLICATIONS

Notice of Allowance mailed on Sep. 18, 2012, for U.S. Appl. No. 11/567,715, filed Dec. 6, 2006, 8 pages.
Notice of Allowance mailed on Feb. 6, 2013, for U.S. Appl. No. 13/213,896, filed Aug. 19, 2011, 8 pages.
Notice of Allowance mailed on May 15, 2013, for U.S. Appl. No. 11/551,191, filed Oct. 19, 2006, 10 pages.
Notice of Allowance mailed on Jun. 18, 2013, for U.S. Appl. No. 11/551,191, filed Oct. 19, 2006, 5 pages.
Notice of Allowance mailed on Jun. 21, 2013, for U.S. Appl. No. 12/215,721, filed Jun. 30, 2008, 10 pages.
Notice of Allowance mailed on Jul. 1, 2013, for U.S. Appl. No. 13/213,896, filed Aug. 19, 2011, 10 pages.
Supplementary European Search Report mailed on Jun. 20, 2011, for EP Patent Application No. 08779894.8, filed on Jun. 30, 2008, 7 pages.
Supplementary European Search Report mailed on Jun. 26, 2013, for EP Patent Application No. 08841648.2, filed on May 21, 2010, 5 pages.

* cited by examiner

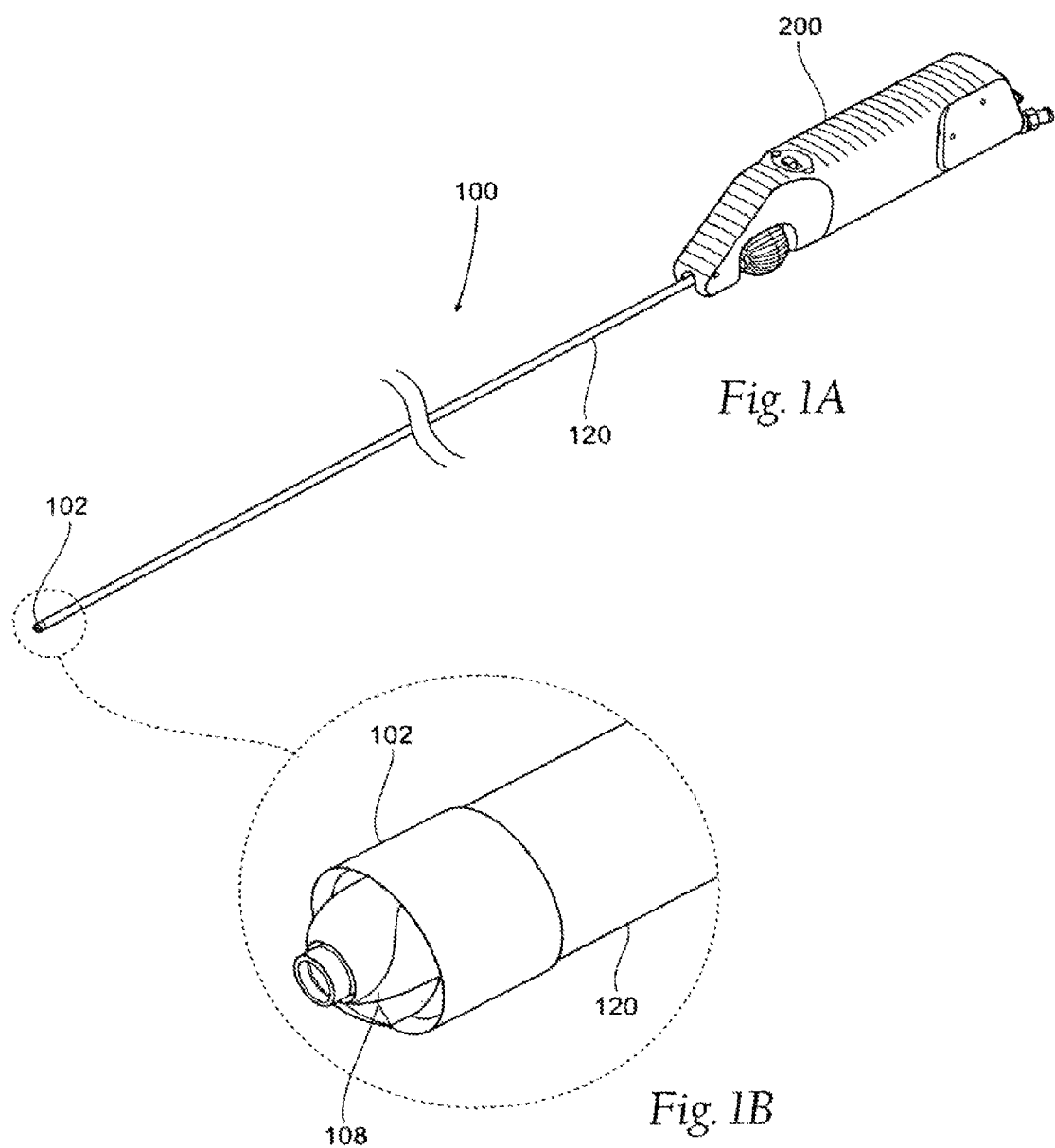

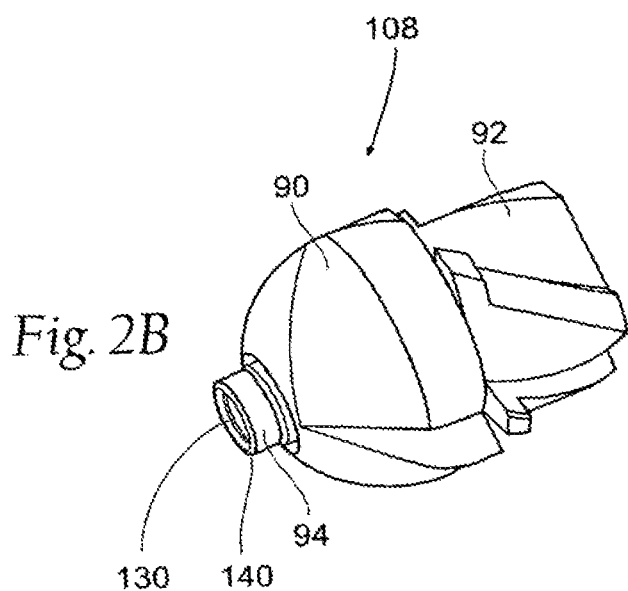
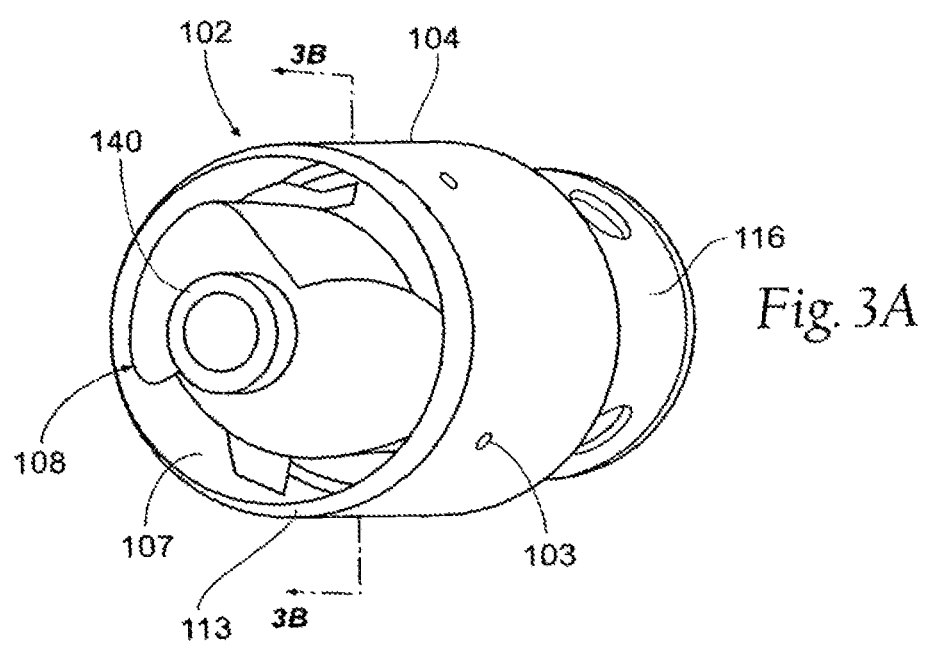

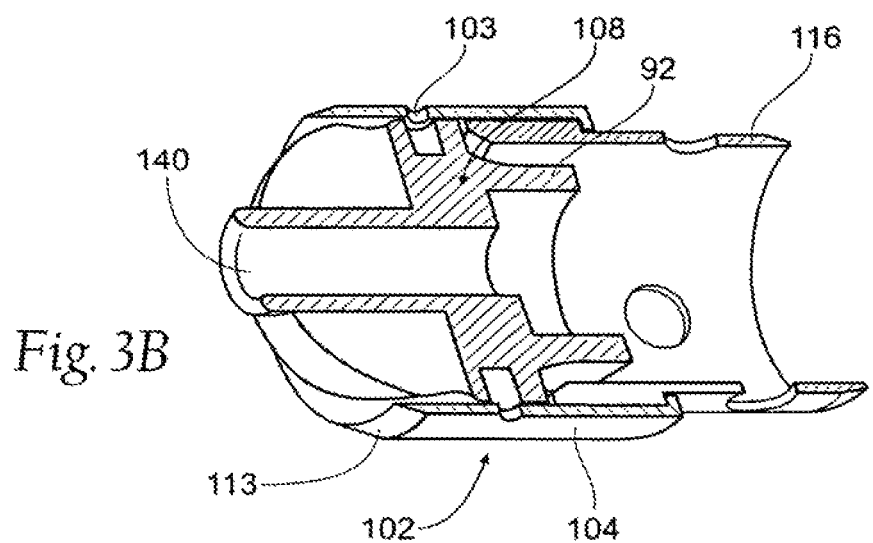
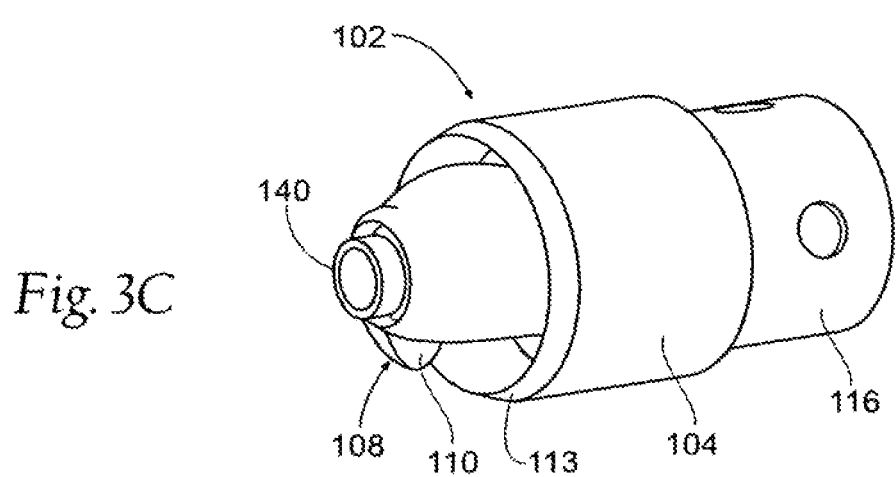

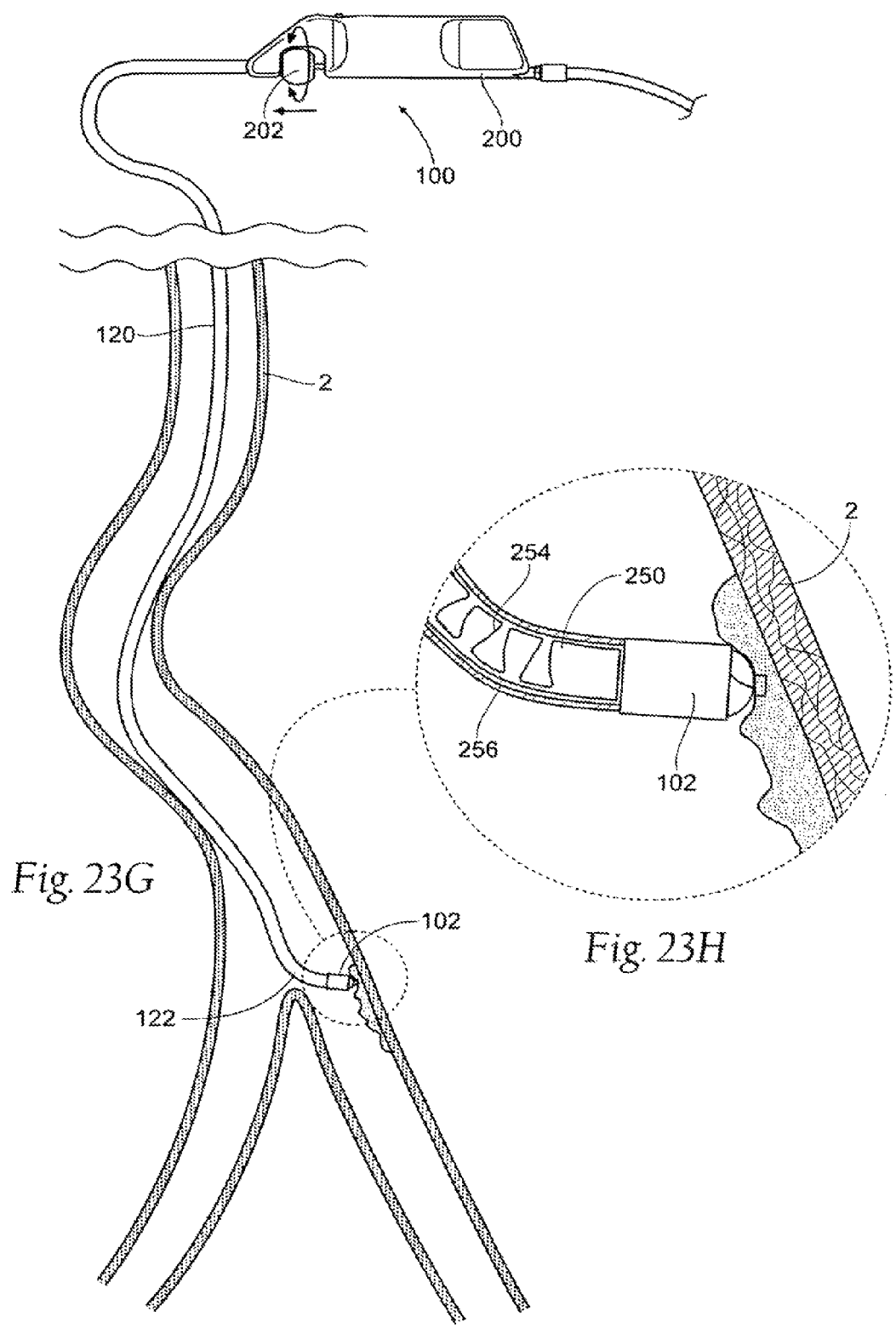

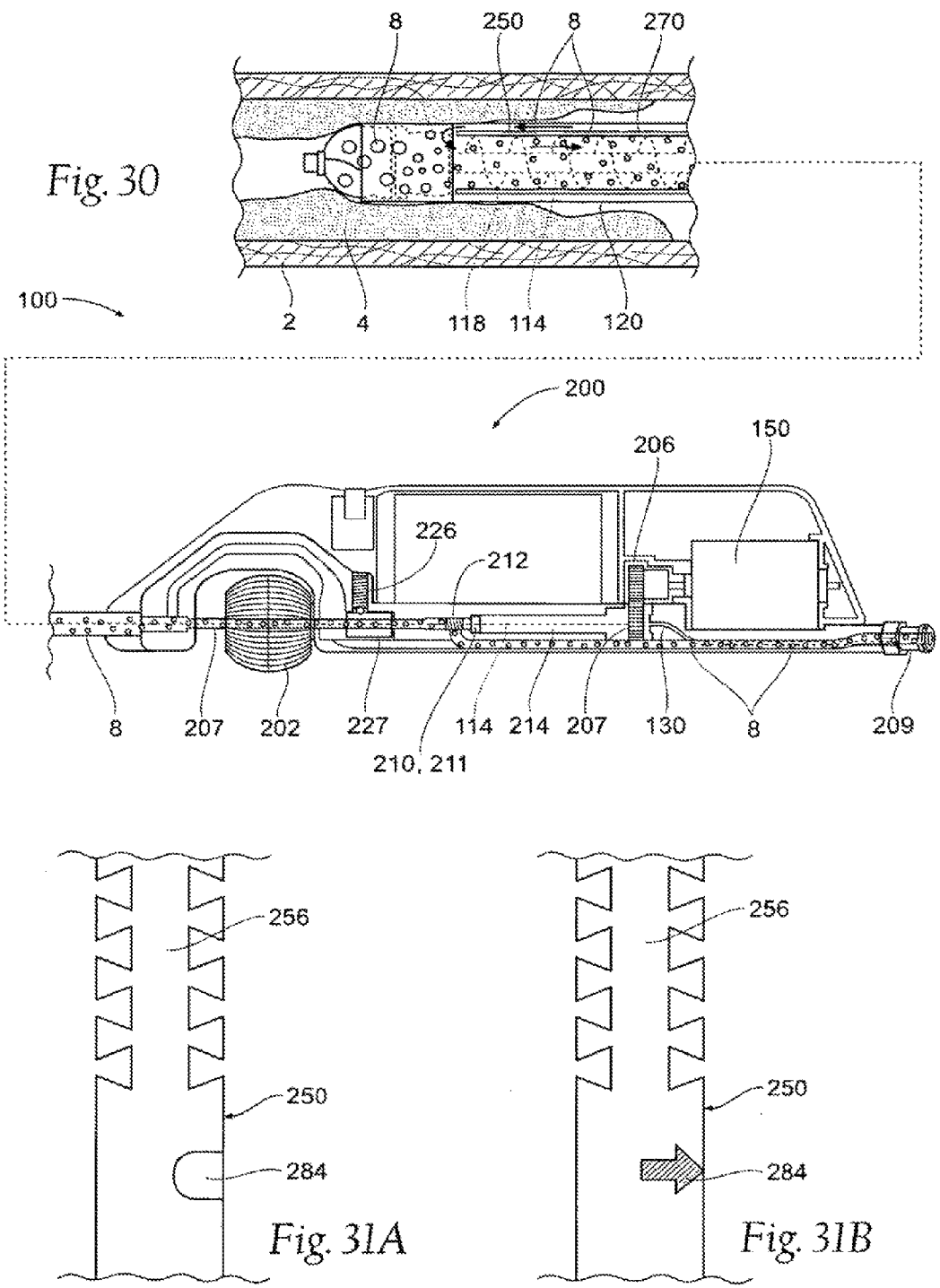

DEVICES, SYSTEMS, AND METHODS FOR PERFORMING ATHERECTOMY INCLUDING DELIVERY OF A BIOACTIVE MATERIAL

RELATED APPLICATIONS

This application is a continuation of U.S. application Ser. No. 12/932,371, filed Feb. 24, 2011 and titled "Devices, Systems, and Methods for Performing Atherectomy Including Delivery of a Bioactive Material," which is a divisional of co-pending U.S. patent application Ser. No. 12/215,752, filed Jun. 30, 2008 and entitled "Atherectomy Devices, Systems, and Methods," which claims the benefit of U.S. Provisional Patent Application Ser. No. 61/043,998, filed Apr. 10, 2008, and entitled "Atherectomy Devices and Methods," which is incorporated herein by reference.

U.S. application Ser. No. 12/215,752 also claims the benefit of U.S. Provisional Patent Application Ser. No. 60/981,735, filed Oct. 22, 2007, and entitled "Atherectomy Devices and Methods," which is incorporated herein by reference.

U.S. application Ser. No. 12/215,752 is also a continuation-in-part of co-pending U.S. patent application Ser. No. 11/771,865, filed Jun. 29, 2007, and entitled "Atherectomy Devices and Methods," which is a continuation-in-part of co-pending U.S. patent application Ser. No. 11/567,715, filed Dec. 6, 2006, and entitled "Atherectomy Devices and Methods," which is a continuation of co-pending U.S patent application Ser. No. 11/551,191, filed Oct. 19, 2006, and entitled "Atherectomy Devices and Methods," which claims the benefit of U.S. Provisional Patent Application Ser. No. 60/806,417, filed Jun. 30, 2006 and which also claims the benefit of U.S. Provisional Patent Application Ser. No. 60/820,475, filed Jul. 26, 2006, and entitled "Atherectomy Device," which are all incorporated herein by reference.

FIELD OF THE INVENTION

The devices, systems, and methods generally relate to treatment of occluded body lumens, e.g., for removal of occluding material from a blood vessel as well as other body parts.

BACKGROUND OF THE INVENTION

I. Peripheral Arterial Disease

Peripheral Arterial Disease (PAD) is a progressive disease. In this disease, lesions of the arteries are formed by accumulation of plaque and neointimal hyperplasia causing an obstruction of blood flow. Plaque (the build-up of cholesterol, cells, and other fatty substances) is often friable and may dislodge naturally or during an endovascular procedure, possibly leading to embolization of a downstream vessel.

It is estimated that 12 million people in the United States suffer from PAD that if left untreated has a mortality rate of 30 percent at five years. There are approximately 160,000 amputations each year from critical limb ischemia, the most severe subset of patients having PAD. The prevalence of PAD is on the rise, with risk factors including age, obesity, and diabetes.

Endovascular clearing procedures to reduce or remove the obstructions to restore luminal diameter and allow for increased blood flow to normal levels are known. Removing the plaque has the effect of removing diseased tissue and helps to reverse the disease. Maintaining luminal diameter for a period of time (several to many weeks) allows remodeling of the vessel from the previous pathological state to a more normal state. It is also the goal of an endovascular clearing procedure to prevent short term complications such as embolization or perforation of the vessel wall, and long term complications such as ischemia from thrombosis or restenosis.

II. Prior Treatment Modalities

Online coronary artery disease, current treatment options for PAD, including PAD in the arteries of the leg, have significant limitations for at least three main reasons: A) large volumes of plaque build up in very long, diffuse lesions, B) low blood flow promotes thrombus formation and plaque buildup, and C) arteries of the leg are bent, twisted, stretched, and pinched shut during routine movement.

Various treatment modalities have been tried to accomplish treatment goals. In atherectomy, plague is cut away, or excised. Various configurations have been used including a rotating cylindrical shaver or a fluted cutter. The devices may include some form of shielding by a housing for safety purposes. The devices may incorporate removal of debris via trapping the debris in the catheter, in a downstream filter, or aspirating the debris, for example. In some cases a burr may be used instead of a cutter, particularly to grind heavily calcified lesions into very small particle sizes. Aspiration may also be used with a burr-type atherectomy device.

A current example of an atherectomy device is the Silver-Hawk® Plaque Excision System by Fox Hollow Technologies. The SilverHawk has a number of limitations including the length of time the procedure takes to clear a lumen, it requires multiple devices and repeated catheter exchanges, it produces embolic debris, and it uses an unguarded cutter design that requires great patience and care to open the lumen while sparing the vessel wall. In use, the physician advances the catheter through the lesion, shaving plaque off of the artery walls and collecting the plaque in a long receptacle (nosecone) at the tip of the catheter (which must have enough room in the vessel to pivot to access the cutting blade). As the receptacle fills, the catheter must be removed, the receptacle emptied, and the procedure repeated until enough plaque is removed to restore normal blood flow. The procedure may include replacing the catheter with a larger diameter catheter to expand the size of the clearing. The long receptacle at the tip of the catheter limits the use of the device to mainly straight lumens.

Balloon angioplasty is another type at endovascular procedure. Balloon angioplasty expands and opens the artery by both displacing the plaque and compressing it by expanding a balloon in the artery, with some variations including a drug coated balloon. Balloon angioplasty is known to cause barotrauma to the vessel from the high pressures required to compress the plaque, and can also cause dissection of the vessel wall. This trauma leads to an unacceptably high rate of restenosis. Furthermore, this procedure may not be efficient for treatment of elastic-type plaque tissue, where such tissue can spring back to occlude the lumen.

Cryoplasty has been available for only a few years and has provided only limited positive results. With cryoplasty, the main problem appears to be restenosis after an extended period, such as a year. The technique is similar to balloon angioplasty procedures used in heart vessels, except stents are not used to keep the blood vessel open. With cryoplasty, the balloon is cooled to about −10 degrees Celsius (14 degrees Fahrenheit) by evaporating liquid nitrous oxide into a gas upon entering the balloon. The plaque clogging the artery cracks when it freezes, allowing for a more uniform dilation of the blood vessel than occurs in a standard angioplasty procedure.

Various forms of laser atherectomy have been developed and have had mixed results. One main limitation of a laser system is that the laser can only be effectively used in a straight lumen, and is less effective in or around tortuous lumens. When the laser is in position, it emits pulsating beams of light that vaporize the plaque. Laser systems have been less effective for removing calcified legions because of the laser properties.

Stenting may also be used as a treatment option. On their own, stents, including drug eluding stents, fail to perform well in the peripheral vasculature for a variety of reasons. A stent with the necessary structural integrity to supply sufficient radial force to reopen the artery often does not perform well in the harsh mechanical environment of the peripheral vasculature. For example, the peripheral vasculature encounters a significant amount of compression, torsion, extension, and bending. Such an environment may lead to stent failure (strut fracture, stent crushing, etc.) that eventually compromises the ability of the stent to maintain lumen diameter over the long-term. Stenting is also susceptible to in-stent restenosis, typically at a restenosis rate of 30 percent or higher. Stent fracture or restenosis may require subsequent vascular bypass surgery, which is invasive and is limited in the types of lesions or artery obstructions that may produce acceptable results. Stenting is not advisable in regions which would be candidates for proximal or distal anastamosis during surgical bypass procedures, because a stent in that region makes bypass difficult or impossible.

On the other hand, a stent that is able to withstand the harsh mechanical aspects of the periphery often will not supply enough radial force to open the vessel satisfactorily. In many cases, medical practitioners desire the ability to combine endovascular clearing procedures with stenting. Such stenting may occur prior to, after, or both before and after the endovascular clearing procedure.

Accordingly, a need remains for devices, systems, and methods that allow for improved atherectomy systems that are able to navigate through tortuous anatomy and clear materials from body lumens (such as blood vessels) where the systems includes features to allow for a safe, efficient and controlled fashion of shaving or grinding material within the body lumen while minimizing procedure times. In addition, there remains a need for systems that allow steering of the distal portion of the system while navigating through tortuous anatomy. The ability to steer assists the physician in accessing tortuous anatomy and can further assist in delivering a guidewire into the entrance of angled or tortuous vessel bifurcation/segments. This is possible because variations of the steerable atherectomy catheter system described herein can also function as a 'shuttle catheter', where the physician can aim the distal tip into the vessel to be accessed and advancing the guidewire into that vessel from within the catheter There also remains a need for devices that are configured to steer but will remain in a straight configuration when not being articulated. It is generally known that conventional catheters that take a shape often bias to one side either through repeated articulation or even after being left in packing for any given period of time. Accordingly, when such steering features are combined with tissue debulking systems, there remains a risk of injury if the tissue debulking system has an undesirable bend when the device is intended to be in a straight configuration.

The debulking devices, systems, and methods described herein address the problems noted above as well as provide significant improved features to allow a physician to steer a debulking device through tortuous anatomy and remove tissue at a target site.

SUMMARY OF THE INVENTION

One aspect of the invention provides a method for treating a region of a blood vessel. The method includes deploying a vascular device into a region of a blood vessel having an occlusive material. The vascular device comprises a catheter body having at its distal end a cutter assembly. The cutter assembly comprises a housing having at least one opening and a cutter having at least one helical cutting surface configured to rotate about the central axis relative to the housing to cut and convey occlusive material from the region proximally into the housing. The vascular device also includes a drive mechanism at a proximal end of the catheter body, and a torque shaft coupled to the drive mechanism and extending through the catheter body and coupled to the cutter to rotate the helical cutting blade about the center axis relative to the housing.

In one embodiment, the vascular device includes a conveyor mechanism helically wound about the torque shaft in a direction common with the helical cutting blade to rotate and thereby convey occlusive material from the region further proximally along the catheter body for discharge without supplement of a vacuum pump. In this embodiment, the method comprises performing an atherectomy in the identified region by operating the drive mechanism to rotate the helical cutting surface to cut and convey occlusive material from the identified region proximally into the housing, the drive mechanism also operating to rotate the conveyor mechanism to convey the occlusive material further proximally along the catheter body for discharge without supplement of a vacuum pump. The method can include visualizing the identified region before, during, and after performing the atherectomy.

In one embodiment, the vascular device includes a deflecting mechanism at the proximal end of the catheter body for deflecting the distal end of the catheter body relative to a center axis of the catheter body. In this embodiment, the method comprises performing an atherectomy in the identified region by operating the drive mechanism to rotate the helical cutting surface to cut and convey occlusive material from the identified region proximally into the housing, and deflecting the distal end of the catheter body relative to a center axis of the catheter body, and rotating the distal end of the catheter body while the distal end is deflected to sweep the cutter assembly in an arc about the center axis to cut the occlusive material in a region larger than an outside diameter of the cutter assembly. The method can include visualizing the identified region before, during, and after performing the atherectomy.

According to this aspect of the invention, in either embodiment, the method includes introducing into the identified region a bioactive material before, after or during performing the atherectomy in the identified region. Introducing the bioactive material can comprise, e.g., introducing into the identified region a balloon coated with a bioactive material, and expanding the balloon in contact with the identified region to deliver the bioactive material. The bioactive material can comprise, e.g., at least one of a restenosis-inhibiting agent, a thrombus-inhibiting agent, and an anti-inflammatory agent.

In one embodiment, the method further includes after conveying at least some of the occlusive material from the identified region, placing a stent structure in the identified region. In one embodiment, after placing the stent structure, the method further includes performing an atherectomy to remove residual occlusive material from the stent structure. In one embodiment, the method includes, after placing the stent structure, introducing a bioactive material into the stent structure. The bioactive material can comprise, e.g., at least one of a restenosis-inhibiting agent, a thrombus-inhibiting agent, and an anti-inflammatory agent.

The blood vessel can comprise, e.g., a peripheral blood vessel, e.g., a peripheral blood vessel in a leg, or a peripheral blood vessel in a leg below a knee.

As noted herein, combinations of aspects of the devices, systems, and methods described herein may be combined as needed. Furthermore, combinations of the devices, systems and methods themselves are within the scope of the disclosure.

BRIEF DESCRIPTION OF THE DRAWINGS

FIG. 1A is a perspective view of a system adapted for the removal of occluding material from body lumens according to the present invention.

FIG. 1B is a close up perspective view of the distal tip of the system shown in FIG. 1A, showing an embodiment of a cutting assembly.

FIG. 2B is a perspective view of a two piece cutter shown in FIG. 2A.

FIGS. 3A to 3C show a cutter assembly having a dynamic housing where the external housing acts as a cutter in conjunction with an internal two flute cutter.

FIGS. 23A through 23H show the debulking system in use for both passive and active steering through a tortuous vessel and to a treatment site.

FIG. 30 shows a schematic view of the debulking system, the system cutting debris, and aspirating the debris through the catheter, into the catheter chassis, and out the aspiration port.

FIGS. 31A and 31B show variations of a sweep frame having a visualisation feature that permits a physician to determine orientation and direction of articulation of the cutting assembly when the device is viewed under non-invasive imaging.

DESCRIPTION OF THE PREFERRED EMBODIMENT

Figure 2A:
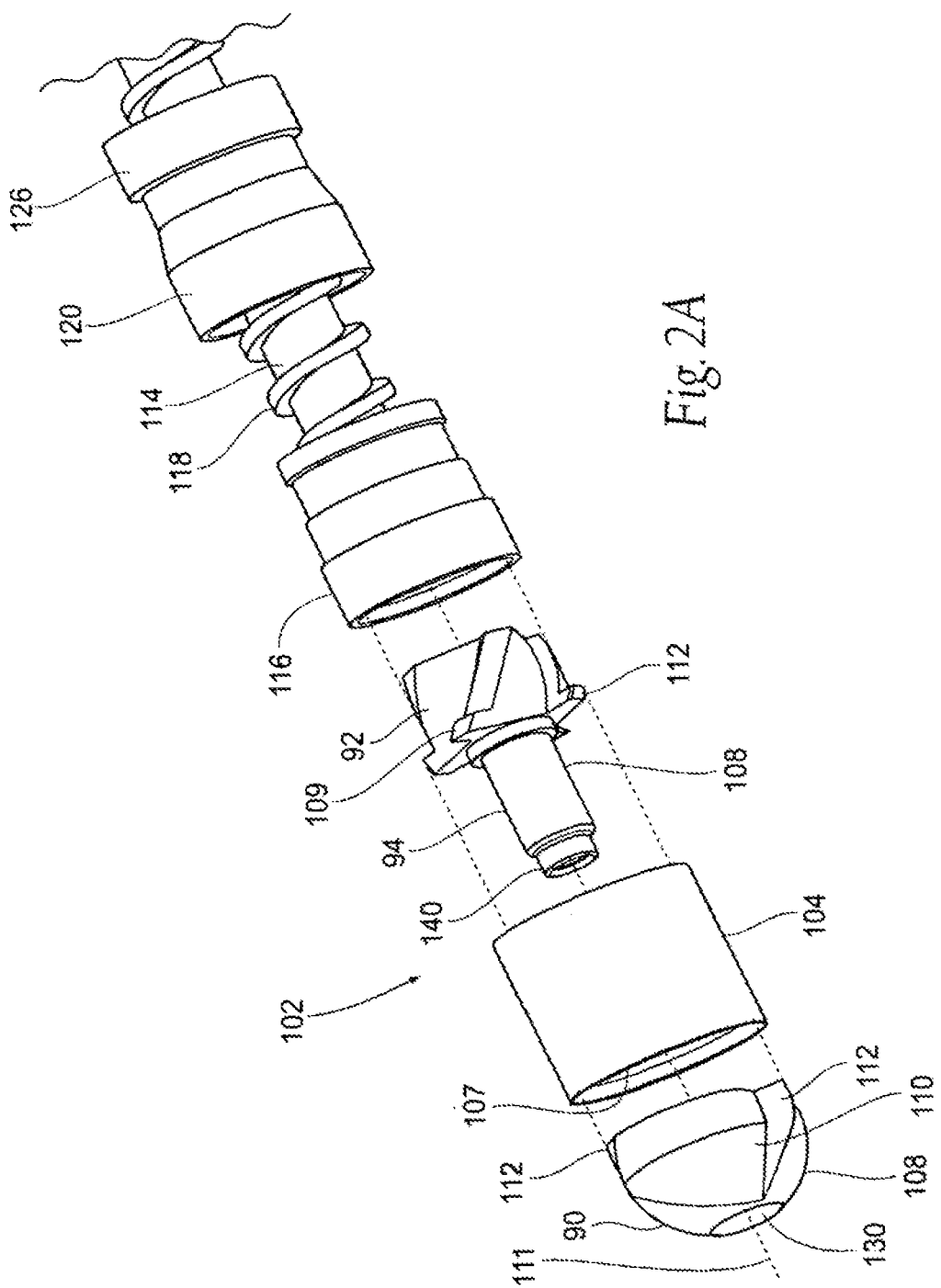
FIG. 2A is a perspective exploded view showing the cutting assembly of FIG. 1B.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

This specification discloses various catheter-based devices, systems, and methods for removing occluding materials from body lumens, including removing plaque, thrombus, calcium, and soft elastic tissues in blood vessels. For example, the various aspects of the invention have application in procedures requiring the treatment of diseased and/or damaged sections of a blood vessel. The devices, systems, and methods that embody features of the invention are also adaptable for use with systems and surgical techniques that are not necessarily catheter-based.

The devices, systems, and methods are particularly well suited for continuous debulking and aspiration of occluding material in the peripheral vasculature, including arteries found in the legs, such as the common femoral artery, superficial femoral artery, profunda femorus artery, popliteal artery, and tibial artery, as non-limiting examples. For this reason, the devices, systems, and methods will be described in this context. Still, it should be appreciated that the disclosed devices, systems, and methods are applicable for use in treating other dysfunctions elsewhere in the body, which are not necessarily artery-related.

When referring to catheter based apparatus or devices that are manipulated by a physician or operator in order to remove occluding materials from a body lumen, the terms "proximal" and "distal" will be used to describe the relation or orientation of the apparatus or device with respect to the operator as it is used. Therefore, the term "proximal" will be used to describe a relation or orientation of the apparatus or device that, when in use, is positioned toward the operator (i.e., at the "handle" end of the device), and the term "distal" will be used to describe a position or orientation of the apparatus or device that, when in use, is positioned away from the operator (i.e., at the "cutter" end of a catheter or the like away from the handle).

When referring to plaque in a vessel, or a partial or complete blockage in a vessel or body organ, the terms "proximal" and "distal" will be used to describe the relation or orientation of the plaque or blockage with respect to the heart. Therefore, the term "proximal" will be used to describe a relation or orientation of the plague or blockage that is toward the heart, and the term "distal" will be used to describe a position or orientation of the plaque or blockage that is away from the heart, i.e., toward the feet.

I. System Overview

A. System Capabilities

FIGS. 1A and 1B illustrate an exemplary variation of a system 100 according to the present invention, the system 100 adapted for thrombectomy and/or atherectomy. As shown, the system 100 includes a distal cutter assembly 102 affixed to a catheter body or catheter assembly 120, with the catheter assembly coupled to a control handle 200 at a proximal end. It is noted that the assemblies shown in the figures are for exemplary purposes only. The scope of this disclosure includes the combination of the various embodiments, where possible, as well as the combination of certain aspects of the various embodiments.

The system 100 provides substantial ease of use, performance, and safety advantages over prior debulking types of devices. As will be described in greater detail throughout this specification and Figures, the system 100 may include 360 degree steerable rotational cutting, a guarded (shielded) or open cutter at the distal end of a catheter, with the catheter coupled to a hand-held controller (i.e., handle) that is adapted to allow continuous debulking and aspiration of lesions ranging from fresh thrombus to calcified plaque. The debris is trapped within the catheter as it is cut, and may be continuously removed.

The devices, systems, and methods described herein work particularly well in lesions that are challenging to treat with other systems, i.e., at bifurcations, in tortuous arteries, and in arteries which are subject to biomechanical stresses, such as arteries in the periphery, e.g., located within the knee or other joints (as will be described in greater detail later).

The devices, systems, and methods can also perform a wide variety of other treatments, including biopsies, tumor removal, fibroid treatment, debulking of unwanted hyperplastic tissues such as enlarged prostate tissue, or other unwanted tissue such as herniated spinal disc material. Any of the devices, systems, and methods described herein may also be used as a tool to treat chronic total occlusions (CTO) or a complete blockage of the artery. The flexible, low profile catheter systems described herein allow for ease of access to the treatment site and minimizes trauma or collateral damage to surrounding healthy tissue. With a continuous aspiration capability, contamination of the surrounding tissue during device introduction, treatment, and removal is reduced or even eliminated. In addition, aspiration can be used to transfer biopsy tissue samples to outside the body for testing with the catheter remaining in situ. This helps the physician make real time decisions in advancing treatment of malignant tissue.

A shield or housing on the cutter assembly 102 maintains controlled excision of tissue by limiting the depth of cutter engagement and thereby prevents the physician from inadvertently cutting into healthy surrounding tissue. The tip steering capability of the system allows the physician to direct the cutter 108 towards desired site of tissue removal and minimizing collateral tissue damage. By deflecting the cutter and rotating the deflection to sweep in an arc, the catheter can excise large plaque deposits, tumors, or tissue lumps larger than the diameter of the catheter. Thus, excision of large tumors can be achieved through a small access channel and thereby minimizing trauma to the patient.

The devices, systems, and methods described herein can also debulk stenosis in arteriovenous (AV) hemodialysis access sites (fistulae and synthetic grafts), as well as to remove thrombus. For example, by removing the cutter housing and recessing the fluted cutter within the catheter body, a suitable non-cutting thrombectomy catheter may be constructed.

The devices, systems, and methods described herein can also be used for excising bone, cartilage, connective tissue, or muscle during minimally invasive surgical procedures. For example, a catheter that includes cutting and burr elements may be used to gain access to the spine for performing laminectomy or facetectomy procedures to alleviate spinal stenosis. For this application, the catheter may be further designed to deploy through a rigid cannula over part of its length, or have a rigid portion itself, to aid in surgical insertion and navigation.

Figure 35:
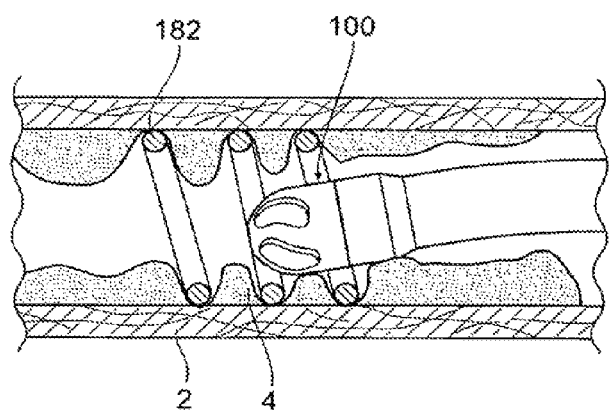
FIG. 35 shows a cutting assembly removing lesions within a stent or coil.

It is also possible to use the devices, systems, and methods described herein to restore patency to arterial lesions in the coronary circulation and in the cerebrovascular circulation, both by debulking de novo lesions and by debulking in-stent restenosis. FIG. 35 shows the system 100 removing lesions within a stent or coil.

II. Desirable Technical Features

The debulking system 100 can incorporate various technical features to enhance its usability, which will now be described.

A. The Cutter Assembly

1. Cylindrical Housing Cutter Assemblies

FIG. 2A illustrates an exploded view of an exemplary embodiment of a front cutting cutter assembly 102. In this variation, the cutter assembly 102 includes a cylindrical housing 104 having an opening 107 located on its distal face adapted to allow a cutter 108 to extend beyond the distal face. The cutter 108 may comprise one or more cutting edges. In the illustrated embodiment, the cutting edges comprise a first set of cutting edges 112 that extend along (or substantially along) the cutter 108 and a second cutting edge 109 that extends only along a portion of the cutter 108. Although the number of cutting edges can vary, typically the cutting edges will be symmetric about an axis 111 of the cutter 108.

FIG. 2B also shows a variation of the cutter 108 that comprises a distal portion 90 mounted on a proximal portion 92 (where the proximal cutter portion 92 can also be referred to as a cutter core adapter 92). The proximal cutter portion 92 contains a shaft 94 terminating in a mating piece 140, with the mating piece 140 nested within an opening in the front face of the distal cutter 90. The cutter assembly 102 can also include a guidewire lumen 130 to allow for passing of a guidewire through the cutter assembly 102 and device 100.

The cutter 108, as described herein, is preferably made of hard, wear-resistant material such as hardened tool or stainless steels, Tungsten carbide, cobalt chromium, or titanium alloys with or without wear resistant coatings, such as Titanium Nitride. However, any material commonly used for similar surgical applications may be employed for the cutter. The outer surfaces of the proximal end of the cutter 108 are typically blunt and are designed to bear against the housing 104. Typically, these surfaces may be parallel to the inner surface of the housing 104.

FIGS. 3A to 3E illustrate additional variations of the cutter assembly 102. In such a variation, the front edge of the housing 104 can function as a front or forward cutting surface 113. In one variation, the cutter 108 may be tapered or rounded such that the front of the cutter comprises a rounded or partial-ball shape. As shown, the front cutting surface 113 can be beveled on an outside surface of the housing 104. Such a beveled feature reduces the risk of the cutting surface 113 from gouging or otherwise damaging the wall of a vessel. As noted above, the forward cutting surface 113 engages and removes tissue or plaque 4 when the device is advanced in a distal direction within a body lumen 2 as shown in FIG. 3F. As discussed herein, features of the device 100 include a guidewire 128 to assist in preventing the device from excessively cutting the lumen wall 2.

The housing 104 can either be configured to rotate with the cutter 108 or can be stationary and function as a scraping, scooping, or chisel type surface. For example, FIGS. 3A and 3B show a variation where the housing 104 can be affixed to the cutter 108 allowing for rotation of the entire cutting assembly 102 about the catheter body 120. The system may also include a ferrule 116 that permits coupling of the catheter body 120 to the cutter assembly 102. The ferrule 116 may serve as a bearing surface for rotation of the cutter 108 within the cutter assembly 102. In the illustrated example, the cutting assembly 102 includes adjoining recessed pin cavities 103 for securing the housing 104 to the cutter 108. FIG. 3B shows a cross sectional view of the cutter assembly 102 of FIG. 3A. As illustrated, in this particular variation, the entire cutting assembly 102 rotates relative to the ferrule 116 which provides a bearing surface for the rotational housing 104. The proximal portion 92 of the cutter 108 rotates within the ferrule while the proximal end of the housing 104 rotates about the ferrule 116.

The housing 104 can be linked to the cutter 108 in a variety of ways as is well understood by those skilled in the art. For example the housing 104 can be directly linked or affixed to the cutter 108 via connection points 103 so that both rotate together. Alternatively, the housing 104 can be geared to rotate faster or slower than the cutter 108. In yet another variation, the gearing can be chosen to permit the housing 104 to rotate in an opposite direction than the cutter 108.

Variations of the cutting assemblies include cutters 108 that protrude partially from the forward cutting surface 113 of the housing 104. In other variations, the cutter 108 can extend further from the housing 104 or the assemblies can comprise cutters 108 that are totally recessed within the housing 104. In certain variations, it was identified that aligning the cutting surface 113 of the housing 104 with the deepest part of a flute 110 on the cutter 108 allows for improved clearing of debris, especially where a single or double fluted cutting edge configuration is used on a distal portion of the cutter 108.

In any case, the fluted cutting edge 112 impels tissue debris back into the catheter. The outer surface of the housing, proximal to the forward cutting surface 113 can be smooth to protect the lumen wall from the cutting action of the cutting edges. When the cutting assembly 102 is deflected, the outer surface of the housing 104 becomes flush against the lumen wall and prevents the cutting edges from engaging the vessel wall. As the cutter assembly is advanced forward, it removes plaque 4 protruding from the lumen 2 wall and tissue debris is impelled backwards by the fluted edge 112 of the cutter 108.

FIG. 3C illustrates an additional variation of a cutting assembly 102 where a housing 104 of the cutting assembly 102 remains stationary about a catheter body 120 or ferrule 116 while the cutter 108 rotates within the ferrule. In this embodiment, the inner portion of the ferrule 116 may provide a bearing surface for the proximal end 92 of the cutter 108. The housing 104 may be affixed to the ferrule 116 and may also function as a bearing surface for the rotating cutter 108. The cutter 108 rotates relative to the housing 104 such that, the cutting surface 112 on the cutter 108 shears or cleaves tissue and traps the tissue inside the housing 104 so that it can be evacuated in a proximal direction using the impeller action of the helical flutes 110 and vacuum from the torque shaft 114 and/or conveying member 118.

Figure 3D:
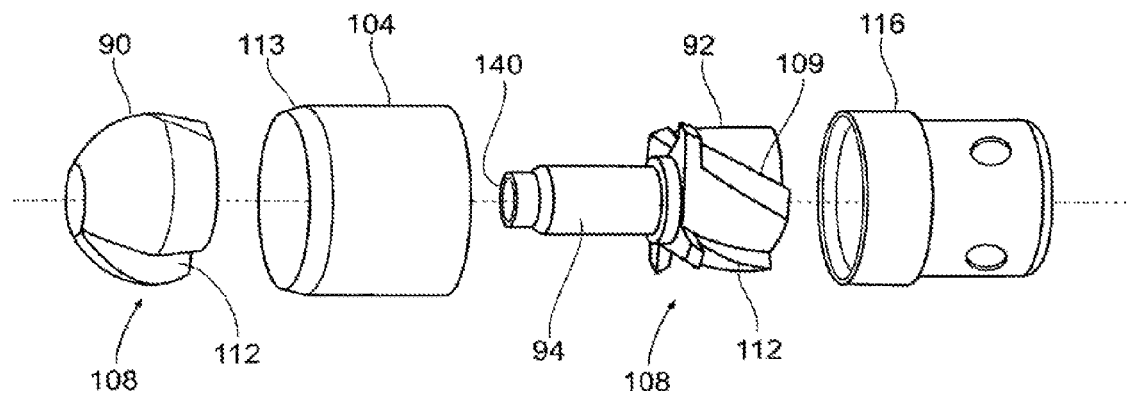
FIG. 3D shows an exploded view of the cutter assembly of FIG. 3C.
Figure 3E:
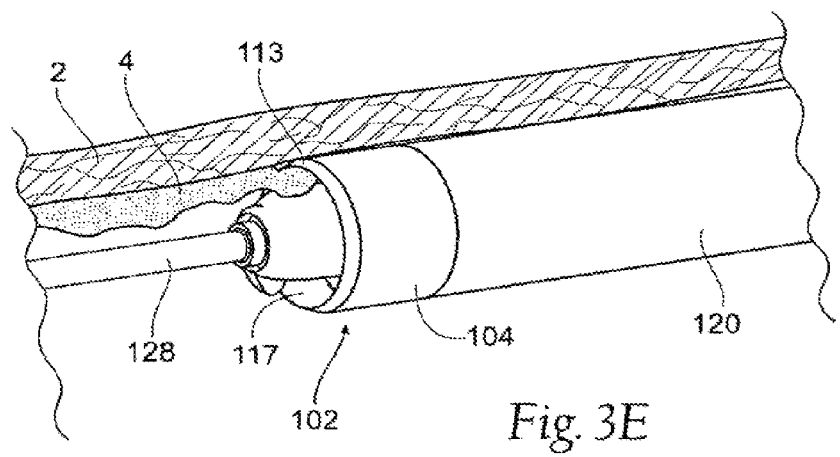
FIG. 3E shows a perspective view of a cutter assembly with a dynamic housing removing material from a lumen wall.

FIG. 3E shows an exploded view of the cutting assembly of FIG. 3C. Again, the cutter 108 can include a distal cutting portion 90 and a proximal cutting portion 92. The illustrated configuration provides a device having fewer cutting edges 112 on a distal portion 90 of the cutter and increased cutting edges 109 and 112 on a proximal cutting portion 92. However, variations include a traditional fluted cutter as well. The housing 104 is mounted about the cutter portions 90 and 92 and optionally secured to either the catheter body 120 or ferrule 116. As noted above, the housing 104 can also be affixed to the cutter so that it rotates with the cutter.

In alternate variations, the mating surface 140 of the cutter assembly 102 can function as a blunt bumper at the very tip of the cutter 108 that acts as a buffer to prevent accidental cutting into the guidewire or the vessel wall given the cutter assemblies' open distal design. In additional variations, the housing 104 could be expandable (such as a basket or mesh). As the cutter 108 gyrates inside the housing, the housing may be adapted to expand to cut a larger diameter.

FIG. 3F illustrates a cutting assembly 102 having a forward cutting surface 113 at a distal opening 117 of a housing 104. The housing 104 rotates along with the cutter 108 to assist in removal of tissue. As noted above, the forward cutting surface 113 engages and removes tissue or plaque 4 when the device is advanced in a distal direction within a body lumen 2. As discussed below, features of the device, including a guidewire 128 assist in preventing the device from excessively cutting the lumen wall 2.

Figure 4A:
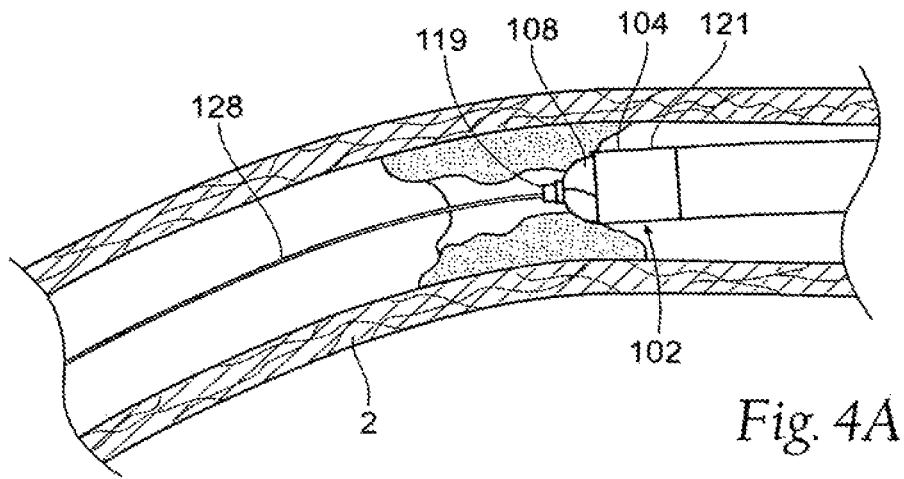
FIGS. 4A and 4B shows placement of features of the cutter assembly that prevent damage to the vessel walls.
Figure 4B:
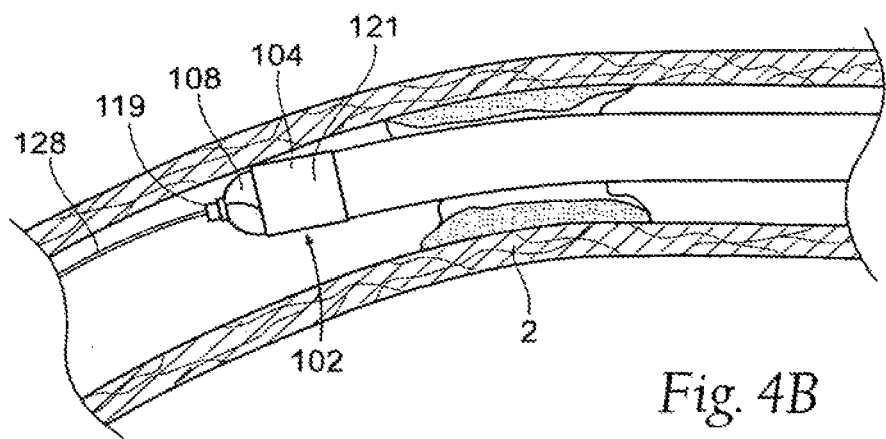

FIGS. 4A and 4B show a cutter assembly 102 adapted for forward cutting. This embodiment includes an open ended housing 104 where the cutter extends distally from the housing. However, a blunt bumper 119 at the distal tip of the cutter 108 acts as a buffer to prevent accidental cutting into the guidewire 128 or excessively into the lumen wall 2. In addition, this embodiment can optionally incorporate an additional housing portion 121 on a back end of the cutter assembly 102 that partially shields the cutter 108 from deep side cuts into the lumen wall 2.

Referring to FIG. 2A, a torque shaft 114 rotates inside the outer catheter body 120, sweep frame 250 and ferrule 116 to rotate the cutter and pull or aspirate tissue debris in a proximal direction. The clearance between the catheter body 120 and conveying member 118, as well as the pitch and thread depth of the conveying member 118, may be chosen to provide the desired pumping effectiveness, as will be described in greater detail later.

As seen in FIG. 2A, the ferrule 116 can have a distal bearing surface to bear against the proximal surface of the cutter 108 and keeps the cutter axially stable in the housing 104. In cases where the housing is stationary, the ferrule 116 can be rigidly bonded/linked to the housing 104 using solder, brazing, welding, adhesives (epoxy), swaging, crimped, press-fit, screwed on, snap-locked or otherwise affixed. As shown, the ferrule 116 can have holes or other rough features that allow for joining with the catheter body 120. While adhesives and heat fusing may be employed in the construction, such features are not required. Often adhesives are unreliable for a small surface contact and heat fusing can cause the catheter body 120 to degrade.

The use of a mechanical locking ring 126 allows the cutting assembly 102 to be short. Such a feature is important for maximizing the flexibility of the distal section 122 of the catheter 120 as it is required to navigate tortuousity in blood vessels. In one variation, a ring or band 126 can be swaged onto the catheter body 120 and over the ferrule 116. This drives portions of the ring/band as well as the catheter body into the openings of the ferrule 116 allowing for increased strength between the cutter assembly 102 and catheter body 120.

Figure 5A:
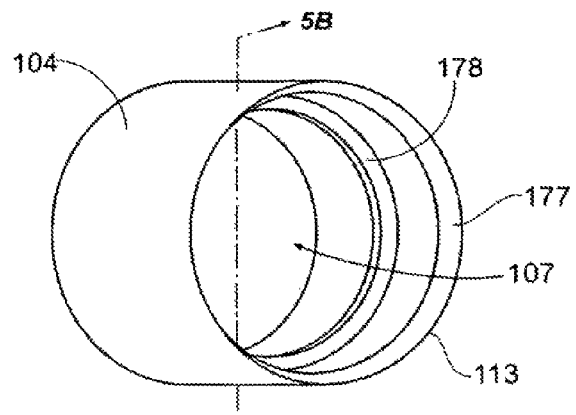
FIG. 5A shows a perspective view of a variation of an open ended cutter housing with an inner bevel.
Figure 5B:
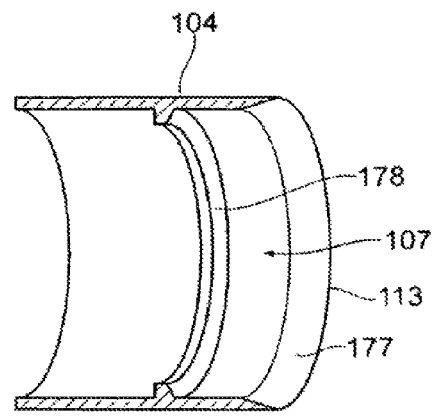
FIG. 5B shows a cross sectional side view of the open ended cutter of FIG. 5A taken along lines 5B-5B.

FIGS. 5A and 5B show a respective perspective view and cross-sectional side view of another variation of an open ended cutter housing 104. As shown, the cutter housing 104 includes an opening 107 located on a front face of a cylindrical housing 104. In this variation, the front edge 113 of the housing 104 can function as a front or forward cutting surface and has a beveled surface 177 on an inside surface of the housing 104. Such a beveled feature reduces the risk of the cutting surface 113 from driving into the wall of a vessel. As shown, some variations of the cutter housing 104 include a bearing surface 178 located within the housing 104. In an additional variation, to control the degree to which the cutting assembly 102 removes tissue, the distal end or cutting surface 177 of the housing 104 can be scalloped or serrated. For example, instead of being uniform, the cutting surface 177 can vary along a circumference of the housing in an axial direction (e.g., the serrated edges of the cutter extend along an axial length of the housing).

Figure 6A:
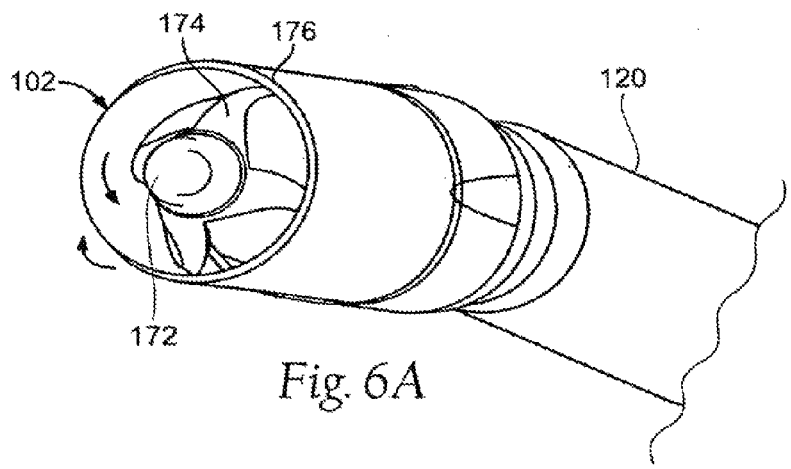
FIGS. 6A and 6B show variations of cutting assemblies for removing tissue from body lumens.
Figure 6B:
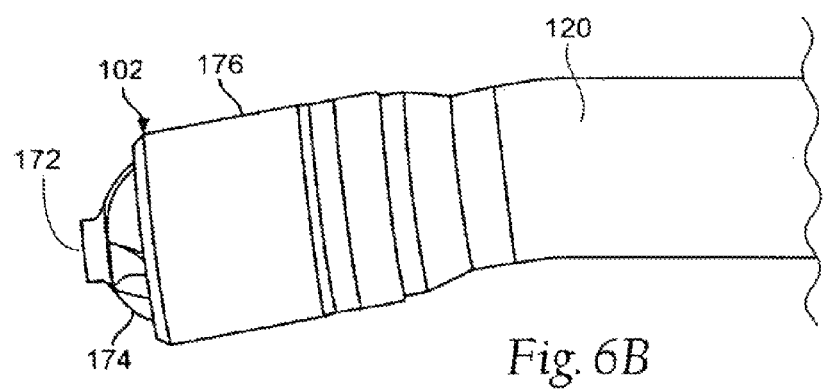
Figure 7A:
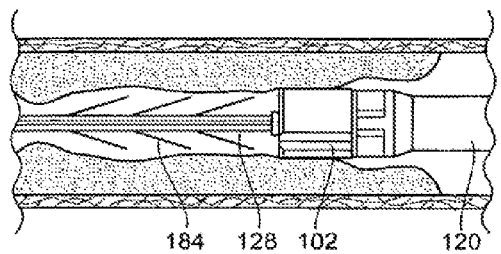
FIGS. 7A through 7F show additional variations for centering devices within a lumen.
Figure 7B:
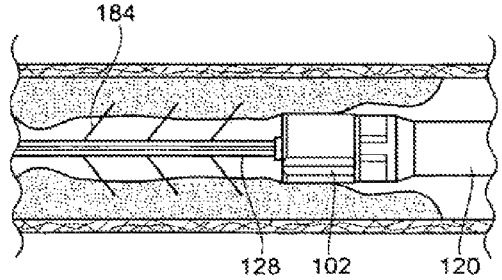
Figure 7C:
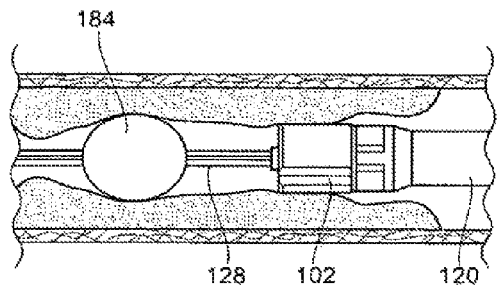
Figure 7D:
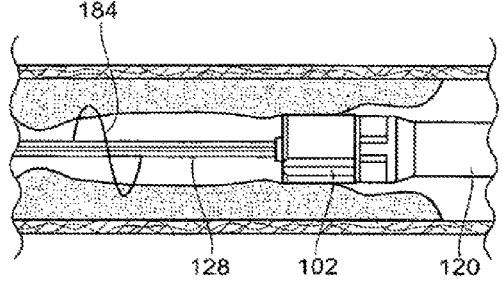
Figure 7E:
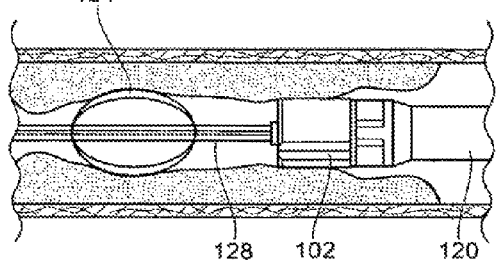
Figure 7F:
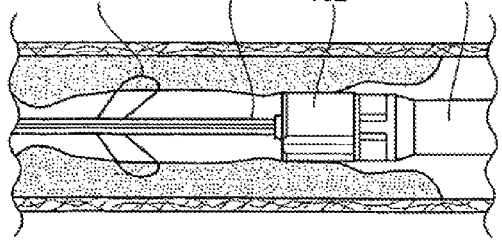

Additional variations of an open ended cutter assembly 102 comprise a spinning turbine-like coring cutter 172 is shown in FIGS. 6A and 6B. FIG. 6B shows a side view of the coring cutter 102. In use, the coring cutter can be hydraulically pushed to drive the sharp edge through tissue. The turbine like cutters 172 have helical blades 174 on the inside of the sharp cylinder housing 176.

An element of the coring cutter 102 may also have spokes or centering devices 184 as shown in FIGS. 7A to 7F to center the housing 104 about the guidewire. Optionally, the centering devices 184 may comprise an element of the guidewire 128, as shown. This helps to keep the cut of the plague centered about the vessel wall for safety. The spokes 184 also act as an impeller to pull stenotic tissue back and this helps to drive the cutter forward as well as achieve aspiration to minimize embolization.

2. Guarded Housing Cutter Assemblies a. Cutting Edge Configurations

Figure 8A:
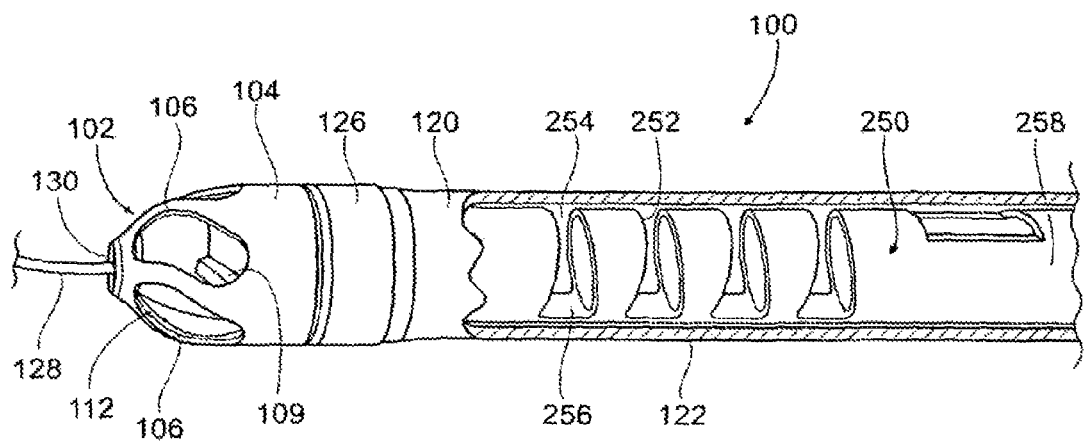
FIG. 8A is a perspective view in partial section of a distal portion of a system adapted for the removal of occluding material from body lumens, showing an embodiment of a sweep sheath.

FIG. 8A shows a variation of a tissue removal or debulking system 100 where the cutter assembly 102 is within a guarded housing 104. In this variation, the cutter assembly contains a first set of cutting edges 112 and a second set of cutting edges 109, where the first cutting edges 112 may extend along the entire length of the cutting assembly 102 (i.e., the entire length that is exposed in the openings 106 of the housing 104). In contrast, the second set of cutting edges 109 (in the figure only one such second cutting edge is visible) extend only along a portion. However, variations of the devices, systems, and methods described herein can include any number of cotter configurations as described herein or as known by those skilled in the art. Furthermore, although the illustrated system 100 shows a plurality of openings 106 in the housing 104, alternative cutting assemblies 102 can include a housing having a single opening on a distal face, as previously described.

Figure 8B:
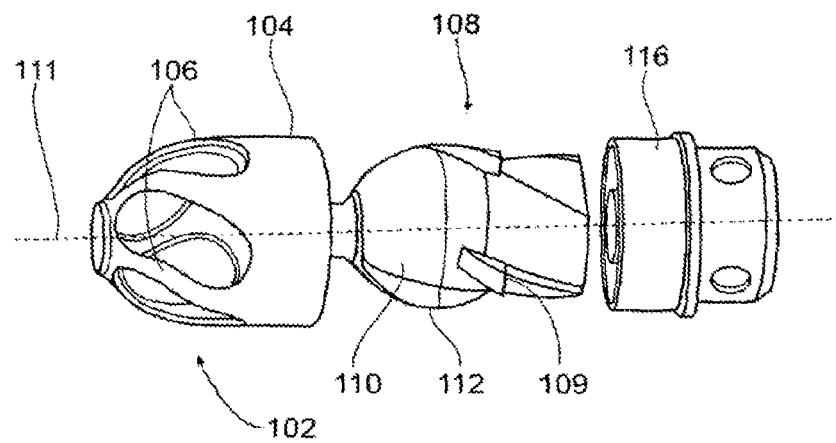
FIG. 8B is a perspective exploded view showing an additional embodiment of a cutting assembly with a one piece cutter.

FIG. 8B shows a variation of the cutting edges comprising a first set of cutting edges 112 that extend along (or substantially along) the cutter 108 and a second cutting edge 109 that extends only along a portion of the cutter 108. Although the number of cutting edges can vary, typically the cutting edges will be symmetric about an axis 111 of the cutter 108. For example, in one variation, the illustrated cutter 108 will have a pair of second cutting edges 109 symmetrically located about the cutter 108 and a pair of first cutting edges 112 symmetrically located about the axis 111 of the cutter 108. Accordingly, such a construction results in two cutting edges 112 located on a distal portion of the cutter 108 and four cutting edges 109 and 112 located on a proximal portion of the cutter 108.

Providing a cutter 108 with fewer cutting edges on a distal cutting portion and an increased number of cutting edges on a proximal cutting portion allows for a more aggressive cutting device. As shown, the cutter 108 can be configured with cutting edges 109, 112 that are adjacent to grooves, channels, or flutes 110 (where the combination is referred to as a "cutting flute"). The cutting flute 110 provides a path for the cut material to egress from the treatment site through the system 100, and improves the impelling force generated by the cutter 108. The helical flutes 110 and sharp cutting edges 112 may be parallel to each other and may be wound from proximal to distal in the same sense as the rotation of the cutter. When the cutter 108 rotates, it becomes an impeller causing tissue debris to move proximally for evacuation.

By reducing the number of flutes on the distal portion of the cutter, the flutes can be made deeper. The deeper flutes allow the cutting edge adjacent to the flute to remove greater amounts of material. However, increasing the size of the material can also increase the chances that the material becomes stuck or moves slowly through the catheter 120 during removal. To alleviate this potential problem and increase the efficiency of transporting the material through the catheter, the cutter can be configured with an increased number of cutting edges towards a rear of the cutter that reduce the size of the cut material by providing a second cut of the material to further reduce the material size for improved transportation.

By controlling the number of cutting edges 109, 112 that are exposed through openings 106 in the housing 104, it is possible to control the relative amount of cutting engagement (both length of cutting and depth of cut, together which control the volume of material removed per unit rotation of the cutter). These features allow independent control of the maximum torque load imposed on the system 100. By carefully selecting the geometry of the flutes and or cutting edges 112 relative to the openings 106 in the housing 104, it is possible to further control the balance of torque. For example, the torque load imposed on the system is caused by the shearing of tissue when the cutter edge 112 and/or 109 is exposed by passing through the housing window 106. If all cutter edges simultaneously shear, as for example when the number of housing windows is an even multiple of cutter edges, the torque varies cyclically with rotation of the cutter. By adjusting the number of cutters and windows so one is not an even multiple of the other (for example, by using five windows 106 on the housing and four cutting edges on the cutter 108), it is possible to have a more uniform torque (tissue removal from shearing action) during each rotational cycle of the cutter 108. It is to be appreciated that the cutting edge configurations described above are available for all cutter assembly embodiments described herein.

The geometry of the cutter 108 and housing 104 can be used to tailor the desired degree of cutting. The housing 104 and orientation of the openings 106 can be used to limit the depth of cutting by the cutter 108. In addition, the distal end of the housing 104 may be domed shaped while the proximal end may have a cylindrical or other shape. For example, by creating larger apertures or windows 106 in the housing, a larger portion of cutter 108 may be exposed and the rate of cutting increased (for a given rotation speed). By placing the cutting window 106 on a convex portion or side wall 105 of the housing 104, the debulking effectiveness is much less sensitive to the alignment of the cutter housing 104 to the lesion, than if the window 106 were on the cylindrical portion of the housing. This is a key performance limitation of traditional directional atherectomy catheters. In addition, placement of the window 106 on the convex portion of the housing creates a secant effect (as described below).

b. Cutter Assembly Configurations

Figure 9:
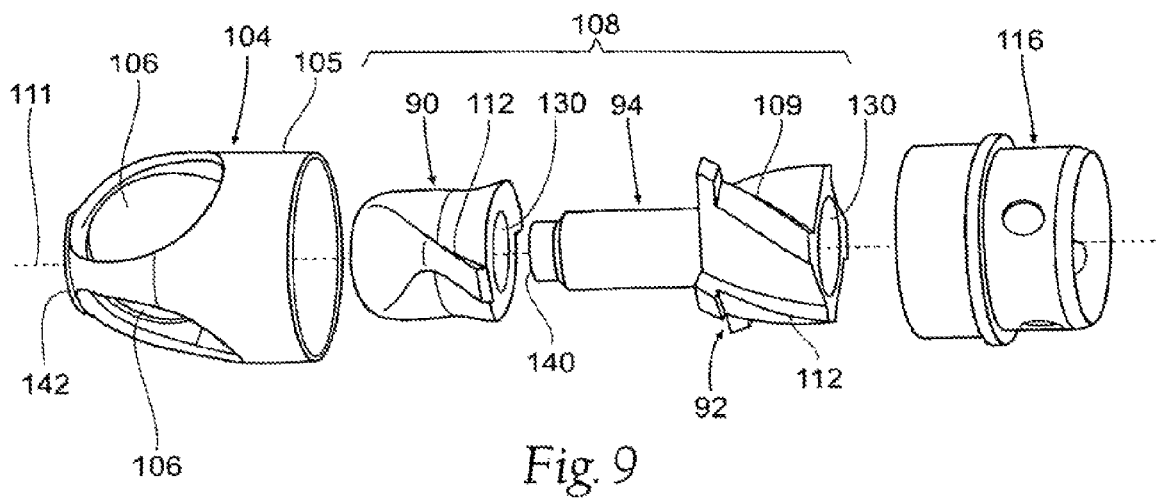
FIG. 9 is a perspective exploded view showing an additional embodiment of a cutting assembly with a two piece cutter.

FIG. 9 illustrates an exploded view of a cutter assembly 102 and ferrule 116. In this variation, the cutter assembly 102 includes a housing 104 having three openings 106 symmetrically placed about a sidewall 105 of the housing. FIG. 9 also shows an embodiment of cutter 108 that comprises a distal portion 90 mounted on a proximal portion 92 (where the proximal cutter portion 92 can also be referred to as a cutter core adapter). The proximal cutter portion 92 contains a shaft 94 terminating in a mating piece 140 for coupling the cutter 108 to the housing 104 (where the mating piece 140 nests within a center lumen 142 in a front face of the housing 104. The cutter 108 can also include a passage 130 for passing of a guidewire through the system 100.

Although the inventive system 100 includes embodiments of cutters formed from in a unitary body, providing the cutter 108 with distal and proximal 90, 92 cutter portions allows for optimal selection of materials. In addition, as shown, a first cutting edge 112 can extend along both cutter portions 90, 92 while a secondary cutting edge 109 may extend only along the proximal cutter portion 92. Given this configuration, when the cutter portions 90, 92 join to form the cutter 108, the distal portion 90 of the cutter only contains two fluted cutting edges while the proximal cutting portion 92 includes four fluted cutting edges. Naturally, any number of fluted cutting portions are within the scope of the invention. However, variations include fewer cutting edges on a distal end of the cutter 108 relative to the number of cutting edges on a proximal end of the cutter 108. Moreover, the cutting edges may or may not be symmetrically located about the cutter.

Figure 10:
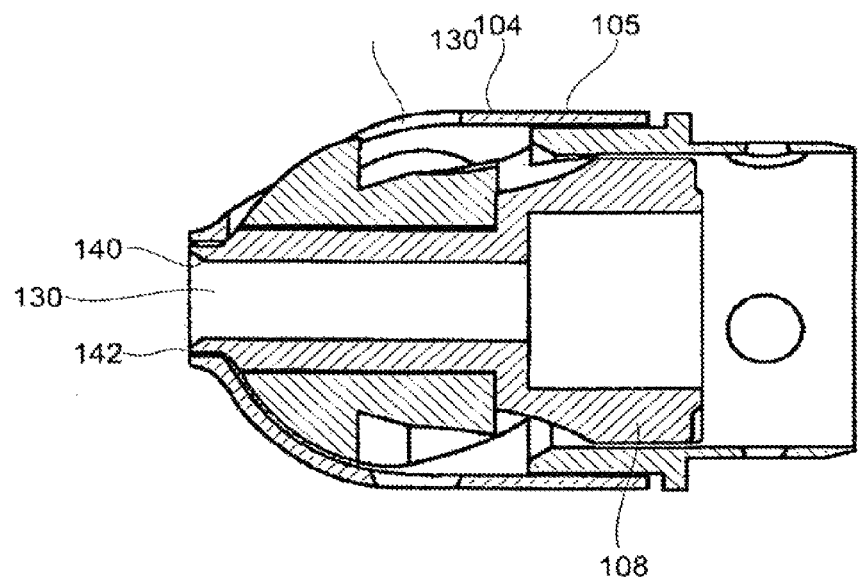
FIG. 10 shows a cross sectional view of the cutting assembly shown in FIG. 8A.
Figure 11:
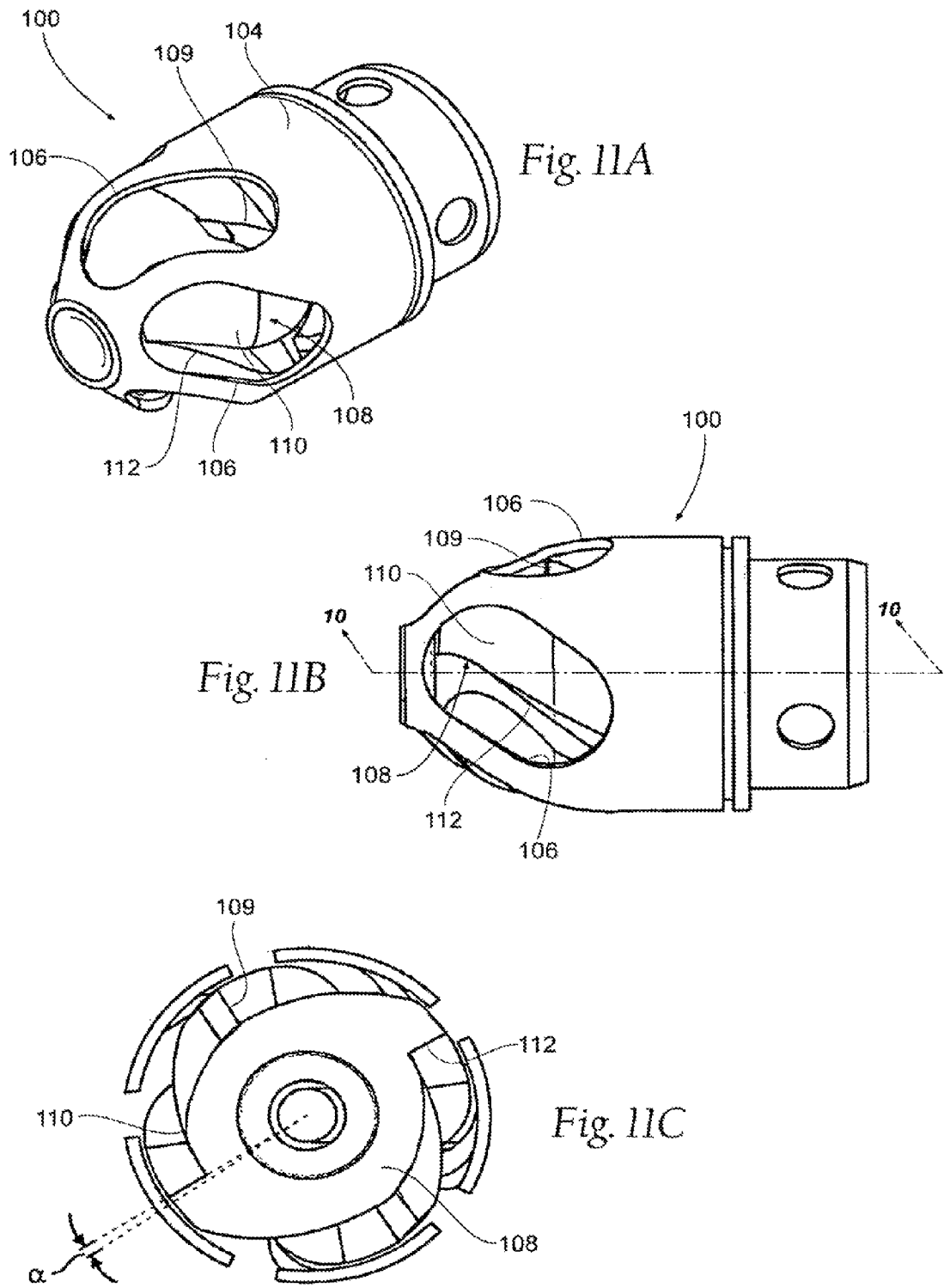
FIG. 11A shows the cutting edges through openings of a housing.
FIG. 11B shows a side view of the cutting assembly of FIG. 11A.
FIG. 11C shows a front view of the cutting assembly of FIG. 11A, and showing a positive rake angle.

FIG. 10 shows the housing 104 having a distal nose with the center lumen 142 for receiving the mating piece 140 of the cutter 108. Such features assist in centering the cutter 104 concentrically inside the housing 104. As described below, variations of the cutter assembly 102 include the addition of a burr element for grinding hard tissue such as calcified plaque of a dilator member for separating materials towards the openings 106.

FIGS. 11A through 15 show various additional examples of cutting assemblies 102 including a guarded housing 104, and that can be incorporated with the system 100.

FIG. 11A illustrates the cutting assembly shown in FIGS. 8A, 8B, and 9 where the openings 106 form helical slots in the housing 104. The openings 106 may or may not be aligned with the cutting edges 109, 112 of the cutter 108. For aggressive cutting, the slots 106 and cutting edges 109, 112 can be aligned to maximize exposure of the tissue to cutting edges. In other words, the cutting edges 109, 112 and openings 106 can be in alignment so all cutting edges 109, 112 are exposed at the same time to allow simultaneous cutting. Alternatively, alignment of the openings and edges 109, 112 may be configured so that fewer than all the cutting edges 109, 112 are exposed at the same time. For example, the alignment may be such that when one cutting edge is exposed by an opening 106, the remaining cutting edges are shielded within the housing 104. Variations of such a configuration allow for any number of cutting edges to be exposed at any given time. In addition, the variation depicted in FIG. 11A shows a window or opening 106 large enough to expose both the first 112 and second 109 cutting edges. However, in alternate variations, the windows can be configured to only expose the cutting edges 112 on the distal end of the cutter 108.

In another variation adapted to even out the torque profile of the device when cutting, the cutter 108 can be configured such that the number edges/cutting surfaces 109, 112 of the flutes 110 that are aligned with the housing openings 106 does not vary throughout the rotational cycle. This prevents the catheter from being overloaded with torque spikes and cyclic torque variations due to multiple cutting edges/flutes engaging with tissue in synchrony. In other words, the length of the cutting surface 112 exposed through the openings 106 of the housing 104 remains the same or constant.

In the variation shown in FIG. 11B, the cutting edges 109, 112 are configured to capture debris within the flute 110 as the cutter 108 rotates. Typically, the cutter 108 may be designed with a secant effect. This effect allows for a positive tissue engagement by the cutter 108. As the cutter 108 rotates through the opening, the cutting edge moves through an arc where at the peak of the arc the cutting edge protrudes slightly above a plane of the opening 106. The amount of positive tissue engagement can be controlled through selection of the protrusion distance through appropriate design of the housing geometry (for example, by a combination of location and size of the window 106 and radius of curvature of the housing 104). The cutting edge 109 or 112 can extend out of the housing 104 through the window 106 as it rotates. This structure can also be designed to drive or impel the debris to the conveying member 118 (see FIG. 2A). In this case, the flutes 110 within the cutter 108 are helically slotted to remain in fluid communication with the conveying member 118.

FIGS. 11A and 11B also show a surface of the cutter 108 having a curved-in profile distally and is close to the housing 104 surface. Note that housing openings 106 with this curved profile allows the cutting edge 112 to protrude beyond the housing's outer surface. In other words, the openings 106 form a secant on the curved surface of the housing 104. Such a feature allows improved cutting of harder/stiffer material like calcified or stiff fibrous tissue where such tissue does not protrude into the housing 104.

As shown in FIG. 11C, variations of the cutter 108 may have cutting edges 109, 112 with positive rake angles α—i.e., the cutting edge is pointed in the same direction as that of the cutter rotation. This configuration maximizes the effectiveness of the impelling and cutting action (by biting into tissue and avoiding tissue deflection).

Figure 12:
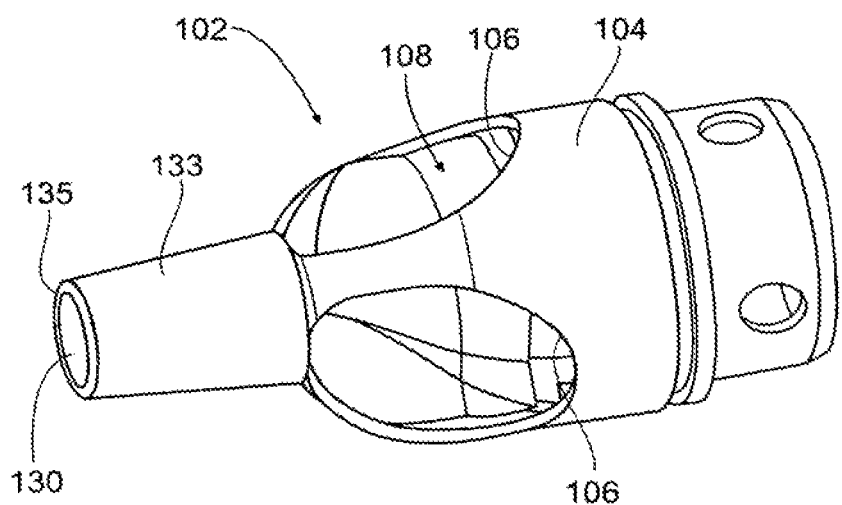
FIG. 12 is a perspective view of an embodiment of a guarded housing having a dilation member.

FIG. 12 shows a variation of a cutter assembly 102 where a housing 104 of the cutter assembly 102 includes m conical, tapered, or dilator extension 133 extending from a front face of the housing 104. The dilator extension 133 is adapted to serve a number of purposes, namely that it can help prevent the cutting assembly 102 from damaging a vessel wall. In addition, the added structural reinforcement of the front face of the housing 104 reduces the chance that the rotating cutter 108 actually cuts through the housing 104 if the struts were to deflect inward. However, one important feature of the dilator extension 133 is that it provides a tapered surface from a guidewire to the openings 106 in the housing 104. Accordingly, as the dilator extension 133 advances through occlusive material, the dilator extension 133 forces or dilates material away from a guidewire towards the openings 106 and cutting edges. In order to dilate material away from a center of the cutter assembly 102, the dilator extension 133 must have sufficient radial strength. In one example, the dilator extension 133 and housing 104 can be fabricated from a single piece of material as discussed herein.

The dilator extension 133 typically includes an opening 130 for passage of a guidewire. In addition, in most variations, a front end 135 of the dilator extension 133 will be rounded to assist in moving the occlusive material over a surface of the dilator 133. Furthermore, the surface of the dilator extension 133 can be smooth to permit sweeping of the cutting assembly 102 as discussed below. Alternatively, the dilator extension 133 can have a number of longitudinal grooves to direct material into the openings 106. In additional variations, the dilator extension 133 may not include an opening 130. In such a case, the dilator extension 133 may fully taper to a closed tip.

Figure 13A:
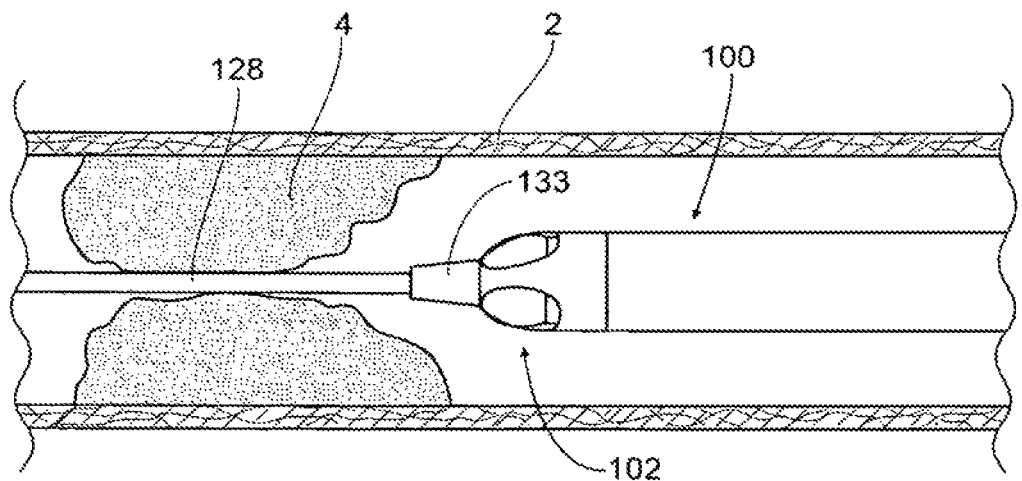
FIGS. 13A through 13C are side views showing the use of a debulking device having a dilating member as seen in FIG. 12.
Figure 13B:
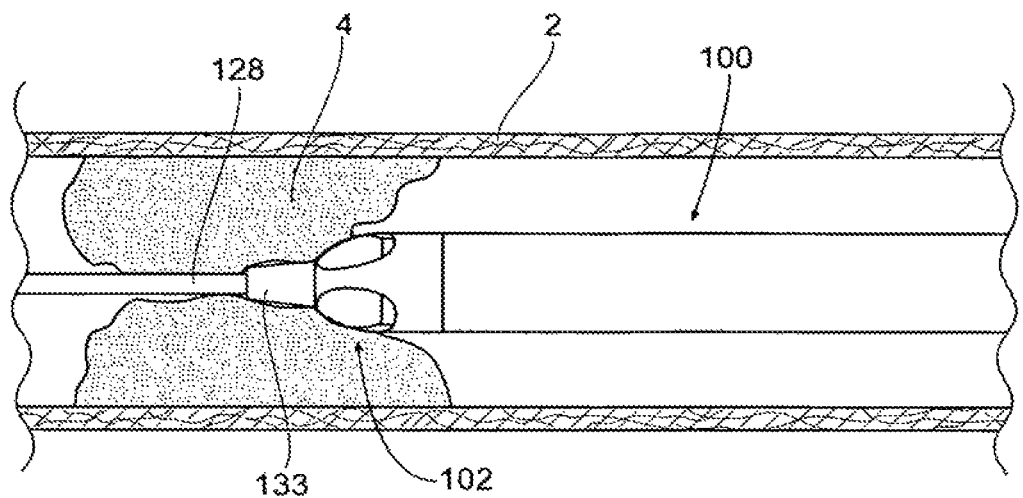
Figure 13C:
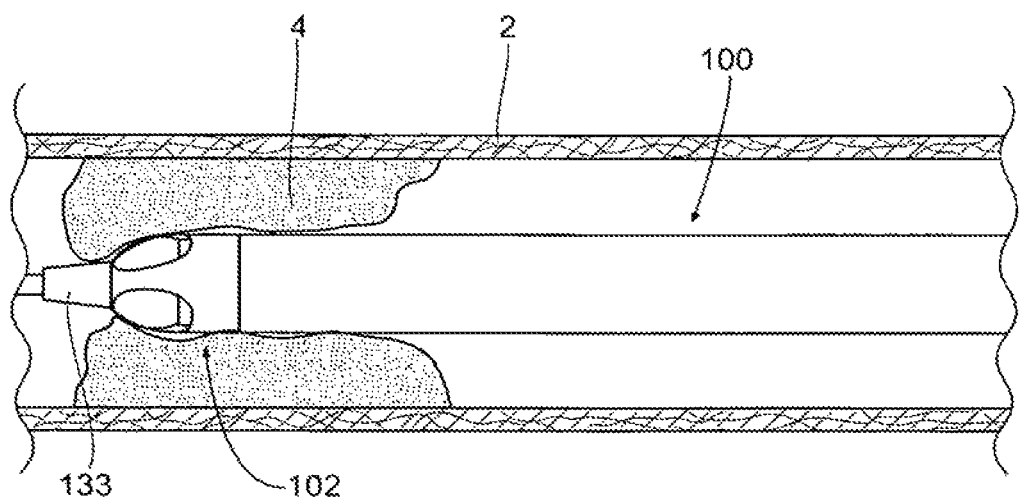

FIGS. 13A to 13C show use of a system 100 incorporating a dilating member 133. In this variation, the device 100 is advanced over a guidewire 128. However, use of a guidewire 128 is optional. As the device 100 approaches the plague or occlusive material 4, the dilating member 133 forces the plaque 4 away from a center of the system 100 and towards openings 106 in the cutting assembly 102 as shown in FIG. 13B. Clearly, the dilating member 133 must have sufficiently radial strength so that it forces the obstruction towards the openings 106. However, in those variations where the dilating member 133 is conical or tapered, the plaque material 4 is gradually moved towards the openings 106. In those devices not having a dilating member 133, the physician must apply excessive force to move the cutter against the plaque 4. In some excessive cases not incorporating a dilating member 133, the cutter may be able to shear through a cutter housing leading to failure of the device.

FIG. 13C illustrates a situation where the system 100 traverses the entire occlusion 4. However, as described in detail later, the device may be configured for sweeping within the vessel. As such, the physician may choose to sweep the system 100 within the occlusion to open the occlusion during traversal of the occlusion or after a path is created through the occlusion. In either case, the nature of the dilation member 133 also functions to keep the cutting assembly 102 spaced apart from a wall of the vessel 2.

Figure 14A:
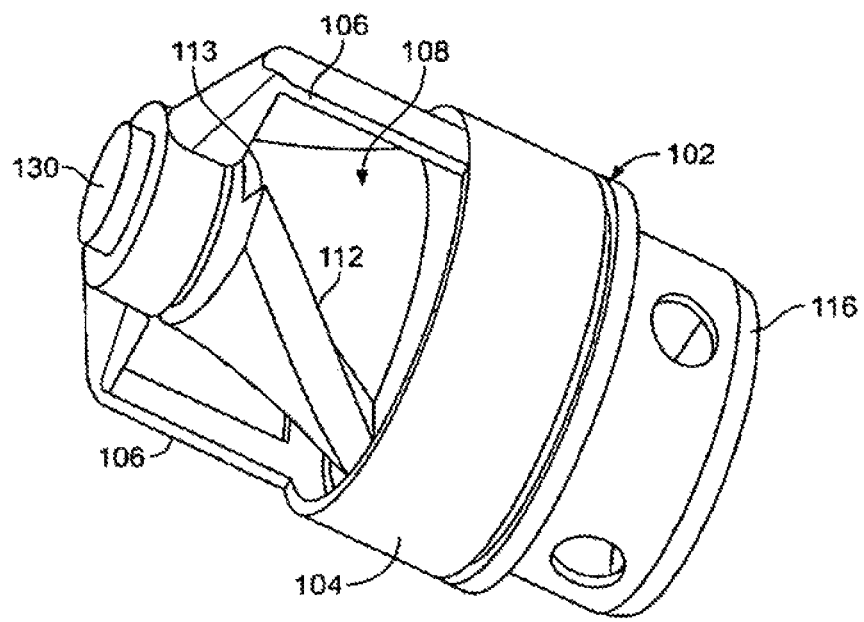
FIGS. 14A and 14B show an additional embodiment of a shielded cutter having a plurality of front cutting surfaces and fluted cutting surfaces.
Figure 14B:
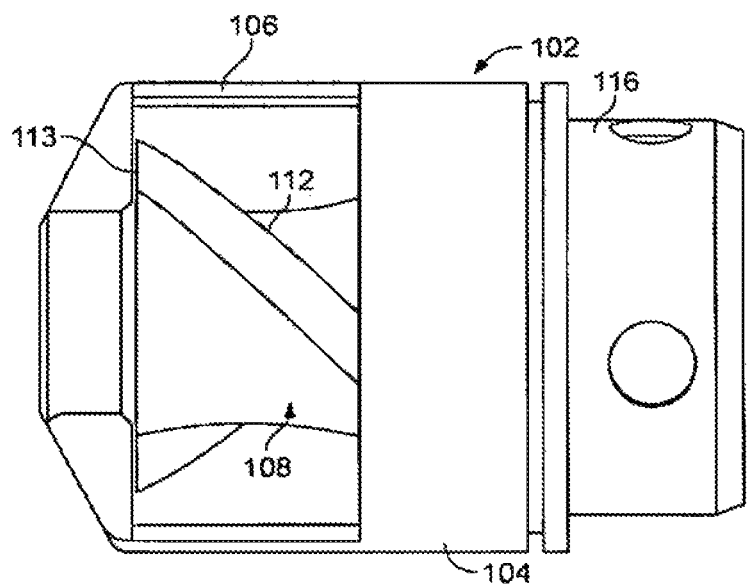

FIGS. 14A and 14B show another variation of a cutter assembly 102 having a forward cutting surface 113 on a distal portion of the cutter 108. In this variation, the cutter housing 104 may include two or more large openings 106 that allow the forward cutting surface 113 to engage tissue when moved in a distal direction. The cutter 108 may also include a plurality of fluted cutting edges 112.

Figure 15:
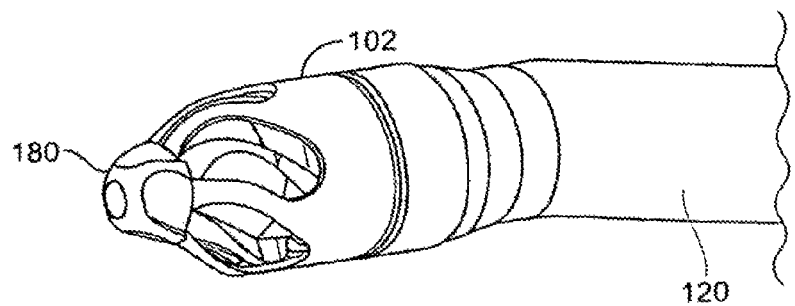
FIG. 15 is a perspective view of a cutting assembly having a guarded housing and incorporating a burr tip.

As shown in FIG. 15, a cutter assembly 102 can also have a burr 180 protruding from its distal portion. Although the burr 180 may have any type of abrasive surface, in one variation, this burr 180 is blunt and has fine grit (such as diamond grit) to allow for grinding of heavily calcified tissue without injuring adjacent soft tissue. This combination of a burr 180 and cutter 108 allow the cutter assembly 102 to remove hard stenotic tissue (e.g., calcified plaque) using the burr 180 while the sharp-edged shaving cutter 108 removes softer tissue such as fibrous, fatty tissue, smooth muscle proliferation, or thrombus. In variations, the burr 180 can also have helical flutes to help with aspiration, or the burr can be incorporated into a portion of the cutting edge (for example, the most distal aspect of the cutter 108).

c. Distal and Proximal Cutting

Figure 16A:
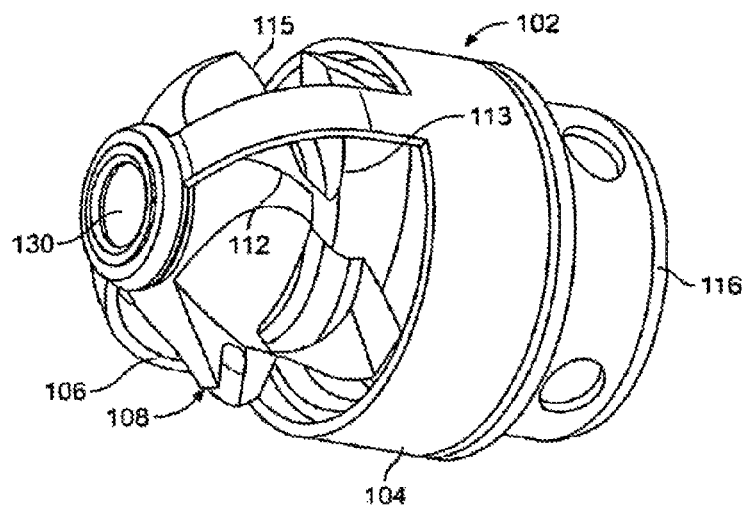
FIGS. 16A and 16B show a variation of a shielded cutter having a plurality of front cutting surfaces, rear cutting surfaces, and fluted cutting surfaces.
Figure 16B:
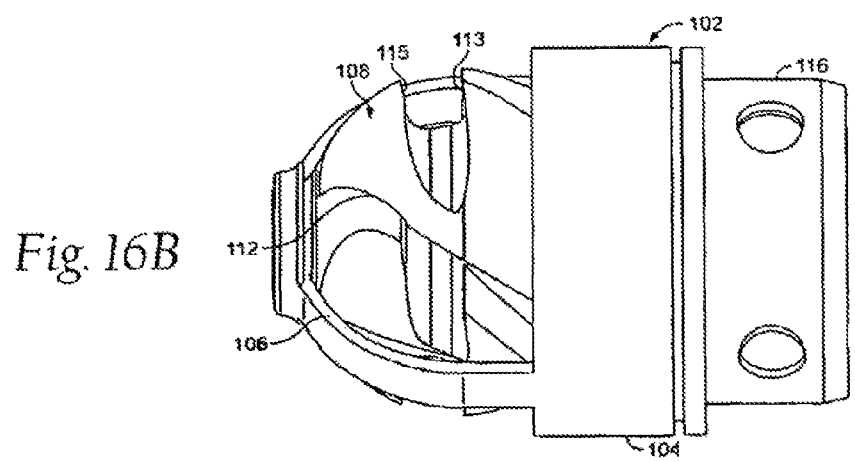

FIGS. 16A and 16B show an additional variation of a cutting assembly 102 adapted for use with the system 100. FIG. 16B shows a side view of the cutter assembly 102 of FIG. 16A. In this embodiment, the cutting assembly 102 includes larger windows 106 to accommodate a cutter 108 that includes a plurality of directional cutting surfaces 112, 113, and 115. As the cutter 108 rotates within the housing 104, the fluted cutting edge 112 cuts in a direction that is tangential to a rotational direction of the cutter 108. In other words, the fluted cutting edges 112 cut material that is about the perimeter of the cutter 108 as it spins. The cutter 108 also includes on or more forward and rearward cutting surfaces 113, 115. These cutting surfaces 113, 115 engage tissue when the catheter is run in a forward direction or rearward direction. The ability to engage and remove tissue in multiple directions have been shown to be important for effective debulking. However, a variation of a cutter 108 in the present invention can include a cutter 108 with one of two directional cutting surfaces. For example, the fluted cutting edges 112 can be combined with either the forward 113 or rearward 115 cutting surfaces. The ability to debulk in a forward, rearward, and rotational directions also reduces the chance that the cutter assembly deflects from stubborn or hard tissue.

B. The Catheter Assembly

1. Catheter Body

Figure 17:
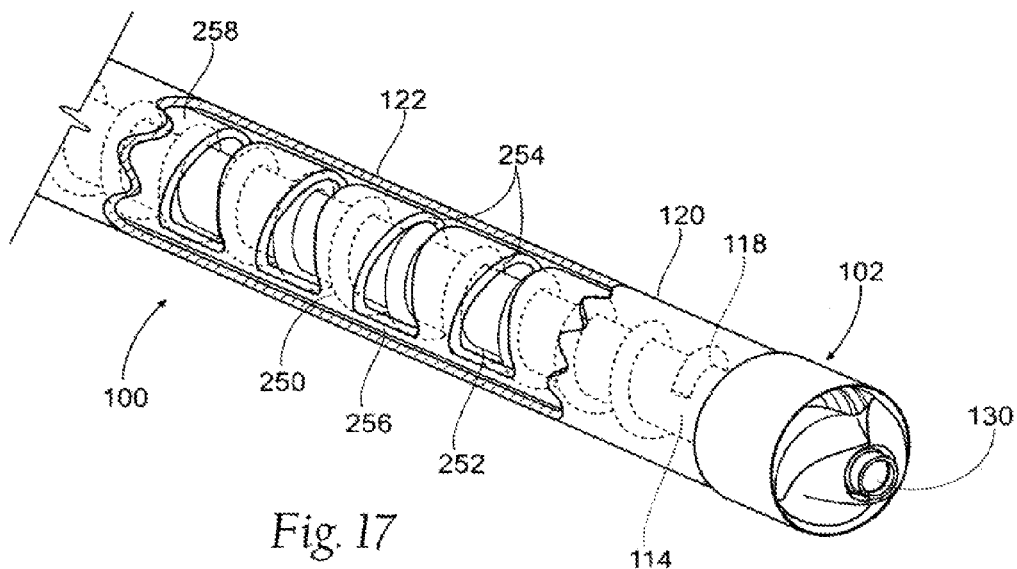
FIG. 17 is a perspective view in partial section of a distal portion of a system adapted for the removal of occluding material from body lumens, showing the catheter body, a sweep sheath, a torque shaft, and a conveying member.

FIG. 17 shows the distal portion 122 of the atherectomy system 100 having a cutter assembly 102 extending from the catheter body 120. As will be discussed below, the catheter body 120 can be coupled to a rotating mechanism or motor 150, desirably in the handle 200, which ultimately drives the cutter assembly 102 via a torque shaft 114.

In general, for proper debulking of tissue within vessels, the system 100 desirably includes a catheter 120 that is able to support the cutter assembly 102 with sufficient apposition force (bending stiffness). The catheter body 120 should be torqueable enough (i.e., have sufficient torsional stiffness) so that the physician can point the cutter assembly 102 to the desired angular position within the vessel 2. The system 100 should also be pushable enough (i.e., have sufficient column stiffness) to allow proper cutting as the physician advances the device through tissue. However, these needs must be balanced against making a device that is too stiff to reliably access tortuous or angled anatomy. In order to balance these requirements, a variation of the system 100 can have a more flexible distal tip location 122 (e.g., within the last 10 cm as a non-limiting example) to improve the navigation (including trackability over a guidewire, for example) in tortuous anatomy. Because the overall stiffness (in compression and torque) depends upon the full length of the catheter 120, but navigation is influenced mainly by the distal tip region 122, this method is one way to optimize several variables at the same time.

An additional design for increased torque and push is to construct the catheter body 120 and/or sweep member 270 (to be discussed in greater detail below) from a braid over a wound coil, with an optional polymeric jacket covering. This composite construction may be over a polymer liner made of a material such as PTFE. Yet another variation includes a catheter body 120 and/or sweep member fabricated from a metal tube having selective cuts along the length of the tube (e.g., stainless steel or nitinol) to create the desired profile of stiffness (bending, torsion, and compression) along the length of the catheter 120. This slotted metal tube can be lined or jacketed with polymeric material, and further may be treated to produce hydrophilic, hydrophobic, or drug binding (heparin, antimicrobial) properties. The configurations described herein apply to any debulking device described herein.

The catheter body 120 may also be composed of a reinforced sheath, such as a metal braid sandwiched in a polymeric matrix of such materials as high density polyethylene (HDPE), polyethylene (PE), fluoro-polymer (PTFE), nylon, polyether-block amide (PEBAX), polyurethane, and/or silicone. The sheath is stiffer proximally than distally. This can be achieved by using softer grades of polymers distally and/or having no metal braid distally.

Figure 18A:
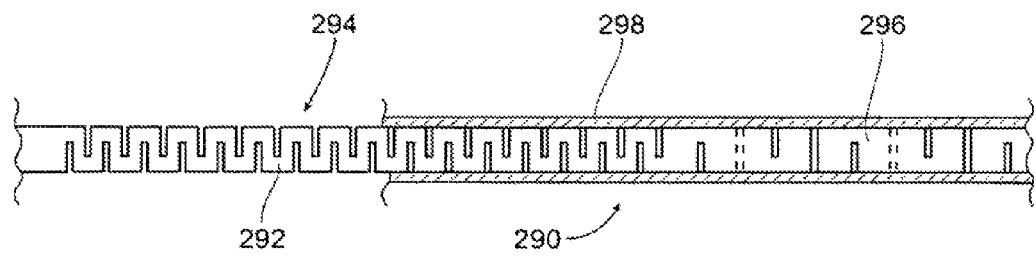
FIGS. 18A and 18B show additional possible variations a catheter body or sweep member.

FIGS. 18A through 18F illustrate possible variations of a composite construction that can be employed in fabricating either a catheter body 120 and/or a sweep member 270 for use in the debulking systems described herein. FIG. 18A shows a composite construction 290 of a slotted tube 292, where the tube can be selected from e.g., a polymer, a metal—such as stainless steel, or a shape memory alloy—such as a super-elastic Nitinol tube, or a combination therein. The pattern of slots along the tube 292 can be tailored to achieve the desired properties such as graded stiffness along the long axis and/or the short axis of the catheter body 120. The construction 290 can optionally include polymeric coatings, sleeves, or liners 298 in the inner and/or outer surfaces of the tube 292.

FIG. 18A also shows a tube 292 as having a first region 294 and a second region 296 where the frequency of the slots varies between regions. Any number of slotted tube configurations, such as those found in medical devices designed for navigation to tortuous areas, can be employed in the designs herein. Such designs, when combined in atherectomy—debulking catheters with sweep frames as described herein, provide significant and unexpected improvements in steering and cutting of lesions.

Figure 18B:
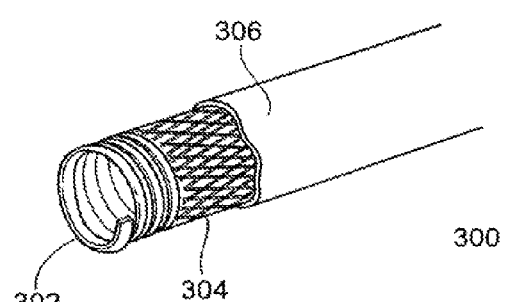

FIG. 18B illustrates another variation of a composite construction 300 that can be employed in a catheter body 120 and/or a sweep member 270 for use with variations of the debulking systems 100 described herein. As illustrated, the construction 300 includes a coil member 302 covered by a braid 304. The coil and braid can each be fabricated from any material commonly known in the field of braided/coiled catheters. For example, the coil 302 can be wound from a superelastic wire or ribbon. While the braid can comprise a plurality of super elastic or stainless steel filaments braided or woven together. FIG. 18B also shows the braid 304 covered by a polymeric coating, sleeve, or liner 306.

In an additional variation, the catheter body 120 and/or sweep member 270 can comprise a spiral cut tube covered by a liner or polymeric layer. In such a case, the angle of the spiral as well as the width can be selected to impart desired characteristics on the device. For example, the spiral can be selected to maximize pushability of the device while maintaining a near one-to-one relationship between the cutting assembly 102 and proximal end of the device when rotating or sweeping the cutting assembly.

Figure 18C:
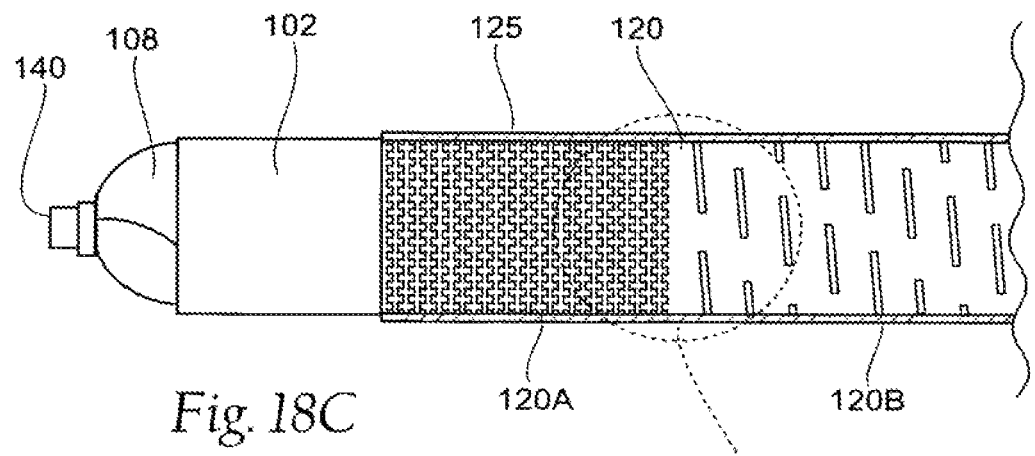
FIG. 18C is a side view of an alternative embodiment of a catheter body including a multi-body design having minimal torsional losses while maximizing bending in a first portion and longitudinal stiffness in a second portion.

FIG. 18C shows yet another variation of a catheter body 120 and/or a sweep member 270 for use with variations of the debulking systems 100 described herein. As can be seen, the catheter body 120 may include a multi-body design having minimal torsional losses while maximizing bending in a first portion 120A and longitudinal stiffness in a second portion 120B. The first portion 120A is shown having a dovetail construction adapted for predefined expansion between the dovetail features, providing for controlled flexibility. The second portion 120B is shown having a helical cut pattern creating a line-to-line fit of supports, which creates a helical series of uninterrupted material to maintain bending-free transmission of torsional tensile and compressive loads. This embodiment may also include an elastic outer or inner sheath or jacket 125 adapted to elastically constrain the dovetailed components from axially expanding, but allowing the distal portion 120A to radially flex.

Figure 18D:
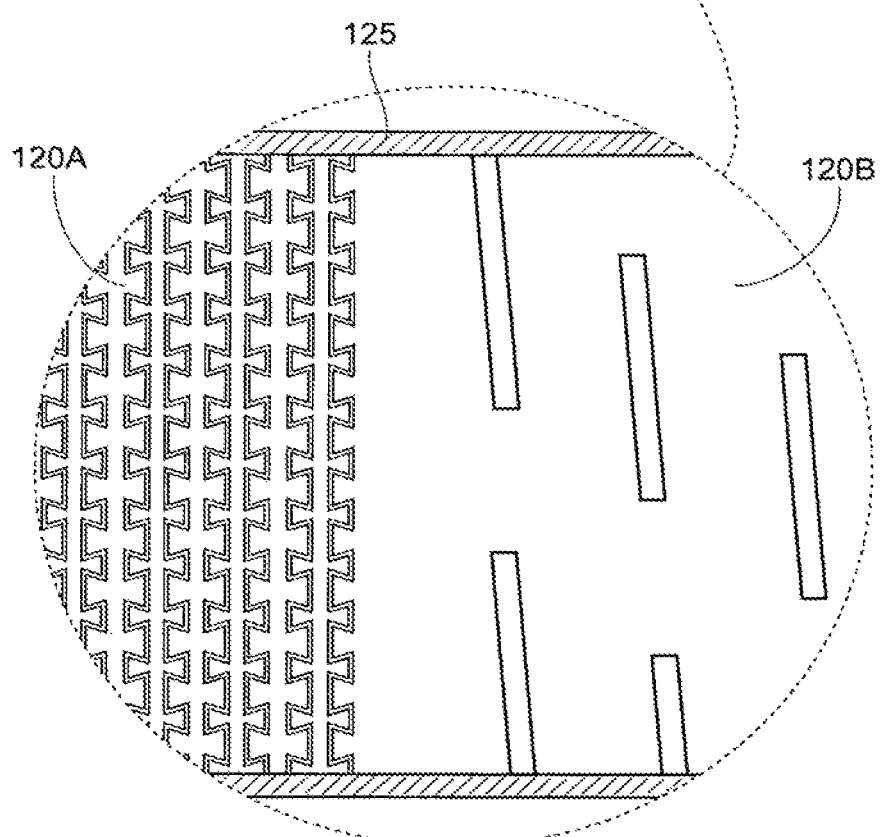
FIG. 18D is a detail view of the first and second section of FIG. 18C, showing one embodiment of a dovetail design for the first section.
Figure 18E:
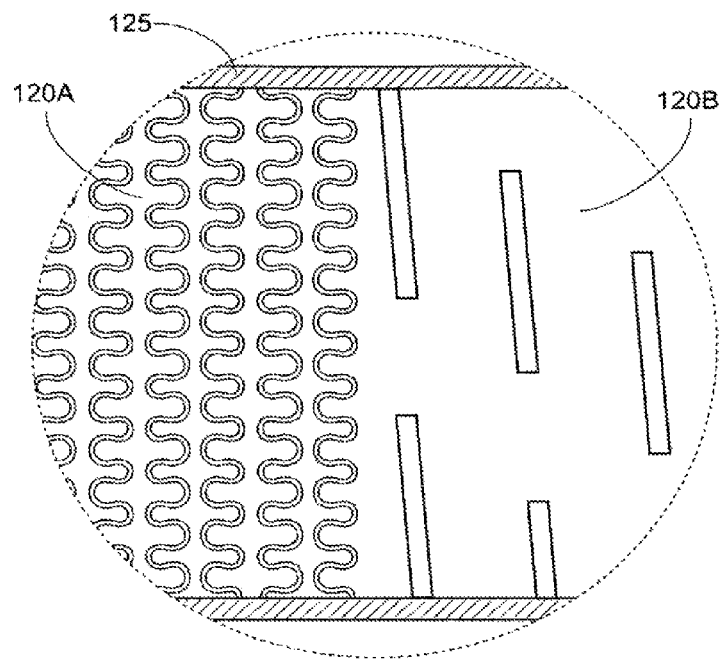
FIG. 18E is a detail view of an alternative embodiment of the first section of FIG. 18C, showing an additional embodiment of a dovetail design for the first section.
Figure 18F:
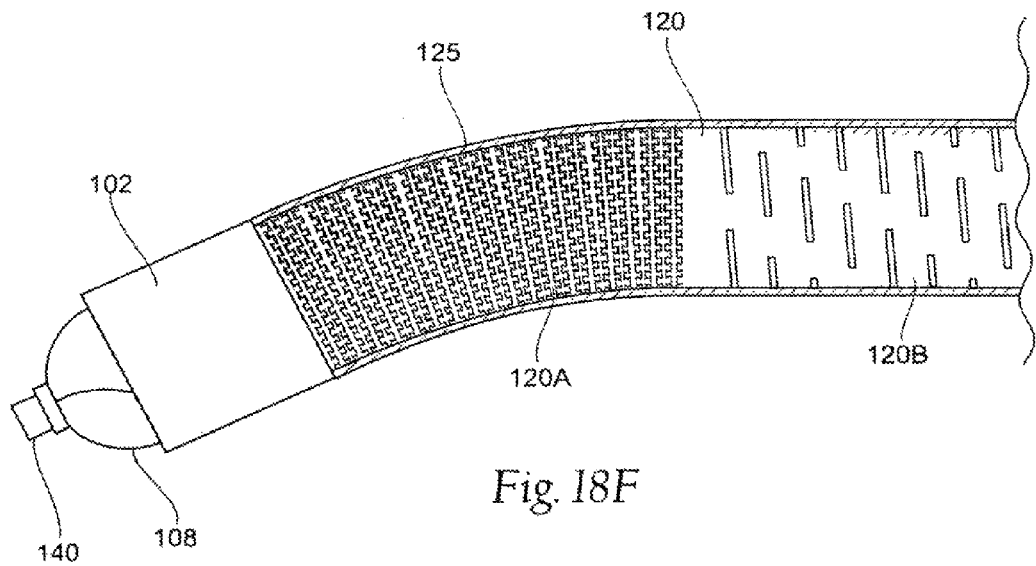
FIG. 18F is a side view of the catheter body including a multi-body design of FIG. 18C, showing a flexed distal portion.

FIGS. 18D and 18E show detailed views of embodiments of the first and second portions 120A and 120B, showing optional configurations of a dovetail feature, with FIG. 18D showing a traditional dovetail construction, and FIG. 18E showing a serpentine configuration. It is to be appreciated that other configurations are also possible. FIG. 18F shows the catheter body 120 in a radially flexed position, showing the bending of the first portion 120A through the arced expansion of the dovetailed configuration.

Coatings can be applied to the moving components in the catheter 120 to reduce friction. In one embodiment, the catheter 120 and the torque shaft 114 are coated with a hydrophilic coating (polyvinyl alcohol) to reduce friction between the moving components in the catheter 120. The coatings can also be hydrophobic (e.g. parylene, PTFE). The coatings can be impregnated with heparin to reduce blood clotting on surface during use.

2. Torque Shaft and Conveyer Member

Figure 19A:
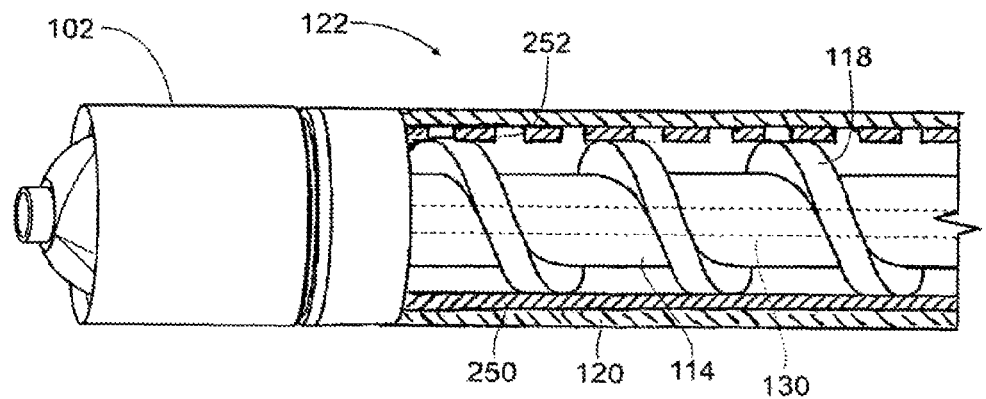
FIG. 19A shows a conveying member within the catheter body and sweep frame.
Figure 19B:
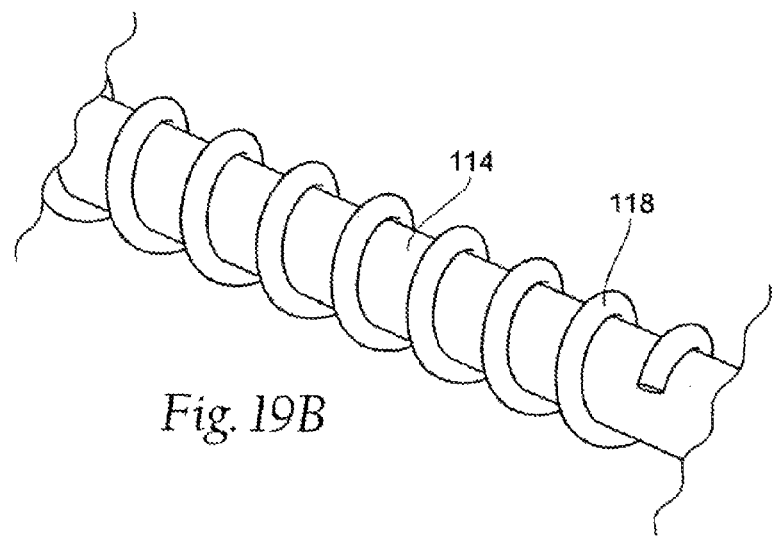
FIG. 19B shows an embodiment of a conveying member wound around the torque shaft, as seen in FIG. 17.

FIG. 19A illustrates a partial cross-sectional view of a variation of the distal portion 122 of the system 100 showing the placement of the torque shaft 114 within the catheter body 120 and sweep frame 250. As shown, this variation of the system 100 includes a conveyor member 118 located within the catheter body 120 and on an exterior surface of the torque shaft 114. The conveyor member 118 may be an auger type system or an Archimedes-type screw that conveys the debris and material generated during the procedure away from the operative site. In any case, the conveying member 118 may have a raised surface or blade that drives materials in a proximal direction away from the operative site (see FIG. 19B). Such materials may be conveyed to a receptacle outside of the body or such materials may be stored within the system 100. The torque shaft 114 and conveying member 118 may extend along the full length of the catheter and possibly into the handle 200, or the conveying member may extend only along a portion of the length of the catheter 120. As shown, the torque shaft 114 and conveyor 118 fit within the sweep frame 250. In some variations of the system 100, a cover or film can be placed between the sweep frame 250 and torque shaft 114 to prevent debris from becoming trapped within the serrations, slots or openings 252 of the sweep frame 250. The cover or film may also act as a smooth, low friction surface.

Figure 19C:
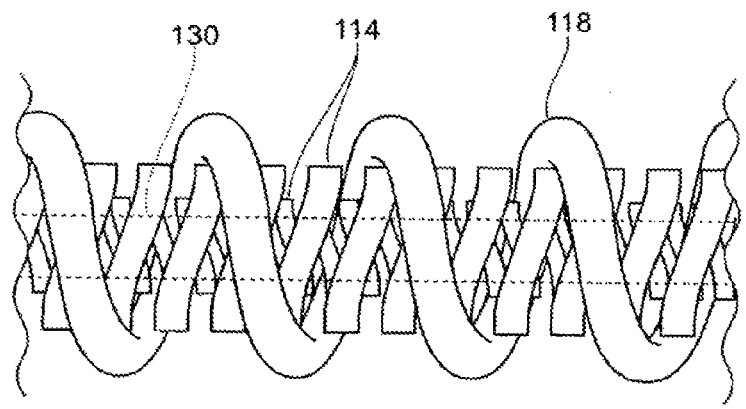
FIG. 19C shows a partial cross sectional view of a variation of a conveying member and a torque shaft having counter wound coils.

FIG. 19C shows a partial sectional view of an alternative example of a torque shaft 114 for coupling to a cutter assembly 102. To aid in removal of materials, the torque shaft 114 may be a set of counter-wound coils, with the outer coil wound at the proper (greater) pitch to form the conveying member 118. Winding the coils counter to each other automatically reinforces the torque shaft 114 during rotation. Alternatively, the torque shaft 114 may be made out of a rigid material such as plastic, rendered flexible by incorporation of a spiral relief or groove which acts as a conveying member 118. Although the shaft 114 may be fabricated from any standard material, variations of the torque shaft may include a metal braid and/or one or more metal coils embedded in a polymer, such as PEBAX, polyurethane, polyethylene, fluoropolymers, parylene, polyimide, PEEK, and PET, as non-limiting examples. These constructions maximize torsional strength and stiffness, as well as column strength for "pushability", and minimize bending stiffness for flexibility. Such features are important for navigation of the catheter through tortuous vessels but allow for smooth transmission of torque over the long length of the catheter.

In the multi-coil construction, the inner coil should be wound in the same sense as that of the rotation so that it would tend to open up under torque resistance. This ensures that the guidewire lumen 130 remain patent during rotation. The outer coil (conveying member) 118 should be wound opposite the inner to counter the expansion to keep the inner coil from binding up against the catheter tube 120.

Typically the guidewire lumen 130 will be used to deliver a guidewire. In such cases, the central lumen 130 may be coated with a lubricious material (such as a hydrophilic coating or Parylene, for example) or made of a lubricious material such as PTFE to avoid binding with the guidewire. However, in some variations, a guidewire section is affixed to the outer distal portion 122 of the catheter body 120, or to the cutter assembly housing 104 (i.e., rapid exchange, to be described later). Moreover, the central lumen 130 of the torque shaft 114 may also be used to deliver fluids to the operative site simultaneously with the guidewire or in place of the guidewire.

Figure 19D:
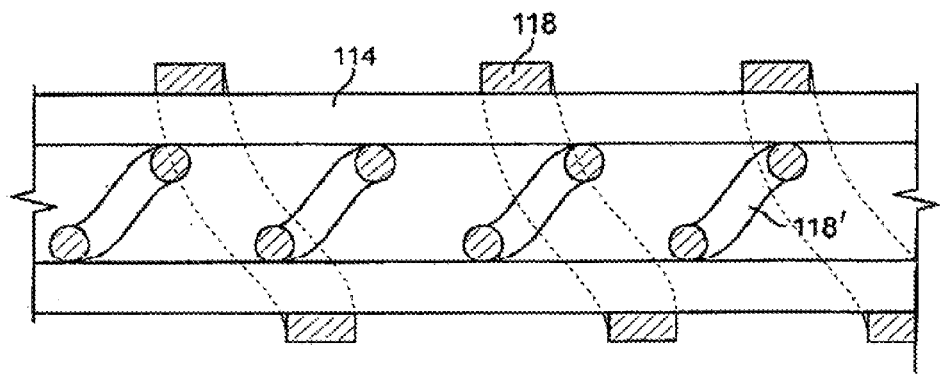
FIG. 19D shows a second conveying member within a torque shaft.
Figure 19E:
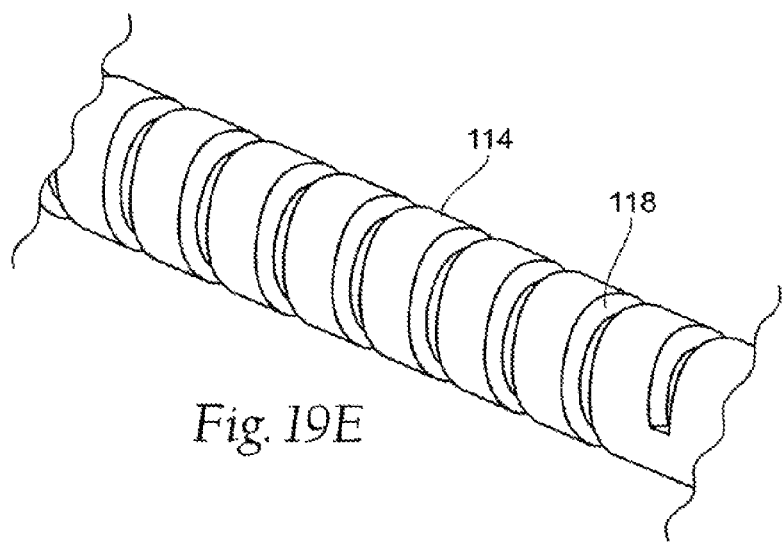
FIG. 19E is a perspective view of an alternative torque shaft including a wound groove as the conveying member.

In some variations, the conveying member 118 may be integral to the shaft 114 (such as by cutting the conveying member 118 into the torque shaft 114 or by extruding the torque shaft 114 directly with a helical groove or protrusion. In an additional variation as shown in FIG. 19D, an additional conveying member 118' may be incorporated on an inside of the torque shaft 114, where the internal conveying member 118' is wound opposite to that of the external conveying member 118. Such a configuration allows for aspiration and debris (via the external conveying member 118) and infusion (via the internal conveying member 118'), or vise-versa. Such a dual action can enhance the ability to excise and aspirate plague by: (1) thinning the blood, whether by viscosity alone or with the addition of anti-coagulants such as heparin or warfarin (cumadin), and/or anti-platetlet drugs such as Clopidogrel, (2) improving the pumpability (aspirability) of the excised plaque by converting it into a solid-liquid slurry that exhibits greater pumping efficiency, and/or (3) establishing a flow-controlled secondary method of trapping emboli that are not sheared directly into the housing, by establishing a local recirculation zone.

As noted above, the conveying member 118 can be wound in the same directional sense as the cutter 108 and in the same direction of rotation to effect aspiration of tissue debris. The impeller action of the cutter 108 moves the tissue debris from inside the housing 104 opening (s) 106, 107, past the cutting edge(s) 112 and 109 to further grind the debris, and into the torque shaft 114. The pitch of the cutting edges 112 may be matched to that of the conveying member 118 to further optimize aspiration. Alternatively, the pitch of the conveying member 118 may be changed to increase the speed at which material moves once it enters the conveying member 118. As discussed herein, debris can be evacuated outside the body by the conveying member 118 action along a portion or the full length of the catheter body 120 and with or without supplement of a vacuum pump 152 connected to the catheter handle 200. Alternatively, the debris may be accumulated in a reservoir within or attached to the system 100.

It may be advantageous to rotatably couple the torque shaft 114 to a drive unit 150 electromagnetically, without physical contact. For example, the torque shaft 114 can have magnetic poles installed at the proximal end, within a tubular structure that is attached to a sheath around the torque shaft. The stationary portion of the motor 150 can be built into the handle 200 that surrounds the tubular structure. This would allow the continuous aspiration through the catheter body 120 without the use of high speed rotating seals.

3. Sweep Frame

Figure 20A:
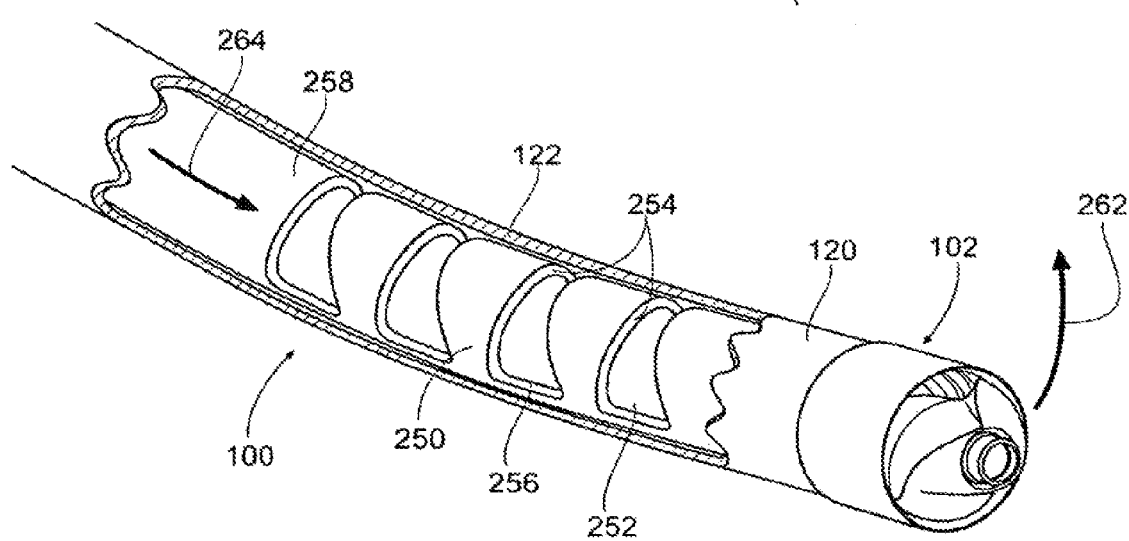
FIG. 20A is a perspective view in partial section similar to FIG. 17, showing the sweep frame causing angular deflection of the distal portion of the catheter.
Figure 20B:
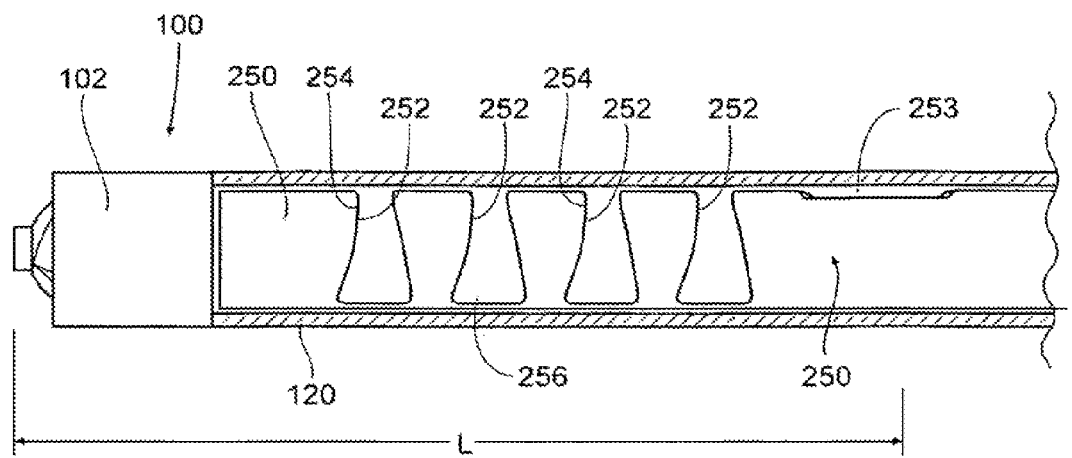
FIG. 20B is a side view of the distal portion of the catheter shown in FIG. 20A, with the sweep frame in an unflexed position.
Figure 20C:
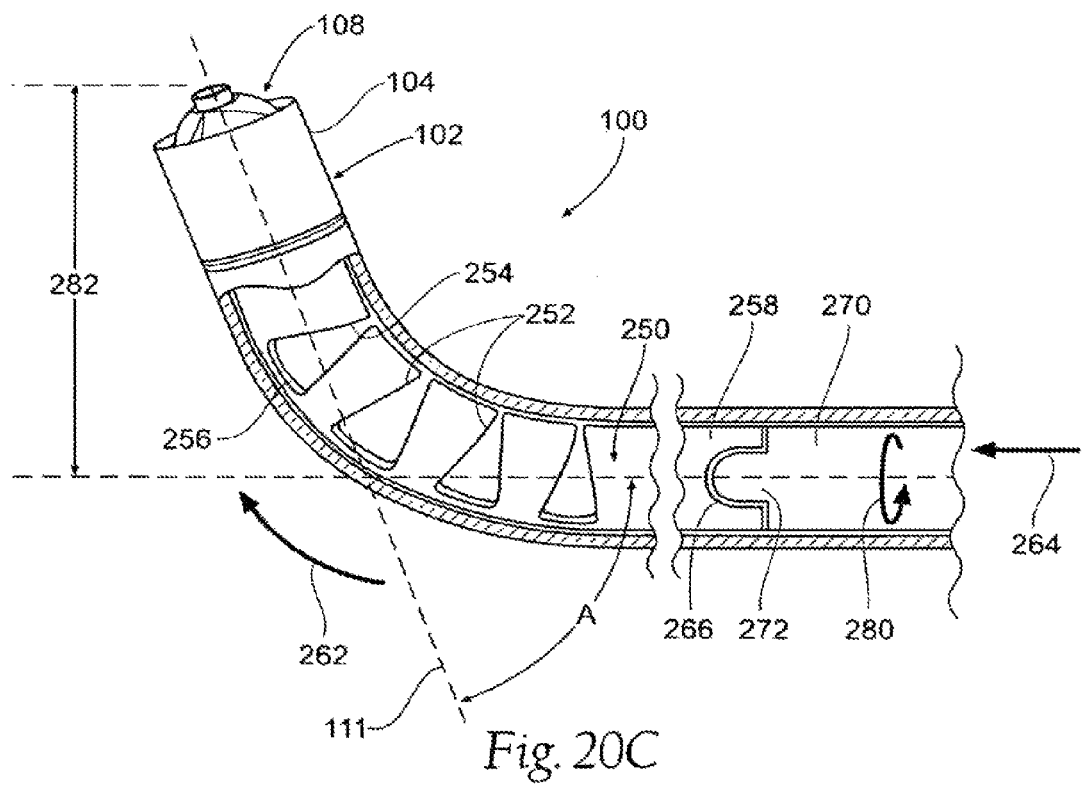
FIG. 20C is a perspective view in partial section similar to FIG. 20A, showing a sweep member abutting the sweep frame, with the sweep frame causing angular deflection of the distal portion of the catheter, where the sweep frame is flexed or compressed to articulate the catheter up to a predefined angle.

FIGS. 20A through 20C further illustrates one embodiment of a sweep frame 250 located within the catheter body 120. The sweep frame 250 may be adapted to permit an axial length L of the distal portion 122 of the catheter 120 to bend or articulate in response to a force typically applied at a proximal portion of the catheter or at the handle 200 of the system 100. The applied force may be provided in a variety of manners, such as distally directed, proximally directed, and/or rotational, or any combination.

In the illustrated embodiment, the sweep frame 250 comprises a tube structure having a plurality of serrations, slots, or semi-circumferential openings 252. Overall, the area having the openings 252 on the sweep frame 250 weaken the frame 250 by providing a section of reduced column strength on a first radial side 254 of the sweep frame (i.e., the sides containing the openings). The portion 256 of the sweep frame 250 that is not weakened maintains a column strength that is greater than that of the first radial side 254 of the sweep frame 250. This constructions permits deflection of the distal portion 122 of the system 100 when an axial force 264 is applied to the sweep frame 250 driving it against a fixed section (e.g., the cutter assembly 102, and/or a portion of the catheter body 120). In an alternative embodiment, an axial force may be applied to the catheter 120 or torque shaft 114, for example, the force driving a fixed section (e.g., the cutter assembly 102) against the sweep frame 250 and causing deflection of the distal portion. As shown in FIG. 20C, this axial force compresses the sweep frame 250 causing the area with the weakened column strength to compress (i.e., the sides of the sweep frame 250 adjacent to the openings 252 move towards one another on the first radial side 254). This in turn causes the deflection of the spine or strengthened side 256 in a direction towards the first radial side 254. Because the sweep frame 250 may be coupled to the catheter (e.g., it may be fully or partially encapsulated within the catheter body 120), the deflection of the sweep frame 250 causes deflection 262 of the distal end 122 of the catheter body 120 and cutter assembly 102 in a direction towards the first radial side 254 causing an axis of the cutter assembly 102 to form an angle A with an axis of the proximal portion 258 of the sweep frame 250.

The sweep frame 250 is rotatable independently of the rotatable cutter 108 and torque shaft 114. In certain variations, the sweep frame 250 is independently rotatable from the catheter body 120 as well. In such configurations, as the deflected sweep frame 250 rotates, the cutting assembly and/or distal catheter portion 122 move in an arcuate path relative to an axis 260 of a proximal end 258 of the sweep frame 250. The sweep frame 250 can also be configured to rotate with the catheter body 120. In this latter configuration, the cutter assembly 102 can also rotate with the sweep frame 250 while the rotatable cutter 108 still is able to rotate independently of the sweep frame 250.

Figure 21A:
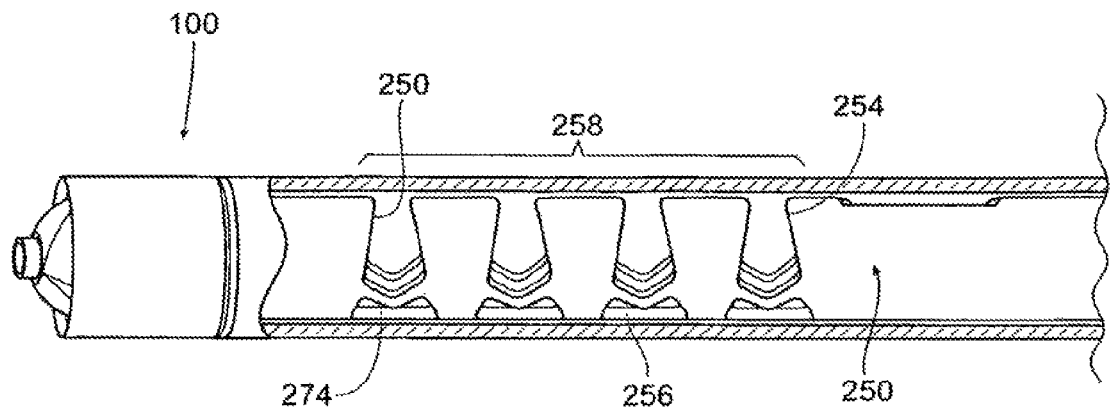
FIGS. 21A through 21C show additional variations of sweep frames for use with the debulking devices described herein.
Figure 21B:
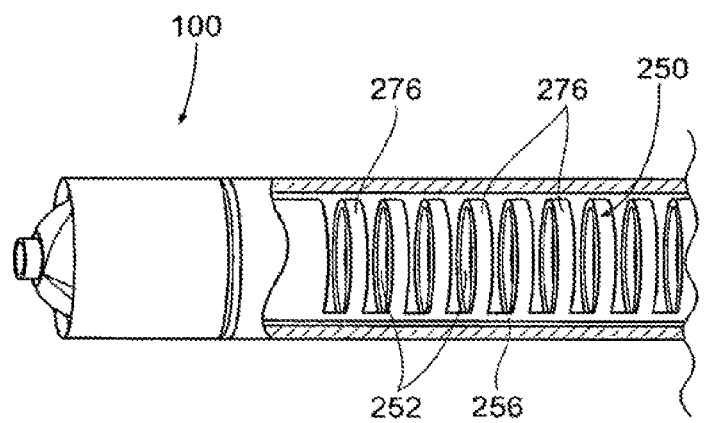
Figure 21C:
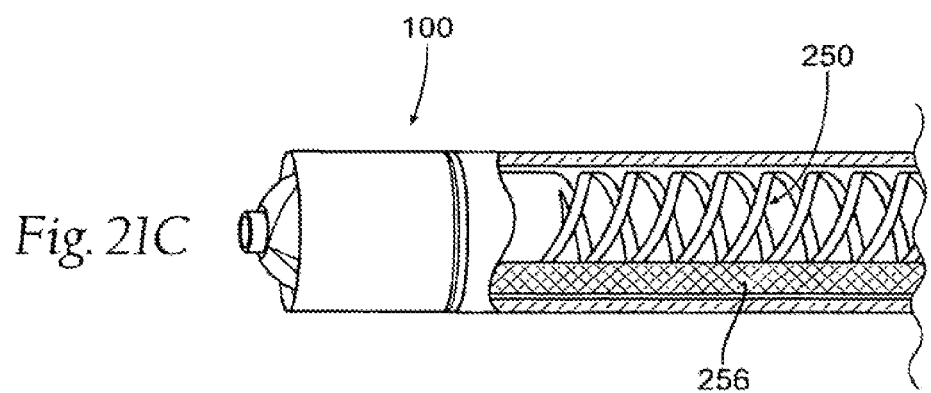

FIGS. 21A through 21C illustrate additional variations of sweep frames 250 for use with the cutting assemblies 102 and catheters 120 described herein. For purposes of highlighting the sweep frame 250, the torque shaft 114 is omitted from FIGS. 21A to 21C. However, as shown in FIG. 17 for example, a torque shaft 114 may extend through the sweep frame 250 where the torque shaft and sweep frame can rotate independently from one another.

FIG. 21A shows a distal view of a debulking system 100 where the catheter body 120 is partially removed to show a variation of a sweep frame 250. In this variation, the sweep frame 250 may be constructed from a laser cut tube having serrations, openings, or slots 252. The openings 252 create a weakened section along a first radial side 254 of the sweep frame 250. The side opposite 256 to the first radial side 254 comprises an area of increased column strength. Accordingly, as a physician applies an axial force (e.g., in a distal direction) at the proximal end of the system 100, typically via a sweep member 270, as discussed below, the axial force causes the sweep frame 250 to compress against a fixed area within the distal portion 122 of the catheter body 120 (see FIG. 20B). As the force compresses the sweep frame 250, the sweep frame 250 is forced to compress at the weakened section along the first radial side 254 causing bending at the continuous area or spine 256 of the sweep frame 250 in the direction indicated by the arrow 262 (see FIG. 20C). The fixation area (the area against which the sweep frame 250 encounters resistance) can be the cutter assembly 102 or a distal area on the catheter body 120. However, any area will suffice so long as the sweep frame 250 is able to bend upon the application of a force.

The spacing and size of the openings 252 can be selected to allow a pre-determined bend upon deformation of the sweep frame 250. For example, the openings 252 can be selected to limit deflection of the distal portion 122 of the catheter to plus or minus 90 degrees or to any angular bend to provide an added safety measure when the system 100 is used within a vessel. Moreover, the spacing between adjacent openings 252 and/or the size of openings can vary in the sweep frame 250. For example, the spacing and/or size of the openings 252 can increase or decrease along the length of the sweep frame 250.

In an additional variation, the spacing and the size of the openings can vary inversely along the length of the sweep frame 250.

In the illustrated variation, the size of the openings 252 in the sweep frame 250 may increase in a direction away from the first radial side 254 of the sweep frame 250. This configuration was found to minimise interference with the torque shaft (not shown).

In addition, the sweep frames 250 described herein can have any number of features to assist in joining the sweep frame 250 to the catheter 120. For example, in those cases where the sweep frame 250 is constructed from a superelastic or shape memory alloy, the frame 250 can include one or more openings 253 located in a sidewall to increase the bond between the superelastic/shape memory alloy component and a regular metallic shaft.

4. Sweep Member

FIG. 20C illustrates the tissue debulking system 100 upon the application of force indicated in the direction of arrow 264. As noted above, force 264 may be applied by the physician at the proximal end or handle 200 of the system 100. In some variations, the force may be applied through the use of a sweep member 270 that is axially moveable within the catheter body 120. The sweep member 270 can comprise a tubular structure or a spline or wire that has sufficient column strength to compress as well as rotate the sweep frame 250. Because the distal end of the sweep frame is prevented from moving distally (typically because the cutter assembly 102 is affixed to the catheter body 120), the sweep frame bends at the spine 256 in the direction of the first radial side 254. As shown, the spacing between the openings 252 may simply decrease starting at the first radial side 254 and extending to the spine 256. This causes articulation of the cutting assembly 102 so that an axis 111 of the cutting assembly becomes offset from an axis of the proximal end 258 of the sweep frame 250 as denoted by angle A. As noted herein, the angle A is not limited to that shown. Instead, the angle can be predetermined, depending on the construction of a particular sweep frame 250 to provide any angle that is suited for a target vessel or body lumen, and may range plus or minus 90 degrees or to any predetermined angular bend.

In one variation, the sweep member 270 (also called a sweep shaft) may be fabricated as a hypo-tube structure (constructed from a super-elastic alloy or a medical grade stainless steel, for example). The sweep member 270 can have varying degrees of flexibility to allow the catheter 120 to be more flexible at a distal portion and rigid at a proximal portion. This allows for improved navigation through tortuous anatomy as well as improved transmission of torque generated at the proximal end of the device. In additional variations, the sweep-member 270 should not be prone to excessive compression or elongation given that it must transmit the rotational force to the sweep frame 250.

Upon articulation of the cutting assembly 102, the physician can further rotate the sweep member 270 as shown by arrow 280. Rotation of the sweep member 270 causes rotation of the sweep frame 250 when articulated causing movement of the cutting assembly 102 in an arc-type motion about an axis of the proximal end 258 of the sweep frame 250. This movement causes the cutting assembly 102 having a flexible length L to move through an arc having a radius denoted by 282. In some variations of the device, the sweep frame 250 and sweep member 270 can rotate independently of the catheter body 120. However, allowing the catheter body 120 to rotate with the sweep frame 250 and sweep member 270 reduces the resistance on the sweep member 270 as it rotates. In this latter case, the catheter body 120, as well as the cutter housing 104, rotate with the sweep frame 250. However, the rotatable cutter 108 (and the torque shaft—not shown) still rotate independently of the sweep frame 250.

Also as noted above, this ability to sweep the cutting assembly 102 in an arc or a circle larger than a diameter of the catheter 120 (or cutter assembly 102) allows the physician to create a significantly larger opening in the target site than the diameter of the cutting assembly 102 itself. Such a feature eliminates the need to exchange the system 100 for a separate cutting instrument having a larger cutting head. Not only does such a feature save procedure time, but the system 100 is able to create variable sized openings in body lumens.

FIG. 20C also illustrates a variation of the sweep member 270 that can be applied to any variation of the system 100 shown herein. In some cases it may be desirable to disengage the sweep member 270 from the sweep frame 250. In such a case, the sweep member 270 can be axially slidable to disengage the sweep frame 250. However, upon re-engagement with the sweep frame 250, the sweep member 270 must also be able to rotate the sweep frame 250. Accordingly, the sweep frame 250 and sweep member 270 can include one or more keys and key-ways. Although the illustration shows the sweep frame 250 as having a keyway 266 at a proximal end 258 and the sweep member 270 as having a key 272, any type of configuration that allows translation of rotation is within the scope of this disclosure.

FIG. 21A illustrates a variation of a system 100 having sweep frame 250 with a weakened section 268 having a varying column strength. In this variation, the column strength of the sweep frame 250 increases in a circumferential direction away from the first radial side 254. The increase in column strength prevents radial twisting of the sweep frame 250 as it deflects. In the illustrated variation, the sweep frame 250 comprises a plurality of reinforcement arms, ribs, or struts 274 within the openings 250 on the sweep frame 250 where the arms, ribs, or struts 274 are configured to preferentially bend towards the spine 256 as the sweep frame 250 bends. In this variation, the portion containing the arms, ribs, or struts 274 that is adjacent to (but spaced from) the first radial side 254 comprises a second column strength that is greater than the column strength of the radial side but less than a column strength of the remaining spine 256. Again, the varying column strength is intended to prevent twisting of the sweep frame 250 upon deflection.

FIG. 21B shows another variation of a sweep frame 250. In this variation, the sweep frame comprises a plurality of rings 276 spaced apart to create the openings 252 within the sweep frame 250. The rings can be joined at the spine area 256 via a separate member, a polymer coating, or a separate frame that is ultimately joined to the rings 276. As noted above, the rings can be spaced or vary in size to achieve the desired predetermined curvature upon compression of the sweep frame 250.

FIG. 21C shows another variation of a sweep frame 250 comprising a woven, coiled, braided or laser cut mesh structure similar to that of a vascular stent. The sweep frame 250 structure can comprise a wire or ribbon material having a reinforced section to function as the spine 256. For example, one side of the stent structure sweep frame 250 can be treated via a coating, fixture or any other means to increase a column strength of the section. Accordingly, this area of the stent structure sweep frame 250 functions as a spine 256 of the sweep frame 250. Although the spine 256 of FIGS. 21B and 21C are shown to be along a bottom portion of the respective sweep frames, the sweep frames can be manufactured to provide varying regions of column strength as described above.

It is understood that the sweep frames can vary from those that are shown to be any structure that allows for preferential bending and rotation when placed within the catheter 120. The sweep frame can be fabricated from a variety of materials including a shape memory alloy, a super elastic alloy, a medical grade stainless steel, or other polymeric material, as non-limiting examples. The material of the sweep frame 250 can be radiopaque, or can be altered to be radiopaque. In such cases, the physician will be able to observe the degree of articulation of the device by observing the curve of the sweep frame 250 prior to cutting tissue.

5. Steering and Sweeping

Figure 22A:
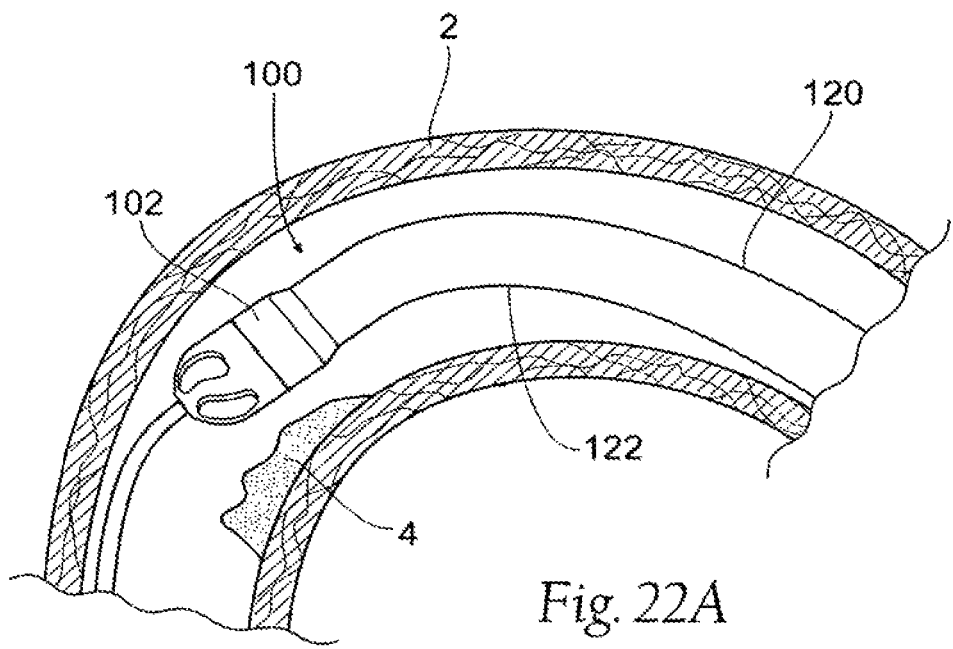
FIG. 22A illustrates articulation of the distal portion of the catheter around a tortuous bend to reach a lesion for removal.

FIG. 22A illustrates an example of a variation of a debulking system 100 being steered when using a sweep frame 250 and sweep member 270 as described above. The ability to steer the distal portion 122 and cutting assembly 102 of the system 100 is useful under a number of conditions. For example, when debulking an eccentric lesion in a tortuous vessel as shown, the cutting assembly 102 should be pointed towards the side of the vessel 2 having the greater amount of stenotic material 4. Naturally, this orientation helps prevent cutting into the bare wall/vessel 2 and focuses the cutting on stenotic tissue 4. When in a curved section of the vessel 2, without the ability to steer, the cutting assembly 102 would tend to bias towards the outside of the curve. As shown in FIG. 22A, steering allows the cutting assembly 102 to point inward to avoid accidental cutting of vessel wall 2.

Figure 22B:
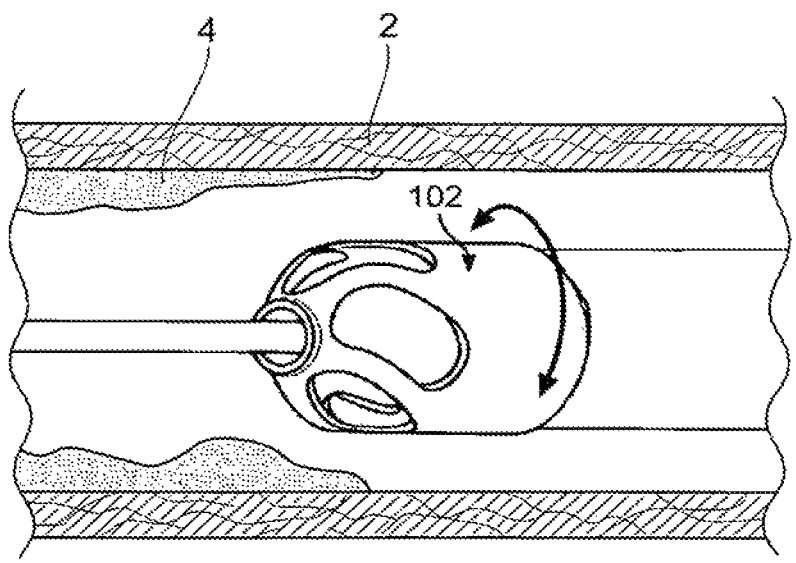
FIG. 22B through 22D shows variations of sweeping of the cutting assembly, with the sweep being able to rotate 360 degrees or more.
Figure 22C:
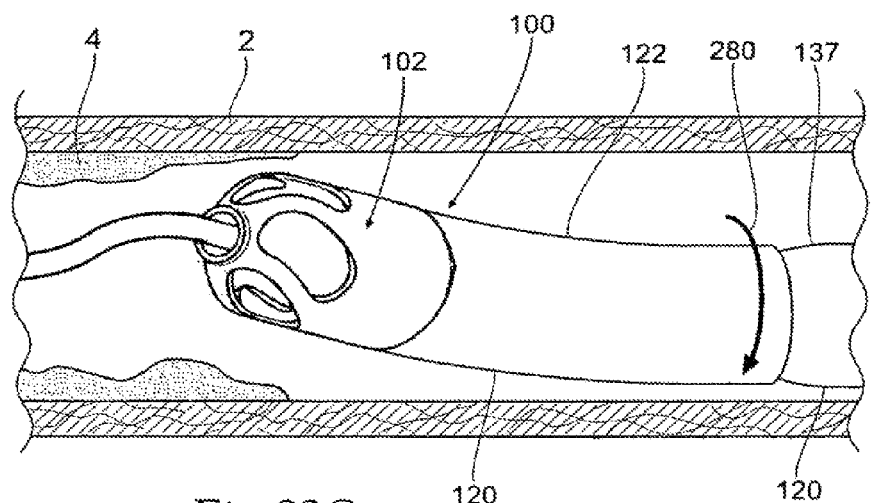

The ability to steer the device 100 also allows for a sweeping motion when cutting occlusive material. FIG. 22B shows the rotation of the cutting assembly 102. As shown in FIG. 22C, when the cutting assembly 102 deflects relative to the axis of the catheter, rotation of the deflected portion 102 creates a sweeping motion. It is noted that rotation or articulation of the cutting assembly 102 also includes rotation or articulation of the catheter to allow the cutting assembly to deflect relative to an axis of the catheter.

Figure 22D:
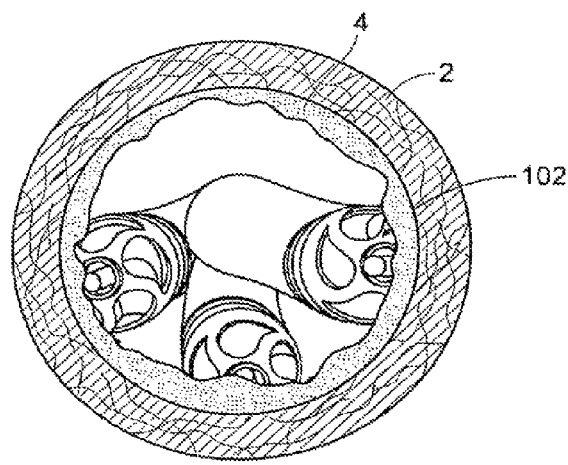

FIG. 22D shows a front view taken along an axis of the vessel to illustrate the sweeping motion causing the cutting assembly 102 to sweep over a larger region than the diameter of the cutting assembly 102. In most cases, when articulated, the cutting assembly 102 may be rotated to sweep over an arc, a full circle, or a controlled orbit of multiple circles.

A user of the system 100 may couple the sweeping motion of the cutting assembly 102 with axial translation of the catheter 120 for efficient creation of a larger diameter opening over a length of the occluded vessel. This is because the system 100 is adapted to "sweep" the lumen of materials, the sweep feature allowing the system 100 to create a passage (i.e., diameter) in the lumen having a ratio ranging from about 1 (one) to up to about 4 times the diameter of the catheter 120, which equates to creating a passage having a cross-sectional area of up to 16 times greater than the cross-sectional area of the catheter 120. Prior concentrically operating atherectomy systems are limited in their ability to clear a lumen to their maximum area of cut.

By clearing a larger diameter passage than the diameter of the debulking device, the system 100 creates a clinically relevant increase in size of the lumen for blood flow. A clearing system adapted to double the diameter of the lumen (compared to the diameter of the catheter) is able to quadruple the area available for blood flow. The system is adapted to debulk vessels ranging in diameter from about 1 (one) mm to about 15 mm, although smaller and larger diameter vessels are within the scope of the invention. In addition, the system 100 is adapted to traverse the cutting assembly across the inner width of the vessel, i.e., approximately 10 mm.

For example, using the formula ($\pi R^2$) for the area of a circle, and using a catheter with a diameter of 2 mm, the area of the catheter is $(3.14 \times 1^2) = 3.14$ mm². Now using a cleared cross-sectional area having a diameter of 4 mm, the area of the cleared lumen is $(3.14 \times 2^2) = 12.56$ mm², a factor of four times the cross-sectional area of the catheter. Now using a cleared cross-sectional area having a diameter of 8 mm, the area of the cleared lumen is $(3.14 \times 4^2) = 50.24$ mm², a factor of 16 times the cross-sectional area of the catheter.

Figure 22E:
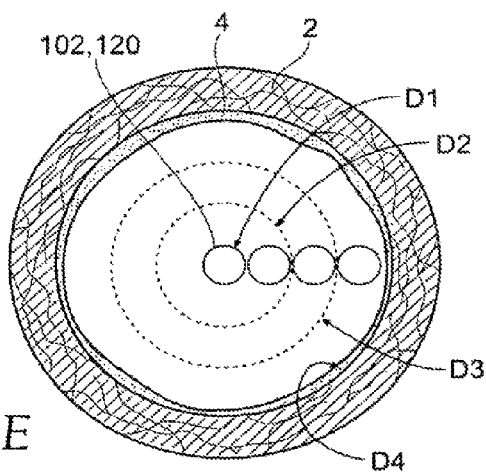
FIG. 22E a cross sectional view of a vessel, and showing the ability of the system to clear a lumen in a vessel up to four times the diameter of the catheter.

As seen in FIG. 22E, the catheter 120 has a diameter D1. The ability to steer and sweep allows the system to clear a lumen having a cross-sectional diameter greater that the catheter 120, including a diameter D2 (twice the diameter of the catheter), D3 (three times the diameter of the catheter), and D4 (four times the diameter of the catheter).

The combination of movements described for steering and/or sweeping may be performed when the device is placed over a guidewire (although not necessary), for example by the use of a lead screw in the proximal handle assembly 200 of the system. In another aspect of the systems described herein, the angle of articulation may be fixed so that the system 100 sweeps in a uniform manner when rotated.

FIG. 22C also shows a variation of a debulking system 100 having a catheter body 120 where a first or distal portion 122 of the catheter body rotates as identified by arrow 280 as the cutting assembly 102 sweeps in an arc. The second portion 137 of the catheter remains stationary. Accordingly, the two part catheter may be joined to permit the relative movement between sections. The distal portion 122 and/or the second portion 137 may incorporate a sweep frame 250 and/or sweep member 270.

As described above, the catheter body 120 can remains stationary while the inner sweep frame 250 and sweep member 270 rotate to move the cutting assembly 102 in an arc or orbit within the lumen. Alternatively, the sweep frame 250 and sweep member 270 can rotate with the catheter body 120 but independently of the cutting assembly 102 and torque shaft 114.

Again, the sweep member 270 can be composed of a super-elastic alloy, a medical grade stainless steel, a metal braid sandwiched in a polymeric matrix of such materials as polyethylene (PE), fluoro-polymer (PTFE), nylon, and/or polyether-block amide (PEBAX), polyurethane, and/or silicone, as non-limiting examples. The sweep member 270 can also be made of counter wound metal coils. Its distal end is curved and is preferably made of a material that can withstand high degree of flex and retain its curved shape. Such material may include polymers such as PE, nylon, Polyetheretherketone (PEEK), Nickel Titanium (Nitinol), or spring steel, as non-limiting examples.

As described above, selecting a desired profile for bending, torsion and axial strength characteristics when designing the catheter body 120 and/or sweep member 270 improves the overall function of the debulking catheter system 100. Aside from the improved ability to advance the cutting assembly 102 and sweep the cutting assembly in an arc-type motion, the proper characteristics improve the ability of the physician to steer the catheter 120. For example, selection of the proper characteristics reduces the chance that the distal portion 122 of the catheter 120 rotates more or less than the proximal end or control knob 202 on the handle 200.

These characteristics along with the ability to steer the catheter 120 provide a system 100 capable of both active and passive steering. Active steering may incorporate both flexing the distal portion 122 and rotating the distal portion to steer through tortuous anatomy. As described below, this allows the physician to advance the catheter 120 with or without a guidewire though tortuous anatomy, and to direct the forward facing cutting assembly 102 to a side wail of a lumen to remove occlusive materials. Passive steering may incorporate advancement of the catheter 120 until the cutting assembly 102 contacts a bend in the vessel, for example. A simple rotation of the sweep frame 250 to adjust the first radial side 254 of the sweep frame to the inside radius of the bend (and the spine 256 to the outside radius of the bend) allows the flexible distal portion to naturally or preferentially bend with the vessel, and the catheter 120 may continue to be advanced.

Figures 23A, 23B:
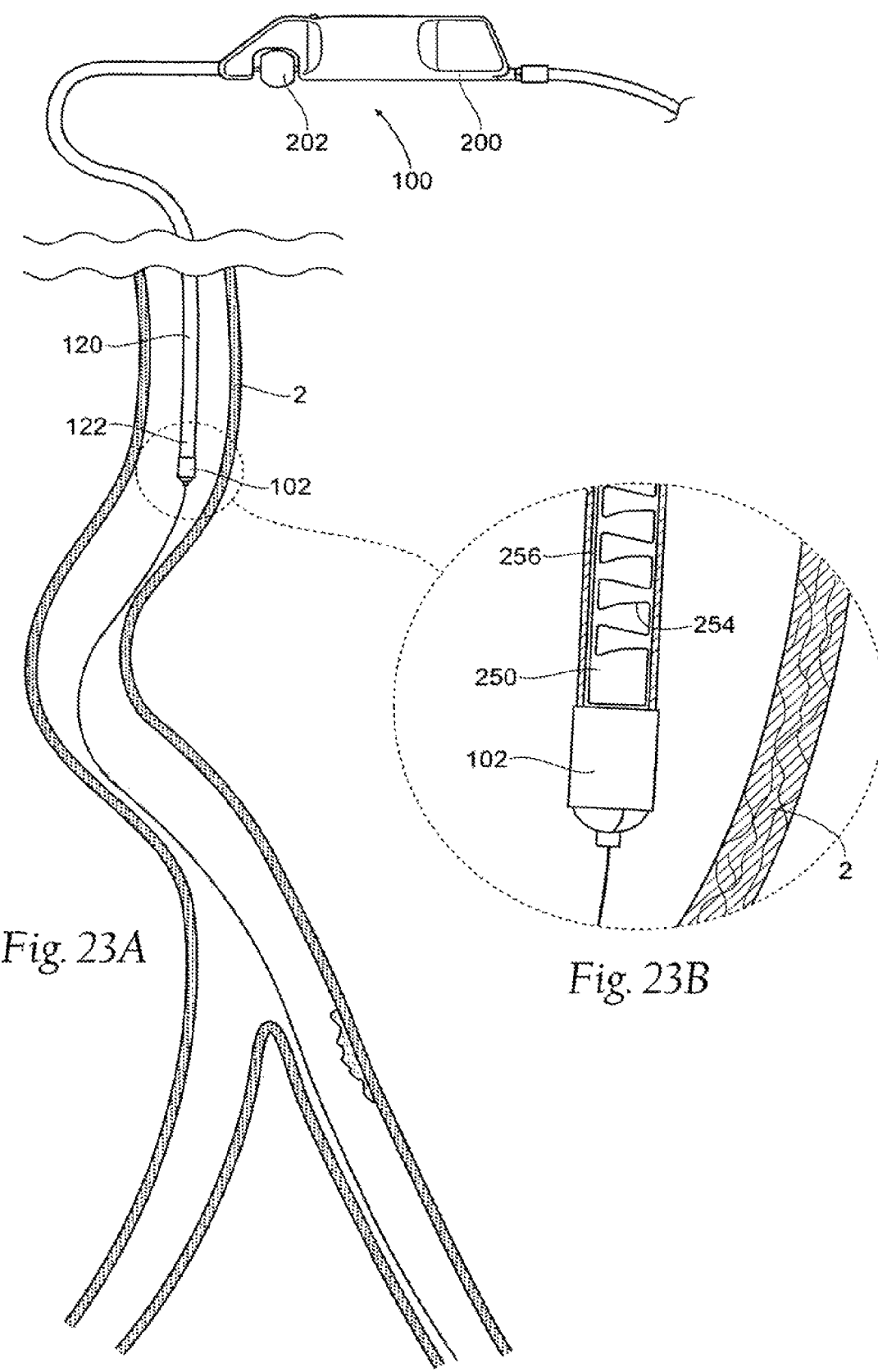

FIGS. 23A through 23H show an advancement of the catheter 120 through a tortuous vessel 2, and steering the cutting assembly 102 to a difficult to access treatment site at an inside corner of a vessel bifurcation. FIGS. 23A and 23B show the catheter 120 advanced into the vessel 2 until a bend is contacted. As seen in FIG. 23B, the spine 256 of the unflexed sweep frame 250 is shown on the inside radius of the vessel bend.

Figures 23C, 23D:
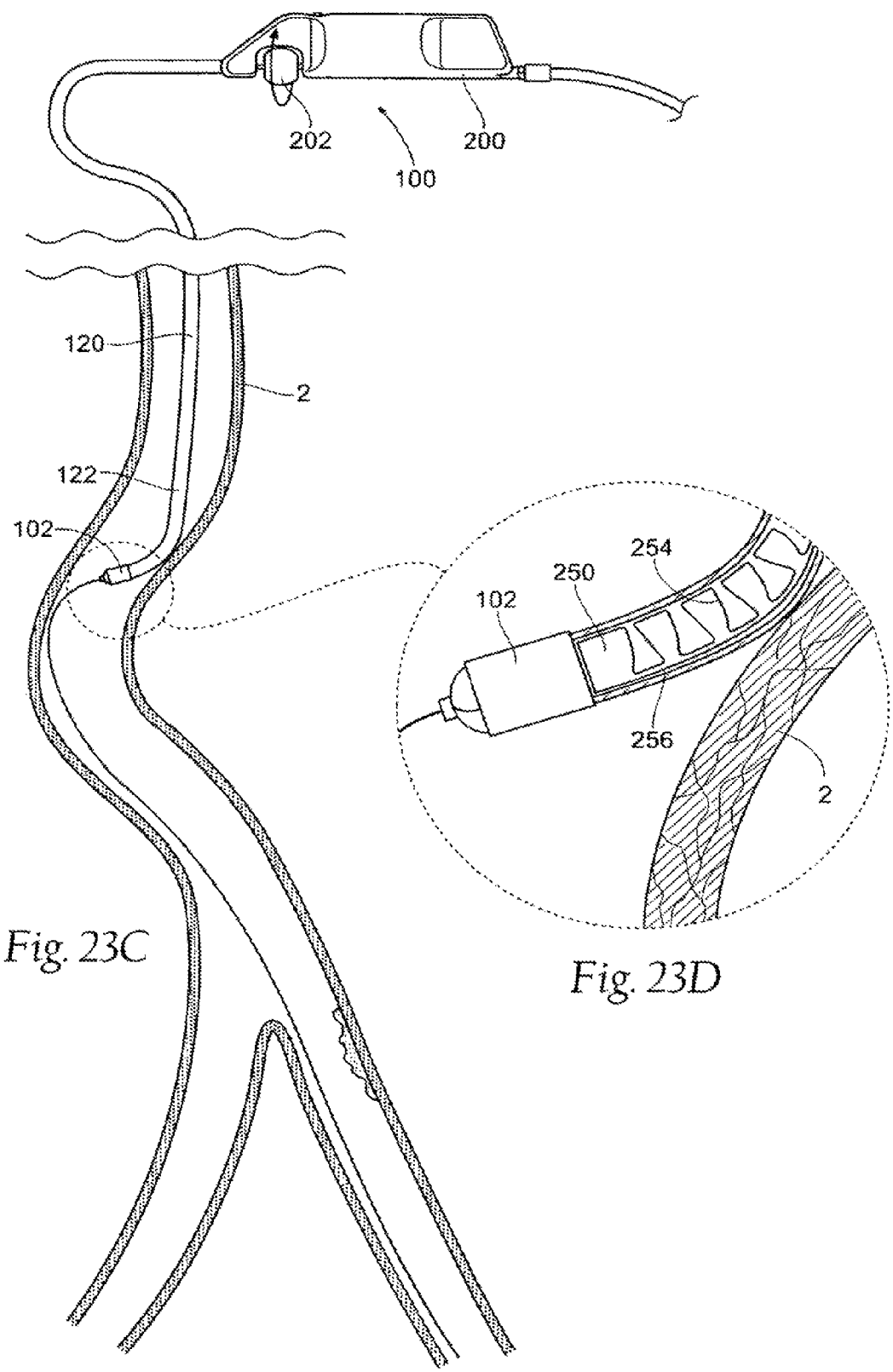
Figures 23E, 23F:
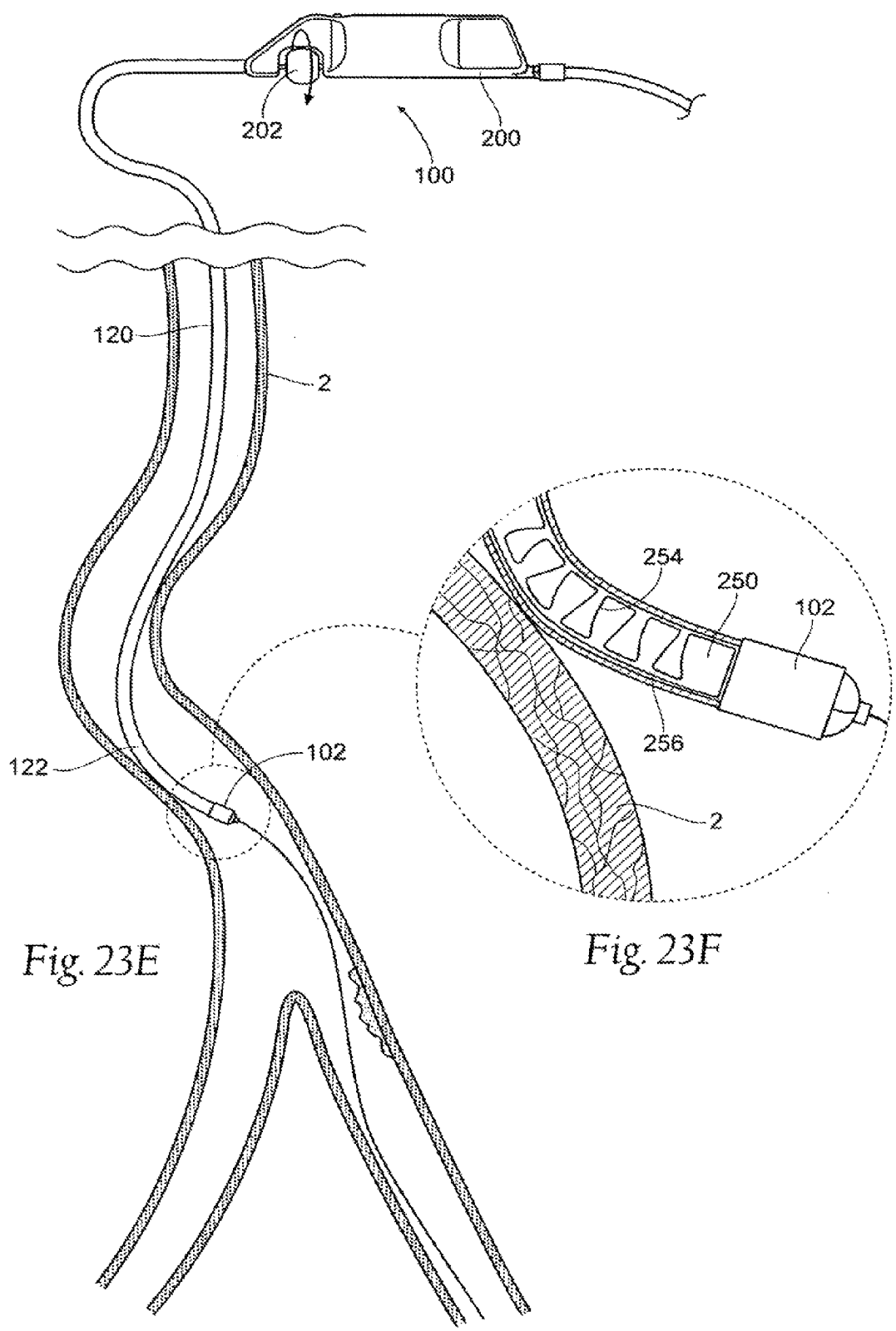

FIGS. 23C and 23D show passive steering by simply rotating the sweep frame 250 using the steering controls on the handle 200 to position the first radial side 254 of the sweep frame to the inside radius of the bend. This rotation of the sweep frame allows the distal portion to naturally bend with the vessel, and the catheter 120 may continue to be advanced. FIGS. 23E and 23F show the catheter 120 advanced to the next bend in the vessel 2, and the passive steering process repeated to rotate the first radial side of the sweep frame 250 to the inside radius of the bend, allowing the flexible distal portion to naturally bend with the vessel.

FIGS. 23G and 23H show the catheter 120 being actively steered to access an inside vessel wall to remove material 4. As can be seen, the control knob 202 on the handle 200 may be both advanced to deflect the distal portion of the catheter, and the knob 202 may also be rotated to sweep the flexible distal portion across the lesion 4 for debulking.

Figure 24A:
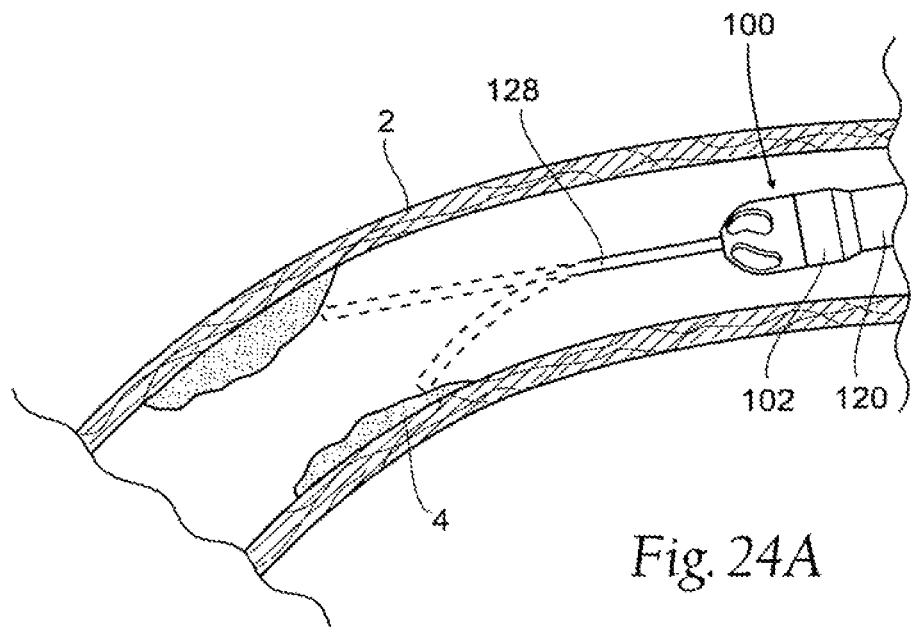
FIGS. 24A through 24C illustrate the use of a debulking device to assist in the navigation of a guidewire through tortuous anatomy and occluding material.
Figure 24B:
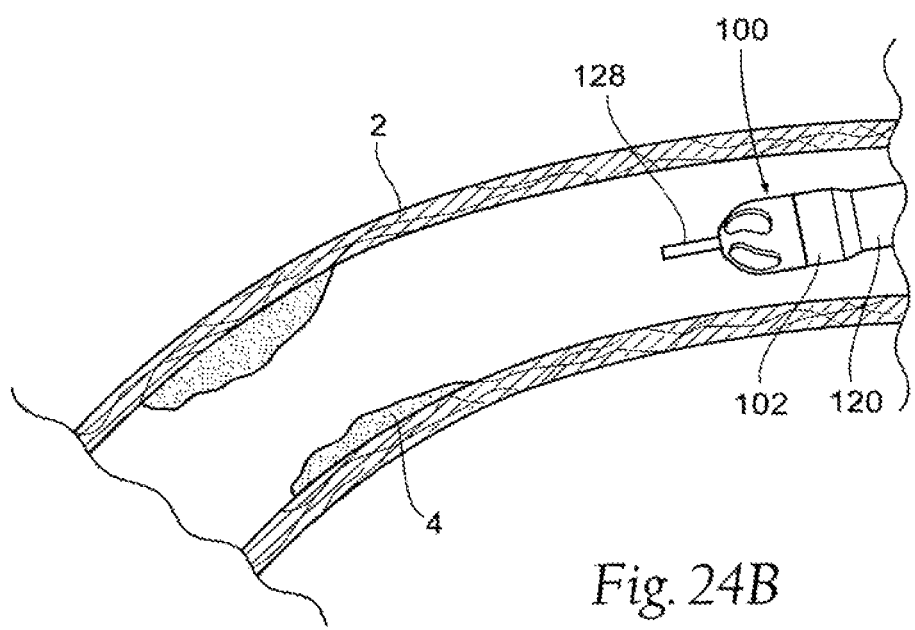
Figure 24C:
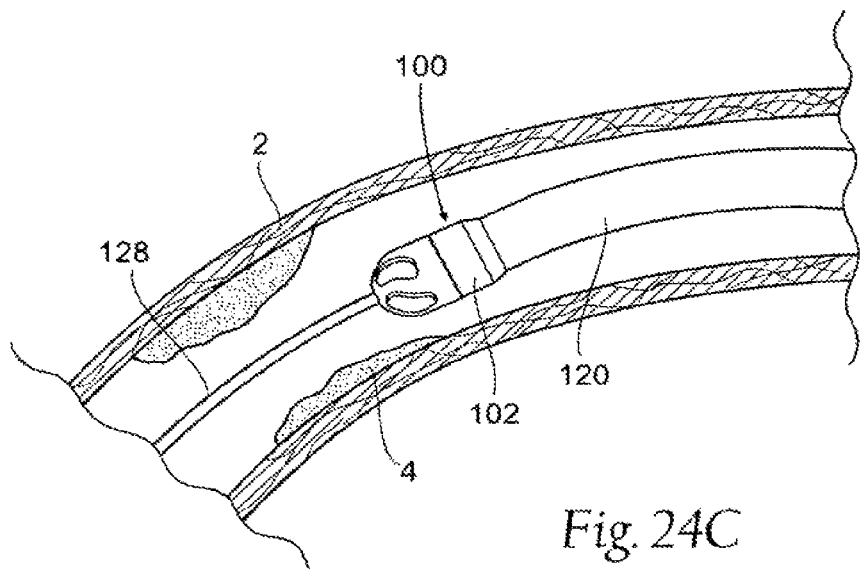

In another variation of the invention, the system 100 can improve the ability of a physician attempting to navigate a guidewire 128 through branching, tortuous or otherwise obstructed anatomy. In the variation shown in FIG. 24A, as a physician navigates a guidewire 128 through the anatomy, the tortuous nature of the anatomy or obstructions 4 within the vessel 2 may prevent advancement of the guidewire 128 as shown. In such a case, the system 100 of the present invention permits a physician to withdraw the guidewire within the catheter 120 or just distal to the cutting assembly 102 (as shown in FIG. 24B). The system 100 can then be advanced to a branching point or beyond the tortuous location or obstruction, and articulated (as shown in FIG. 24C) so that the physician can then advance the guidewire 128 beyond the obstruction, sharp bend, or into the desired branch.

Figure 24D:
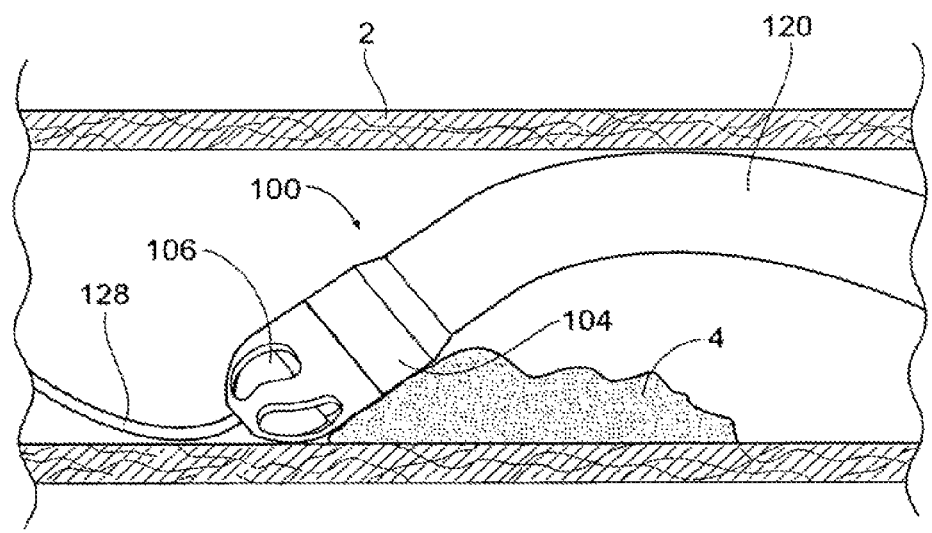
FIG. 24D shows placement of housing windows to prevent damage to the vessel walls, and apposition of the catheter against the vessel wall.

As previously described, the shape of the housing 104 as well as the location of the window(s) 106, 107 can be chosen so that when the cutting assembly 102 is substantially aligned with the lesion, or engages it at less than some critical attack angle, it will cut effectively. However, when pivoted at an angle greater than the critical angle, the cutting edges or grinding element will not engage the lesion, as shown in FIG. 24D. This means that at large deflections, as the distal portion of the cutting assembly 102 approaches the vessel wall, it automatically reduces its depth of cut and ultimately will not cut when the critical angle is exceeded. For example, the cutter 108 distal tip is blunt and does not cut. As the cutting assembly 102 is deflected outward, the blunt tip contacts the vessel and keeps the cutting edges proximal to the tip from contacting the vessel wall. In addition, the guidewire in combination with the cutting assembly 102 can also act as a buffer to prevent the cutting edges from reaching the vessel wall. As shown, the portion of the guidewire that extends from the housing 104 will bend at a minimum bend radius. This permits a portion of the guidewire closest to the housing to act as a bumper and prevents the cutter 108 and windows 106 from engaging the walls of the vessel. In certain variations, guidewires with varying bend radii can be selected to offer varying degrees of protection by spacing the cutter 108 away from the tissue wall.

C. The Handle Assembly

Figure 25A:
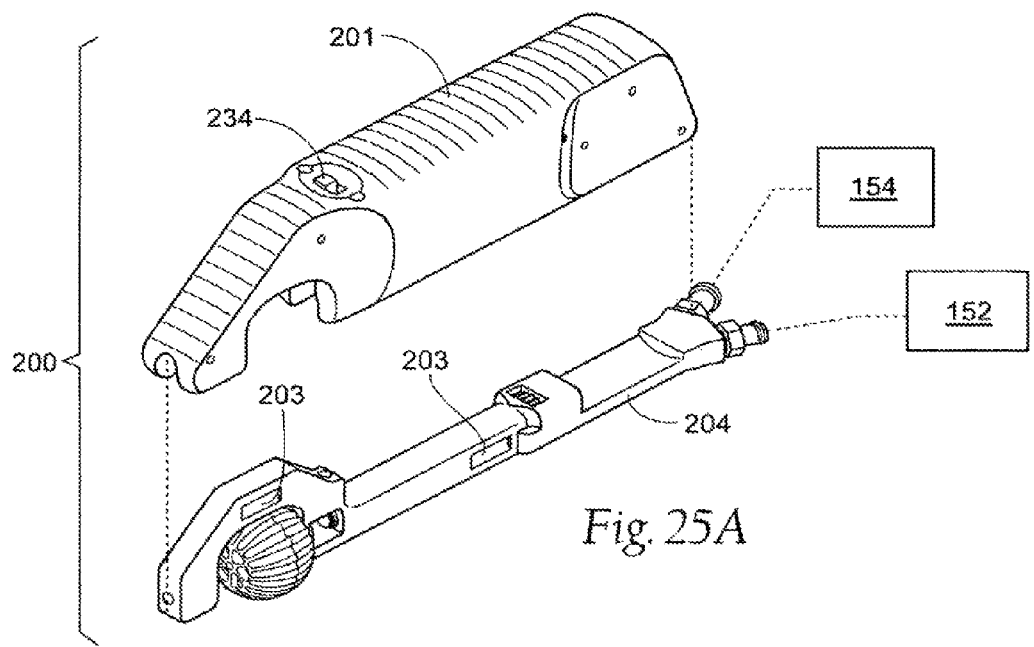
FIG. 25A shows an exploded view of a control handle for the debulking system, the handle adapted for rotating and articulating the distal portion of the catheter, including the cutter assembly.

FIG. 25A shows an exploded view of one embodiment of a control handle 200 adapted to provide operational controls for the system 100. As shown, the handle 200 may comprise a handle base portion 201 and a catheter chassis portion 204, both of which may snap or otherwise be coupled together to form the handle 200. Both the handle base 201 and the catheter chassis 204 may be provided to the user as a sterile, single use, and disposable device, along with the catheter 120 and cutting assembly 102. The two component handle 200 allows for improved manufacturability of the individual components, i.e., the handle base 201 and the catheter chassis 204, and for isolation of the power (e.g., power means 236) and rotating means 150 from the catheter chassis 204. It is to be appreciated that the handle 200 may be a single component handle, or may be more than two components as well.

1. Handle Base

Figure 25B:
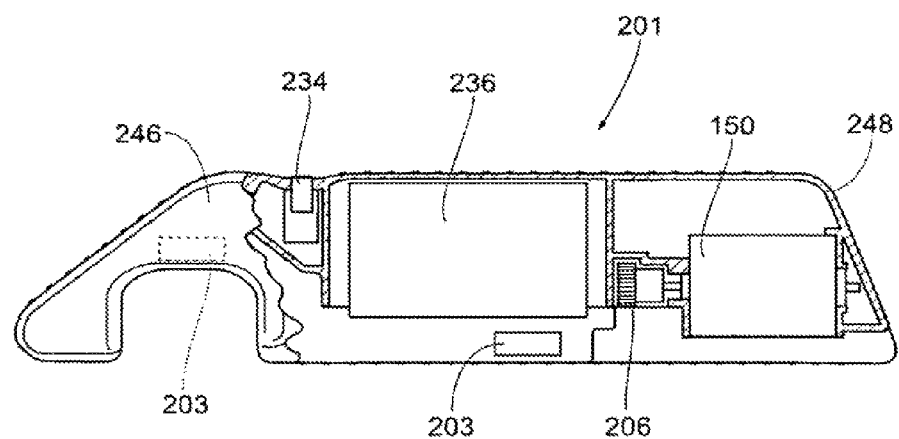
FIG. 25B is a side view in partial section showing the handle base portion adapted to house functional elements of the control handle, and to isolate functions of the control handle from the catheter chassis.

As seen in FIGS. 25A and 25B, the handle base 201 comprises an ergonomic grip and functionally convenient access to operational controls of the system 100. A first base piece 246 and a second base piece 248 may be coupled together to house elements including on/off means 234, power means 236, rotational means 150, and a gear 206 coupled to the rotational means. The handle base 201 may be composed of a polymeric matrix of such materials as polycarbonate, acrylonitrile-butadiene-styrene (ABS), polymethyl methacrylate (PMMA), polysulfone, polyethylene ptherethalate (PET), high density polyethylene (HDPE), polyethylene (PE), nylon, polyether-block amide (PEBAX), polyurethane, and/or silicone, as non-limiting examples. As can be seen in FIG. 25B, coupling means 203, e.g., snap, clip, glue, weld, heat, and screw features, may be provided on the handle base 201 and/or the catheter chassis 204, and allow for tool free coupling between the handle base 201 and the catheter chassis 204.

The on/off means 234 may provide a variety of control options for control of the rotation of the cutter 108 including on/off, ramp up and/or ramp down, and/or variable speed, as non-limiting examples. The on/off means may be any of a variety of known control mechanisms, including a slide switch, pushbutton, and/or potentiometer, as non-limiting examples.

A power source 236 is desirably coupled to the on/off means 234 and the rotating means 150. The power source 236 may comprise a variety of known power sources, such as a non-rechargeable battery, a rechargeable battery, and a capacitor, as non-limiting examples. Desirably, the power source 236 is adapted to maintain a consistent supply of power to the rotating mechanism 150 through all operating conditions, including no load through excessive torque and stall conditions, without excessively draining the power source 236. The power source may also have a predetermined amount of operational power, e.g., sufficient power to operate the system 100 continuously during a procedure for about two to about three hours, as a non-limiting example.

The rotating means 150, when powered on, provides rotation to a gear 206. The gear 206 meshes with a catheter chassis drive gear 207, which drives the torque shaft 114 (see FIG. 30). The rotating mechanism 150 (e.g., an electric, pneumatic, fluid, gas, or other rotational system), transmits the rotational energy to the torque shaft 114, with the torque shaft 114 transmitting the rotational energy to the cutter 108.

Variations of the system 100 may include use of a rotating mechanism 150 located entirely within the handle 200, as shown. In an alternative variation, the rotating mechanism 150 may be outside the handle 200 and/or outside of the surgical field (i.e., in a non-sterile zone) while a portion of the system (e.g., the torque shaft 114) extends outside of the surgical field and couples to the rotating mechanism 150.

The rotating mechanism 150 may be a motor drive unit. In one working example, a motor drive unit operating at 4.5 volts and capable of producing cutting speeds up to 25,000 RPM was used. Another example of a motor drive unit included supplying the motor at 6 volts nominal, running at about 12,000 RPM with higher torque. This was accomplished by changing the gear ratio from 3:1 to 1:1.

Figure 26A:
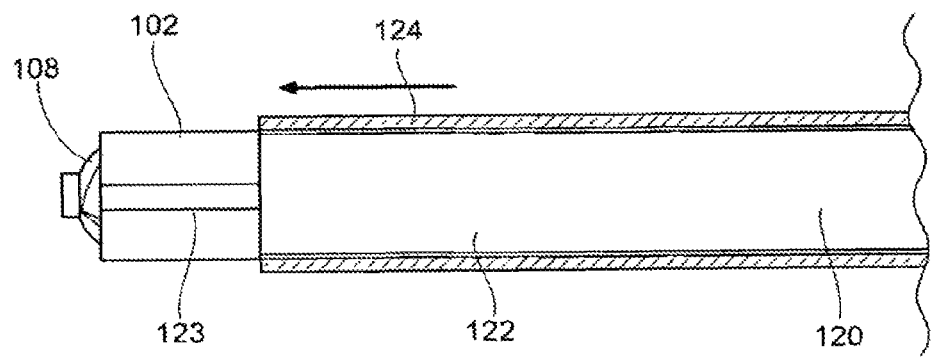
FIGS. 26A through 26C show side views of the flexible distal portion of the catheter having an adjustable flexible distal length, and also adapted for orbital rotation possibly using an element of unbalance.
Figure 26B:
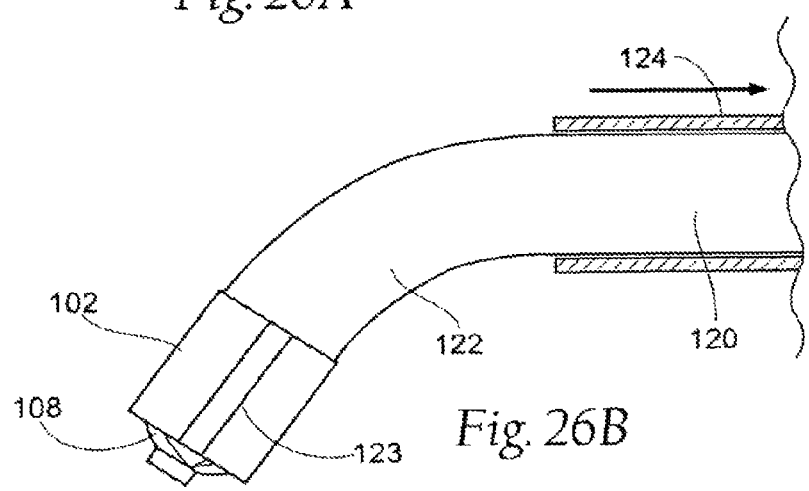

In an alternative embodiment, the rotating mechanism 150 may be powered by a controller that varies the speed and torque supplied to the catheter 120 and torque shaft 114 to optimize cutting efficiency or to automatically orbit the cutter 108 and/or cutting assembly 102 using variable speed with a fixed flexible distal length of the catheter 120, or providing further orbiting control by controlling the length of the distal flexible section 122 of the catheter 120). The length of the flexible distal portion 122 (or a predefined portion) may be controlled, i.e., adjusted by including a member 124 either inside or outside the catheter 120, or both inside and outside the catheter. The member 124 may comprise an axially adjustable sheath, wire, or guidewire, for example, the member 124 having a stiffness greater than the flexible distal portion. As seen in FIG. 26A, when the sheath 124 is advanced distally, its added stiffness reduces the flexibility of the flexible distal portion 122. When the sheath 124 is retracted proximally, the length of the flexible distal portion may be increased relative to the portion the sheath 124 was retracted (see FIG. 26B).

Figure 26C:
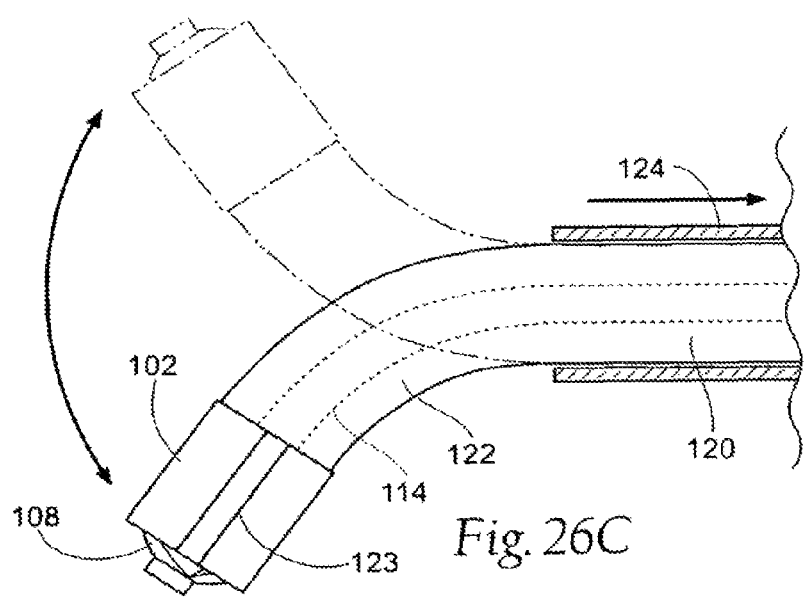

Orbit control may be induced or enhanced by providing an element of unbalance, i.e., an asymmetric cutter 108, housing 102, or counterweight 123, for example (see FIG. 26C). As the torque shaft 114 rotates the cutter 108, the asymmetric cutter (or housing) causes the cutter assembly 102 to rotate in an arcuate path, i.e., orbital path. The radius of this arcuate path may be increased by increasing the length of the adjustable flexible distal portion 122, and conversely, the arcuate rotational path may be reduced by decreasing the length of the adjustable flexible distal portion.

It is also possible to use feedback control to operate the system 100 in a vessel safe mode, so that the rate of cutting is decreased as the vessel wall is approached. This may be accomplished through speed control, or by reducing the degree to which the cutting blades penetrate above the housing window 106, 107 by retracting the cutter axially within the housing 104. Feedback variables could be by optical (infrared) or ultrasound transducer, or by other transducers (e.g., pressure, electrical impedance, etc.), or by monitoring rotational means 150 performance. Feedback variables may also be used, in safety algorithms to stop the cutter 108, for example, in a torque overload situation.

2. Catheter Chassis

Figure 27:
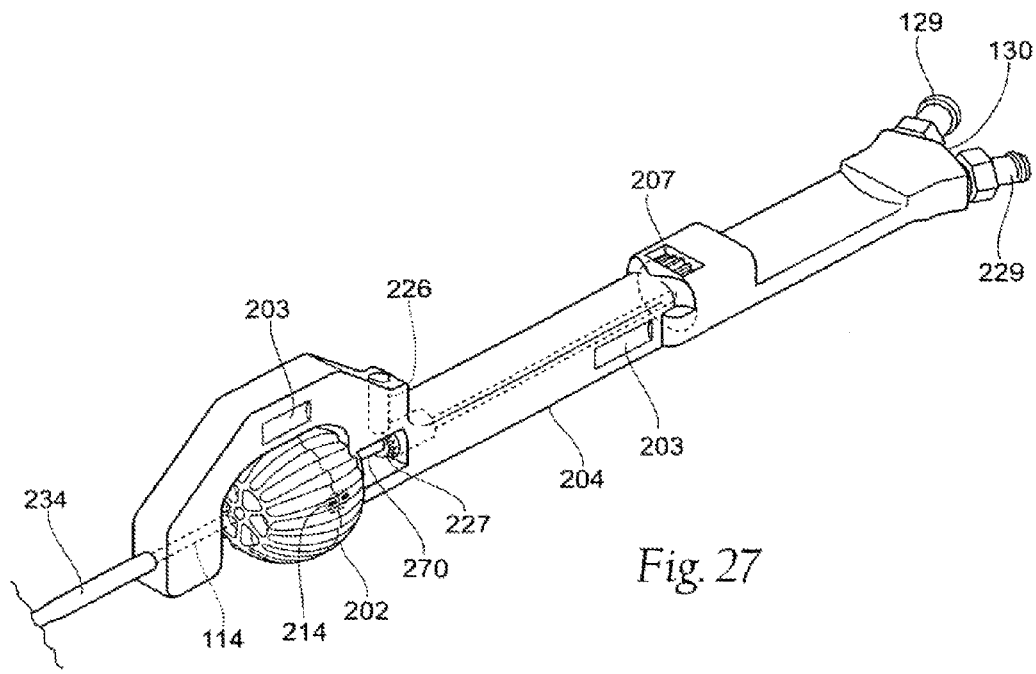
FIG. 27 is a perspective view of the catheter chassis portion adapted to snap fit within the handle base portion, and including the control mechanisms for steering and sweeping, irrigation, aspiration, and rotation of the torque shaft.

As can be seen in FIG. 27, the catheter chassis 204 provides an operational interface between the handle base 201 and the functions of the catheter 120 and cutting assembly 102. The catheter chassis 204 provides an extension of the catheter 120, including a strain relief 234 positioned at a distal end of the catheter chassis, and provides operational access to the catheter 120 for cutter assembly steering and sweeping (via the sweep control knob 202, a spring plunger 226, and an indexing cassette 227), cutter rotation (via the catheter chassis gear 207 and torque shaft 114), aspiration (via an aspiration port 229), irrigation (via a flush port 129), and a guidewire (via a guidewire lumen 130). A male port and a female port may be provided to identify the particular function. As can be seen in FIG. 27, coupling means 203 may also be also provided on the catheter chassis 204 to allow for tool free coupling between the handle base 201 and the catheter chassis 204.

a. Cutter Assembly Steering and Sweeping

Figures 28A, 28B:
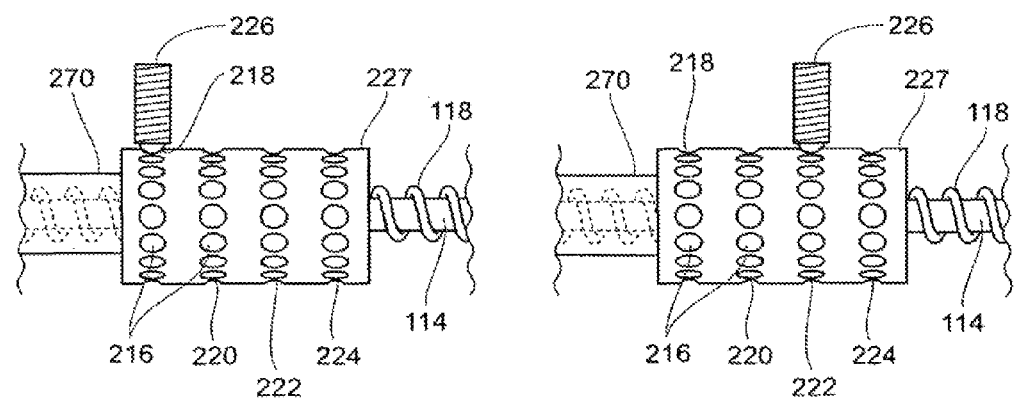
FIGS. 28A and 28B an indexing cassette and associated spring plunger, as seen in FIG. 27, the indexing cassette and associated spring plunger adapted for fine tune control for cutter assembly deflection and steering features.

FIGS. 27 through 28B show the sweep control knob 202, the spring plunger 226, and the indexing cassette 227, the combination of which allows for precise indexing (i.e., position control) of the cutting assembly 102. As shown, the sweep member 270 and torque shaft 114 extend through the sweep control knob 202 and the indexing cassette 227. The sweep control knob 202 and the indexing cassette 227 may be coupled to the sweep member 270, so when the sweep control knob 202 is rotated, both the sweep member 270 and the indexing cassette 227 rotate in unison, i.e., the angle of rotation of the sweep control knob 202 matches the angle of rotation of the sweep member 270 and the indexing cassette 227. It is to be appreciated that additional gearing may be included to adjust the speed of rotation for either or both of the sweep control knob 202 and the indexing cassette 227.

As seen in FIG. 28A, the indexing cassette 227 may include a plurality of indexing stops or divots 216. Although this variation of the indexing cassette 227 contains divots, other forms such as grooves or ridges, as non-limiting examples, may also serve an indexing purpose. The indexing stops 216 may have a twofold benefit. First, they allow incremental rotational indexing as the physician rotates the control knob 202. This incremental indexing is permitted due to the bending, torsion and axial strength characteristics of the system 100 permitting little or no misalignment between the distal and proximal ends of the system. A secondary advantage of the indexing stops 216 is that they allow incremental axial indexing as the physician advances the control knob 202 in an axial direction to bend or steer the distal portion 122 of the debulking catheter system 100 by moving the sweep member 270 in an axially distal direction.

As shown, any number of positions 218, 220, 222, 224 can be created on the indexing cassette 227. As shown in FIG. 28A, a spring plunger 226 can provide tactile feedback to the physician as the control knob 202 rotates. Once the physician desires to bend or steer the debulking system 100 by moving the knob 202 in an axial direction 228, the physician desirably may feel movement of the knob 202 (via the spring plunger 226) into the second 220 and third 222 stop positions (for example), as shown in FIG. 28B.

As shown, the control knob 202 may also include an orientation marker 214 that may correspond to the weakened section of the sweep frame 250 (not shown). The orientation marker 214 could also correspond to a side of the sweep frame 250 that is opposite to a spine 256 of the sweep frame. Because the orientation marker 214 may be aligned with the sweep frame in such a manner, the physician knows that the catheter 120 would bend in a direction corresponding to the orientation marker 214. This allows the physician to identify the orientation of the cutting assembly 102 as it sweeps within the body lumen by observing the orientation of the orientation marker 214 as the physician rotates the sweep control knob 202. Even if the one-to-one relationship may be lost, the indexing knob 202 adds a fine visual control to direct the distal portion 122 in defined steps or increments. This control can be useful because the physician can direct the cutter 108 within the immediate vicinity to work on areas that need to be resected, versus losing position due to excessive movement. An atherectomy or tissue debulking system having features that allow pushability as well as torsional strength allow the physician greater feedback and control when trying to steer the cutting assembly 102 towards a desired treatment site within the body.

As described above, the catheter chassis 204 includes a sweep control knob 202 coupled to the sweep member 270. The sweep control knob 202 can axially advance the sweep member 270 to cause deflection of the sweep frame 250 and distal portion 122 of the catheter 120. In addition, the sweep control knob 202 can rotate independently relative to the torque shaft 114 and rotatable cutter 108 in the cutting assembly 102.

Figure 29A:
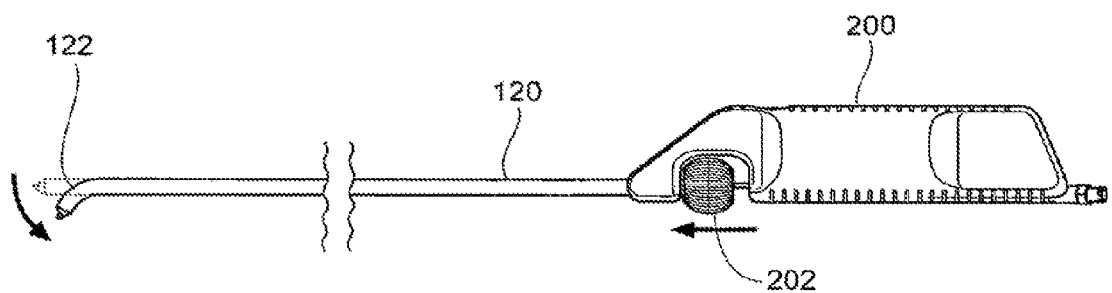
FIGS. 29A and 29B show a debulking system, including a control handle for the system, the handle adapted for rotating and articulating the distal portion of the catheter, including the cutter assembly.

As shown in FIG. 29A, distal movement of the sweep control knob 202 advances the sweep member 270 to deflect the catheter tip and cutting assembly 102. The degree of the deflection is controlled by the amount the sweep control knob 202 is advanced. The axial advancement of the sweep member 270 is limited by the maximum deflection of the sweep frame 250. To allow the cutter assembly 102 and distal portion 122 to be straight and undeflected, the sweep member 270 may be withdrawn proximally by the sweep control knob 202. This may cause removal of the axial force from the sweep frame 250 (in some variations, the sweep frame can be set in a straight configuration). In other variations, the sweep control knob 202 retracts the catheter body relative to the sweep frame 250 and/or member 270 to deflect the catheter tip and cutting assembly 102.

Figure 29B:
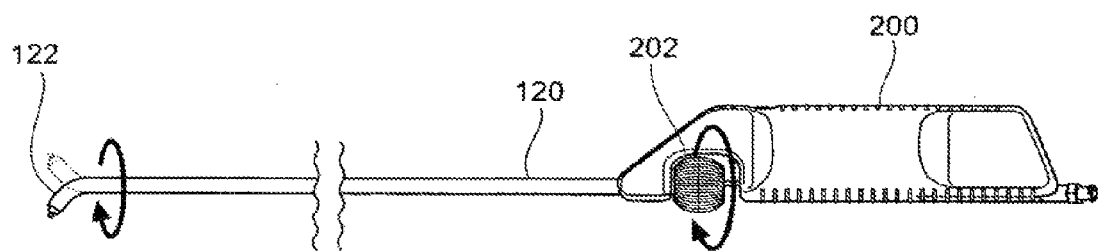

As shown in FIG. 29B, the sweep control knob 202 can be rotated to sweep the cutting assembly 102 in an arc manner. Although, sweeping of the cutting assembly 102 can also occur via manual operation, i.e., rotation of the handle 200. Variations of the handle 200 include sweep members 270 that can be selectively coupled to a sweep mechanism i.e., a sweep control motor (not shown), to activate an automated rotation. This may allow the physician to have a smooth, continuous, automated means to sweep the cutter assembly 102 without any manual effort.

The systems, devices, and methods of the present invention allow a physician to accurately determine the rotation of the cutting assembly 102 since the rotation of the cutting assembly closely corresponds to the rotation of the control knob 202. Such close correspondence is not available unless the catheter body 120 and/or sweep member 270 has sufficient bending, torsion and axial strength characteristics, as previously discussed. Accordingly, a further aspect of the system 100 occurs when these catheter bodies/sweep members are coupled to a handle 200 having a sweep control knob 202 that enables indexing and monitoring of the orientation of the cutter assembly 102. Clearly, this one-to-one relationship can be lost when the distal portion 122 or cutting assembly 102 encounters sufficient resistance against or within a lesion, occlusion, or diseased tissue. However, in such cases, the system 100 is still able to debulk tissue and perform its function even though the response may not be one-to-one. In any case, the ability to maintain a near one-to-one relationship and minimize rotational misalignment between the proximal and distal portions of the system 100 allows for steering of the debulking system 100 towards the treatment site.

b. Cutter Rotation and Aspiration

FIG. 30 shows the motor gear 206 adapted for rotation of the catheter chassis gear (torque shaft gear) 207, with the torque shaft 114 passing through and coupled to the torque shaft gear 207. A transfer propeller 212 may be rigidly attached to the torque shaft 114 to pump aspirated tissue debris 8 from the catheter 120 out into an attached aspiration reservoir. The torque shaft 114 may include one or more bearings 210. A seal 211 adjacent to the bearing 210 prevents aspirated tissue debris from leaking proximally through the bearing 210.

As previously described, the torque shaft 114 may have conveying members or helical grooves 118 on its outer diameter and/or within the central guidewire lumen 130. During a procedure run, a motor 150 drives the gear 206 to rotate. This causes rotation of the drive shaft 208, the transfer propeller 212, the torque shaft 114, and the cutter 108 all in the same rotational sense. Thus the cutter assembly 102 effectively cuts plague 8 and may further grind the plaque into smaller pieces, and then drives the debris 8 back into the helical groove 118 on the torque shaft 114. The rotating helical grooves 118 winds the debris back into the catheter chassis 204, and the debris is then transferred to an aspiration reservoir by the transfer propeller 212. The propeller 212 can take the form of a screw or a series of circumferentially arranged angled fan blades, for example. The cutter 108 may be rotated at speeds of ranging from about 8,000 rpm to about 25,000 rpm, although higher and lower speeds are within the scope of the invention. An alternative design would have the aspiration reservoir built into the catheter hub 204 and/or handle base 201.

The system 100 may also include a vacuum source or pump 152 to assist in evacuation of debris created by operation of the device. Any number of pumps or vacuum sources may be used in combination with the system. For example, a peristaltic pump may be used to drive materials from the system and into a waste container. FIG. 25A also shows the system 100 coupled to a fluid source 154. As with the rotating mechanism 150, the vacuum source and/or fluid source may be coupled to the system 100 e.g., at the handle 200, from inside or outside the surgical field.

c. Irrigation

FIG. 27 shows the catheter chassis 204 as having a flush port 129. The flush port 129 provides a means for injecting a fluid such as heparinized saline or any other medicine into the catheter body 120 and catheter chassis 204 to keep blood and tissue debris from clogging the space between components in the device. The flush port 129 can also help lubricate moving components within the catheter 120. One desirable fluid path is along the length of the catheter 120 in the space between the catheter body 120 and sweep member 270. Drugs or fluids can be introduced via the flush port 129 for flow out of one or more openings 131 near the distal portion 122 or cutting assembly 102. Drugs flushing out near the cutting assembly 102 can then infuse into the vessel wall. Using thrombus-inhibiting, stenosis-inhibiting, and/or anti-inflammatory drugs, for example, may help prevent restenosis after a thrombectomy or atherectomy procedure. Possible drugs may include rapamycin and analogs such as everolimus, biolimus, and sirolimus; M-prednisolone; interferon y-lb; leflunomide; mycophenolic acid; mizoribine; cyclosporine; tranilast; biorest; tacrolimus; taxius; clopidogrel; rapamycin; paclitaxel; botox; lydicane; Retin A Compound; glucosamine; chondroitin sulfate; or geldanamycin analogs 17-AAG or 17-DMAG, as non-limiting examples.

A wide range of other bioactive materials can be delivered by the system 100. Additional examples include heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin® or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, Taxol® or the derivatives thereof, or other anticancer chemotherapeutic agents; dexamethasone, dexamethansone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiopeptin (a growth hormone antagonist), angiogenin, a growth factor or an antigrowth factor antibody, or another growth factor antagonist; dopamine, bromocriptine mesylate, pergolide mesylate or another dopamine agonist; $^{60}$Co(5.3 year half life), $^{192}$Ir(73.8 days), $^{32}$P(14.3 days), $^{111}$In(68 hours), $^{90}$Y(64 hours), $^{99m}$Tc(6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol superoxide dismutase, deferoxamine, a 21-aminosteroid (lasaroid) or another free radical scavenger, iron chelator or antioxidant; a $^{14}$C—, $^{3}$H—, $^{131}$I—, $^{21}$P— or $^{36}$S- radiolabelled form or other radiolabelled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine betahydroxylase conjugated to saporin or other antibody targeted therapy agents; gene therapy agents; and enalapril and other prodrugs; Proscar®, Hytrin® or other agents for treating benign prostatic hyperplasia (BHP) or a mixture of any of these; and various forms of small intestine submucosa (SIS).

III. Additional System Features

A. Energy Delivery

The construction of the cutting assembly 102 can provide for additional modes of energy delivery. For example, when the system 100 excises tissue in vascularized regions excessive bleeding can occur (e.g., lung biopsy and excision). Accordingly, energy can be delivered to the target site via a conductive cutter assembly (i.e., the housing 104 and/or the cutter 108, for example). Sound energy (ultrasound), electrical energy (radio frequency current), or even microwaves can be used for this purpose. These energy sources delivered through the cutter assembly 102 can also be used to denature tissue (collagen), shrink tissue, or ablate tissue. Optionally, a guidewire, if used, may be removed and replaced with a cable for UV energy delivery and/or to deliver radiation treatments, all as a standalone or combination treatment.

B. Distal Portion Visualization

FIGS. 31A and 31B show variations of a sweep frame 250 having a visualisation feature 284 that permits a physician to determine orientation and direction of articulation of the cutting assembly 102 when the device is viewed under non-invasive imaging, e.g., fluoroscopy. FIG. 30A shows one variation of the visualisation feature 284 as being a notch or opening 284 on a side of the sweep frame 250 that is perpendicular to the direction in which the frame bends. In one example, the visualization mark is placed 90 degrees relative to the spine 256. Although the feature 284 is shown on the right side of the sweep frame 250, any side may be used so long as the location and orientation of the feature 284 conveys to the physician the orientation and direction of bend of the sweep frame 250 via non-invasive imaging.

FIG. 31B illustrates another variation of an orientation feature 284 comprising a marking substance (e.g., a radiopaque additive and/or a highly radiopaque metal deposited on the sweep frame 250, as non-limiting examples). In any case, the visualisation feature 284 must provide sufficient contrast against the frame 250 when viewed in a non-invasive imaging modality. These visualisation means may also include arrangements such as a notch, opening, tab, protrusion, or deposition, for example.

As shown, both visualization features 284 are on the right-hand side of the sweep frame 250 when the spine 256 of the frame 250 is directly adjacent to the physician. In this position, articulation of the sweep frame (that occurs in a direction away from the spine), causes the sweep frame 250 to deflect away from the physician. Accordingly, when the physician observes the visualization marks 284 to the right of the device, the physician will know that flexure of the sweep frame 250 will occur directly away from the physician. Clearly, the present invention includes any number of visualization features or placement of such features on any portion of the sweep frame 250 or other portions of the distal section 122, so long as the physician will be able to determine the orientation and direction of bend of the sweep frame 250 from viewing the visualisation mark(s) 284.

C. Flushing Solutions

Figure 32A:
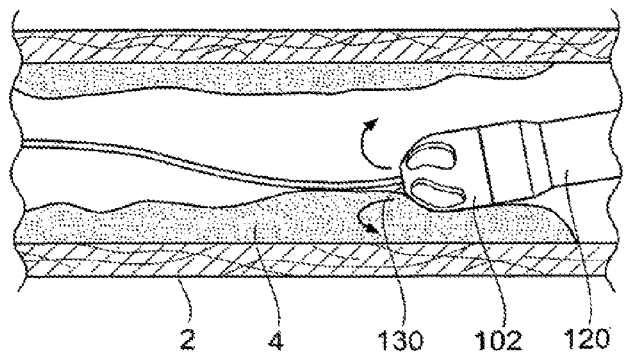
FIGS. 32A through 32C provide examples of fluid delivery systems.
Figure 32B:
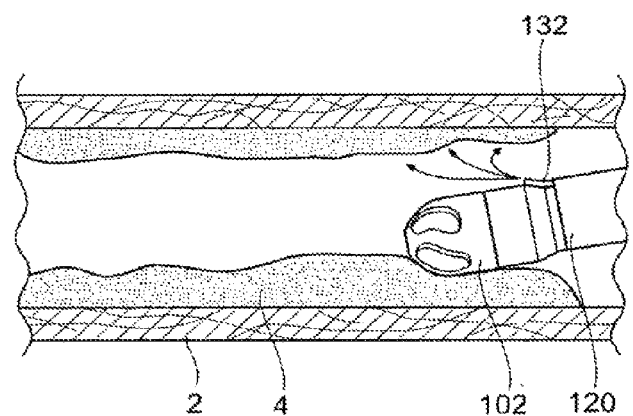
Figure 32C:
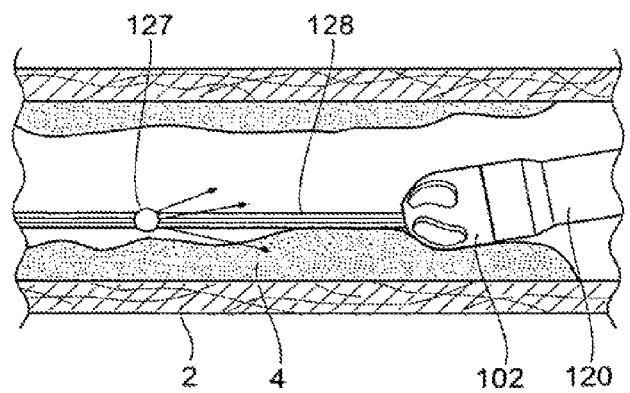

Infusing solutions (e.g., flushing) into the target treatment site may be desirable. Infused cool saline can prevent heating of blood and other tissue, which reduces the possibility of thrombus or other tissue damage. Heparinized saline can also prevent thrombus and thin out the blood to help maximize effectiveness of aspiration. The flush can also include thrombus-inhibiting, stenosis-inhibiting or anti-inflammatory drugs such as those listed above. This may help to prevent restenosis and may result in better long term patency. The flush may include paralytics or long-acting smooth muscle relaxants to prevent acute recoil of the vessel. FIGS. 32A to 32C illustrate variations of flushing out the system 100. The flush can be infused through the guidewire lumen 130 (FIG. 32A), a side lumen 132 in the catheter body 120 (FIG. 32B), and/or sideports 127 in the guidewire 128 (FIG. 32C).

Flush can come out of a port at the distal end of the cut tar 108 pointing the flush proximally to facilitate aspiration. Alternatively, by instilling the flush out the distal end of the cutter housing 104 over the rounded surface, the flow may be directed rearward by the Coanda effect. The restenosis-inhibitors can be carried by microcapsules with tissue adhesives or velcro-like features on the surface to stick to inner vessel surface so that the drug adheres to the treatment site, and to provide a time-release controlled by the resorption or dissolving of the coating to further improve efficacy. Such velcro-like features may be constructed with nanoscale structures made of organic or inorganic materials. Reducing the volume of foreign matter and exposing remaining tissue and extracellular matrix to drugs, stimulation, or sensors can make any of these techniques more effective.

Another way to infuse fluid is to supply pressurized fluid at the proximal portion of the guidewire lumen 130 (e.g., gravity and/or pressure feed with an intravenous bag, for example). A hemostatic seal with a side branch is useful for this purpose; tuohy-borst adapters are one example of a means to implement this.

Balancing the relative amount of infusion versus fluid volume aspirated allows control over the vessel diameter; aspirating more fluid than is instilled will evacuate the vessel, shrinking its diameter, and allow cutting of lesion at a greater diameter than the atherectomy catheter. This has been a problem for certain open cutter designs that use aspiration, because the aggressive aspiration required to trap the embolic particles evacuates and collapses the artery around the cutter blades. This is both a performance issue because the cutter can bog down from too high torque load, and the cutter can easily perforate the vessel. The cutter assembly 102 designs described herein obviates both problems, and further requires less aggressive aspiration to be effective, giving a wider range of control to the user.

D. Rapid Exchange

Figure 33:
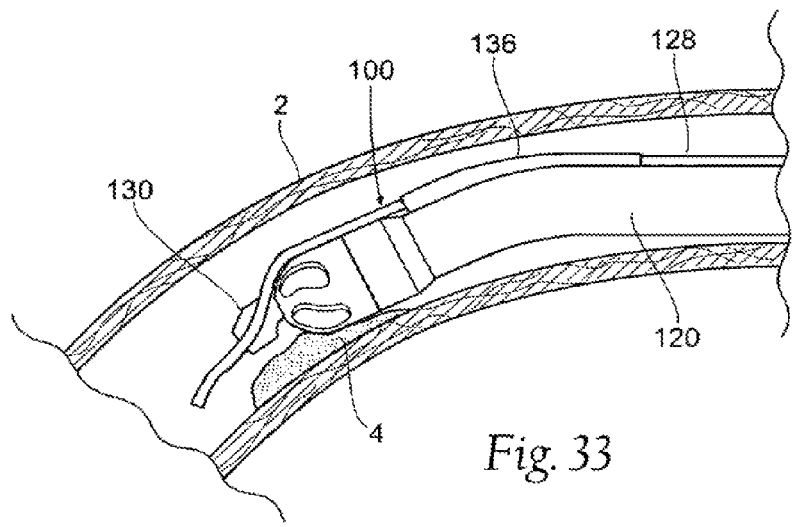
FIG. 33 shows a variation of a device configured for rapid exchange.

FIG. 33 illustrates a variation of a system 100 configured for rapid exchange. As shown, the system 100 includes a short passage, lumen, or other track 136 for the purpose of advancing the device 100 over the guidewire 128. However, the track 136 does not extend along the entire length of the catheter 120. Moreover, an additional portion of the track 136 may be located at a distal end 134 of the catheter 120 to center the guidewire 128.

This feature permits rapid decoupling of the system 100 and guidewire 128 by merely holding the guidewire still and pulling or pushing the system 100 over the guidewire. One benefit of such a feature is that the guidewire 128 may remain close to the procedure site while being decoupled from the system 100. Accordingly, the surgeon can advance additional devices over the guidewire 128 and to the site in a rapid fashion. This configuration allows for quick separation of the catheter 120 from the guidewire 128 and introduction of another catheter over the guidewire since most of the guidewire is outside of the catheter.

E. Over the Wire

Figure 34:
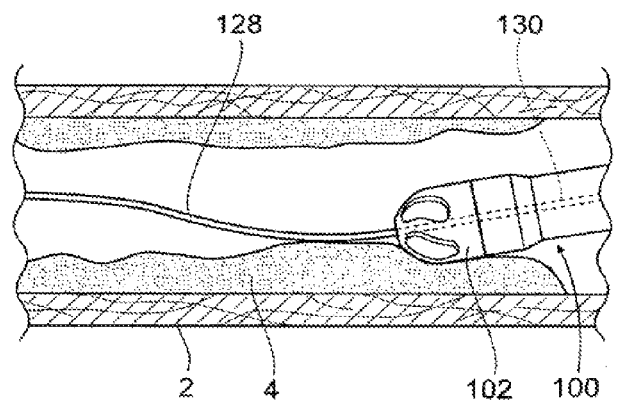
FIG. 34 illustrates an example of centering a tip of a cutting assembly over a guide wire.

As shown in FIG. 34, centering the tip of the cutting assembly 102 over the guide wire 128 improves the control, access and positioning of the cutting assembly 102 relative to a body lumen or vessel 2. To accomplish this, the cutting assembly 102 can have a central lumen 130 to accommodate a guide wire 128. Variations of the system 100 include a central guide wire lumen 130 that may run the length of the catheter 120 through all or some of the central components including the torque shaft 114, the cutter 108, and the handle 200. As noted above, the guidewire 128 can be affixed to the housing 104 or other non-rotational component of the cutting assembly 102. In such a case, the guidewire 128 may preferably be a short segment that assists with navigation of the device through an occluded portion of a body lumen. However, the system 100 can also operate without a guidewire since the distal portion 122 is steerable like a guidewire.

F. Combination Treatments

The devices, systems, and methods of the present invention may also be used in conjunction with other structures placed in the body lumens. For example, as shown in FIG. 35, one way to protect the vessel and also allow for maximum plaque volume reduction is to deploy a protective structure such as a stent, thin expandable coil or an expandable mesh 182 within a lesion. As this structure expands after deployment, the thin wire coil or the struts push radially outward through the plaque until it becomes substantially flush with the vessel wall. This expansion of thin members requires minimal displacement of plaque volume and minimizes barotrauma produced in balloon angioplasty or balloon expanded stent delivery. Once the protective structure 182 has expanded fully, atherectomy can be performed to cut away the plaque 4 inside the vessel 2 to open up the lumen. The vessel wall is protected by the expanded structure 182 because the structure members (coil or struts) resist cutting by the atherectomy cutter 108, and are disposed in a way that they cannot invaginate into the cutter housing 104 (and thereby be grabbed by the cutter 108). It is also possible to adjust the angle of the windows 106 on the guarded cutter housing 106 so that they do not align with the struts or coils. The adjustment to orientation may be accounted for in the coil or strut design, in the cutter housing design, or both.

Furthermore, the protective member 182 can be relatively flexible and have a low profile (i.e., thin elements), so that it may be left in place as a stent. Because the stent in this case relies mainly upon atherectomy to restore lumen patency, it may be designed to exert far less radial force as it is deployed. This allows usage of greater range of materials, some of which may not have as high of stiffness and strength such as bioresorbable polymers and metal alloys. Also, this allows a more resilient design, amenable to the mechanical forces in the peripheral arteries. It also minimizes flow disruption, to minimize hemodynamic complications such as thrombosis related to the relatively low flows found in the periphery. It is also possible to perform atherectomy prior to placing the protective structure 182, whether or not atherectomy is performed after placing the structure.

As described, it may be advantageous to couple atherectomy with stenting. By debulking the lesion, a lesser radial force is required to further open the artery and maintain lumen diameter. The amount of debulking can be tuned to perform well in concert with the mechanical characteristics of the selected stent 182. For stents that supply greater expansion and radial force, relatively less atherectomy is required for satisfactory result.

An alternative treatment approach is to debulk the lesion substantially, which will allow placement of a stent optimized for the mechanical conditions inherent in the peripheral anatomy. In essence, the stent can support itself against the vessel wall and supply mild radial force to preserve luminal patency. The stent may be bioresorbable, and/or drug eluting, with the resorption or elution happening over a period for days to up to 12 weeks or more, as a non-limiting example. A period of 4 to 12 weeks matches well with the time course of remodeling and return to stability as seen in the classic wound healing response, and in particular the known remodeling time course of arteries following stent procedures.

In addition, the stent geometry can be optimized to minimise thrombosis by inducing swirl in the blood flow. This has the effect of minimizing or eliminating stagnant or recirculating flow that leads to thrombus formation. Spiral construction of at least the proximal (upstream) portion of the stent 182 may achieve this. It may also be beneficial to ensure that flow immediately distal to the stent does not create any stagnant or recirculation zones, and swirl is a way to prevent this as well.

It is also possible to use the devices, systems, and methods described herein to restore patency to arterial lesions by debulking in-stent restenosis. FIG. 35 shows the system 100 removing lesions within a stent or coil.

Figure 40A:
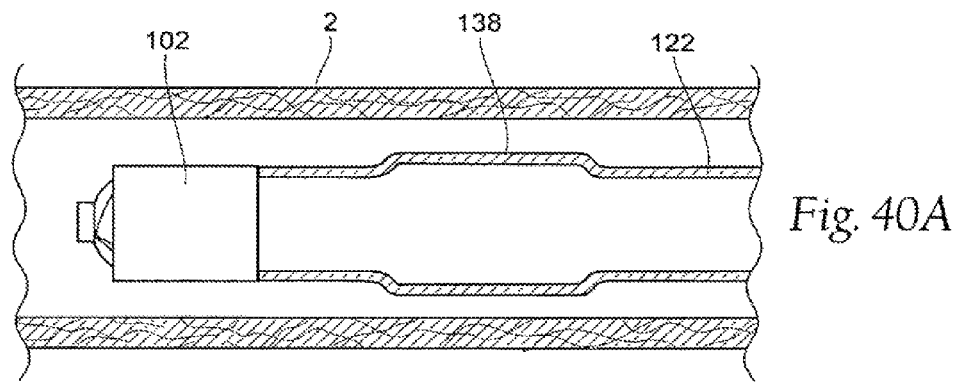
FIGS. 40A and 40B show a distal portion of a debulking catheter including a balloon or other mechanism for adjunctive angioplasty, stent, and/or other drug delivery.
Figure 40B:
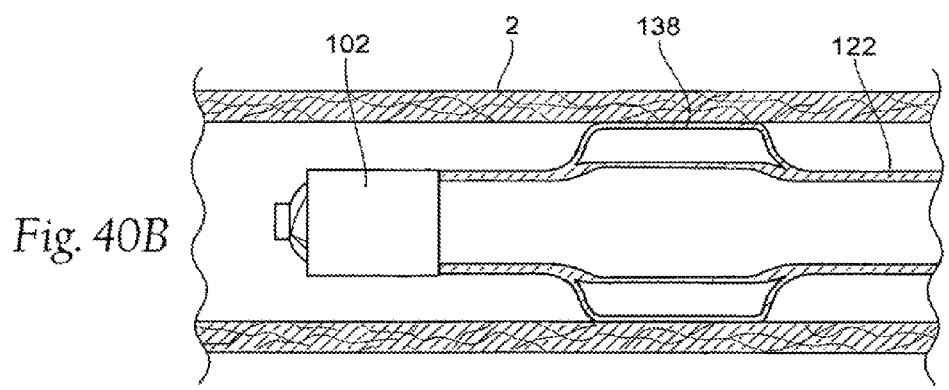

The system 100 may be further configured with a balloon 138 or other mechanism proximal to the cutter, for adjunctive angioplasty, stent, and/or drug delivery (see FIGS. 40A and 40B for example). In combination, the system 100 may first debulk a vessel with the mechanism 138 undeployed (see FIG. 40A), and then deploy a mechanism, such as drug coated balloon 138, because the balloon drug delivery may be more uniform and effective drug delivery compared to drug delivery within an untrimmed vessel (see FIG. 40B). The system 100 may also deliver drug therapy through the guidewire lumen 130. For example, a fluid may be delivered through the lumen, and with the cutting assembly 102 steered toward plaque and/or a wall of the vessel, a jet of drug therapy may be delivered to the target site.

The system 100 may optionally be configured to deliver self-expanding stents. This feature provides convenience to the user and greater assurance of adjunctive therapy at the intended location where atherectomy was performed.

G. Additional System Features

Figure 41A:
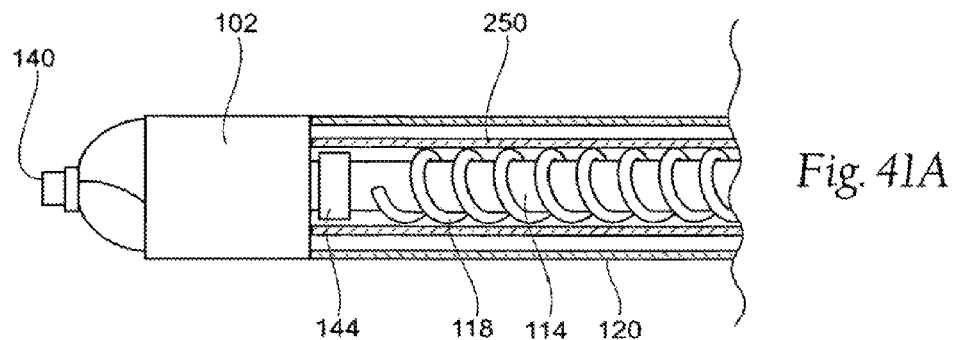
FIGS. 41A and 41B are side views of an embodiment of a debulking system, the system including a transducer and/or sensor to provide imaging of the targeted treatment site before and/or after treatment.
Figure 41B:
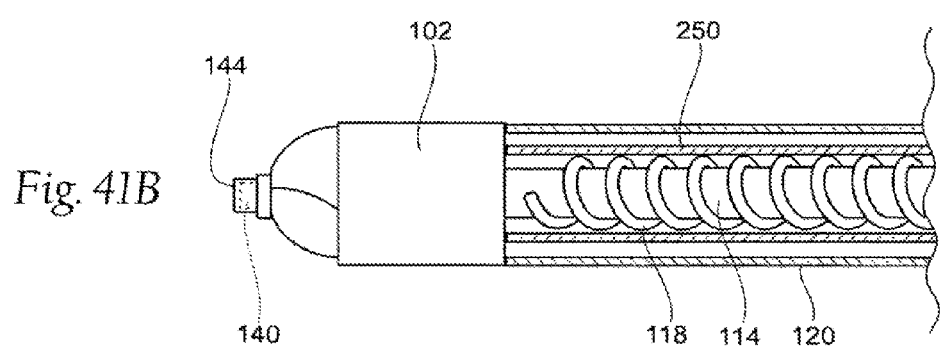

Additional components may be incorporated into the devices, systems, and methods described herein. For example, it can be desirable to incorporate sensors and/or transducers 144 into and/or onto the distal portion 122 of the catheter body 120 and/or the cutting assembly 102 to characterize the plague and/or to assess plague and wall thickness and vessel diameter for treatment planning (see FIGS. 41A and 41B). Transducers 144 may also be desired to indicate the progression of debulking or proximity of the cutter 108 to a vessel wall. For example, pressure sensors 144 mounted on the catheter housing 104 or cutter 108 can sense the increase in contact force encountered in the event that the housing is pressed against the vessel wall. Temperature sensors 144 can be used to detect vulnerable plaque. Ultrasound transducers 144 can be used to image luminal area, plaque thickness or volume, and wall thickness. Electrodes 144 can be used for sensing the impedance of contacted tissue, which allows discrimination between types of plaque and also vessel wall. Electrodes can also be used to deliver impulses of energy, for example to assess innervation, to either stimulate or inactivate smooth muscle, or to characterize the plaque (composition, thickness, etc.). For example, transient spasm may be introduced to bring the vessel to a smaller diameter making it easier to debulk, then reversed either electrically or pharmaceutically. Electrical energy may also be delivered to improve the delivery of drugs or biologic agents, by causing the cell membrane to open in response to the electric stimulation (electroporation). One method of characterization by electrical measurement is electrical impedance tomography.

Figure 42:
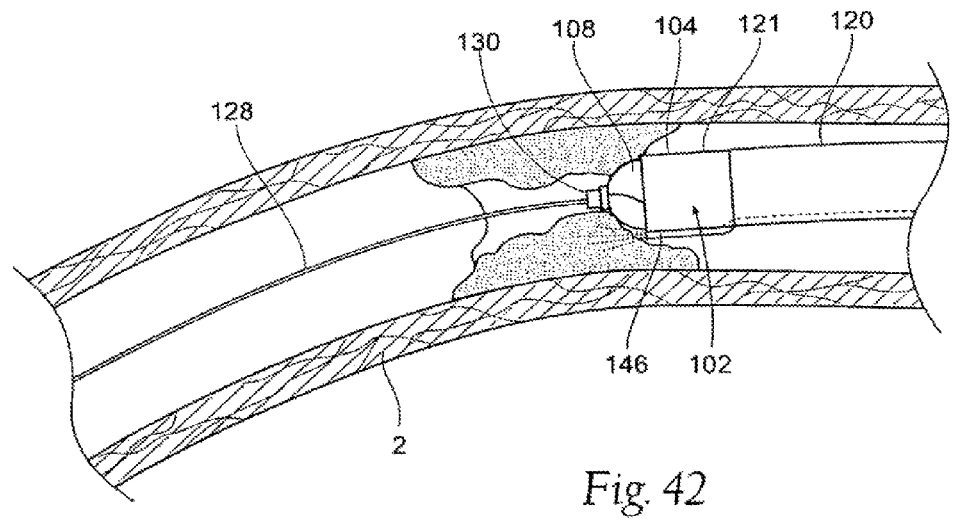
FIG. 42 is a side view of an embodiment of a debulking system, the system including an imaging system at or near a distal end to provide imaging of the targeted treatment site before and/or after treatment.

Optical coherence tomography (OCT) can be used to make plaque and wail thickness measurements. As seen in FIG. 42, an OCT device 146 may be provided in conjunction with the cutter assembly 102, for example. The OCT device 146 may also be introduced into the target area through the guidewire lumen 130. The steerable distal portion 122 allows for controlled viewing of not only the center portions of the vessel, but the sidewalls can be imaged as well. The forward cutting assembly 102 combined with the OCT device 146 allows for imaging of the targeted treatment area before, during, and after debulking the vessel. A simple saline flush may be used to reduce absorption of the optical waves in the blood, to improve imaging of the viewing area.

IV. Lower Extremity Anatomy

Figure 36:
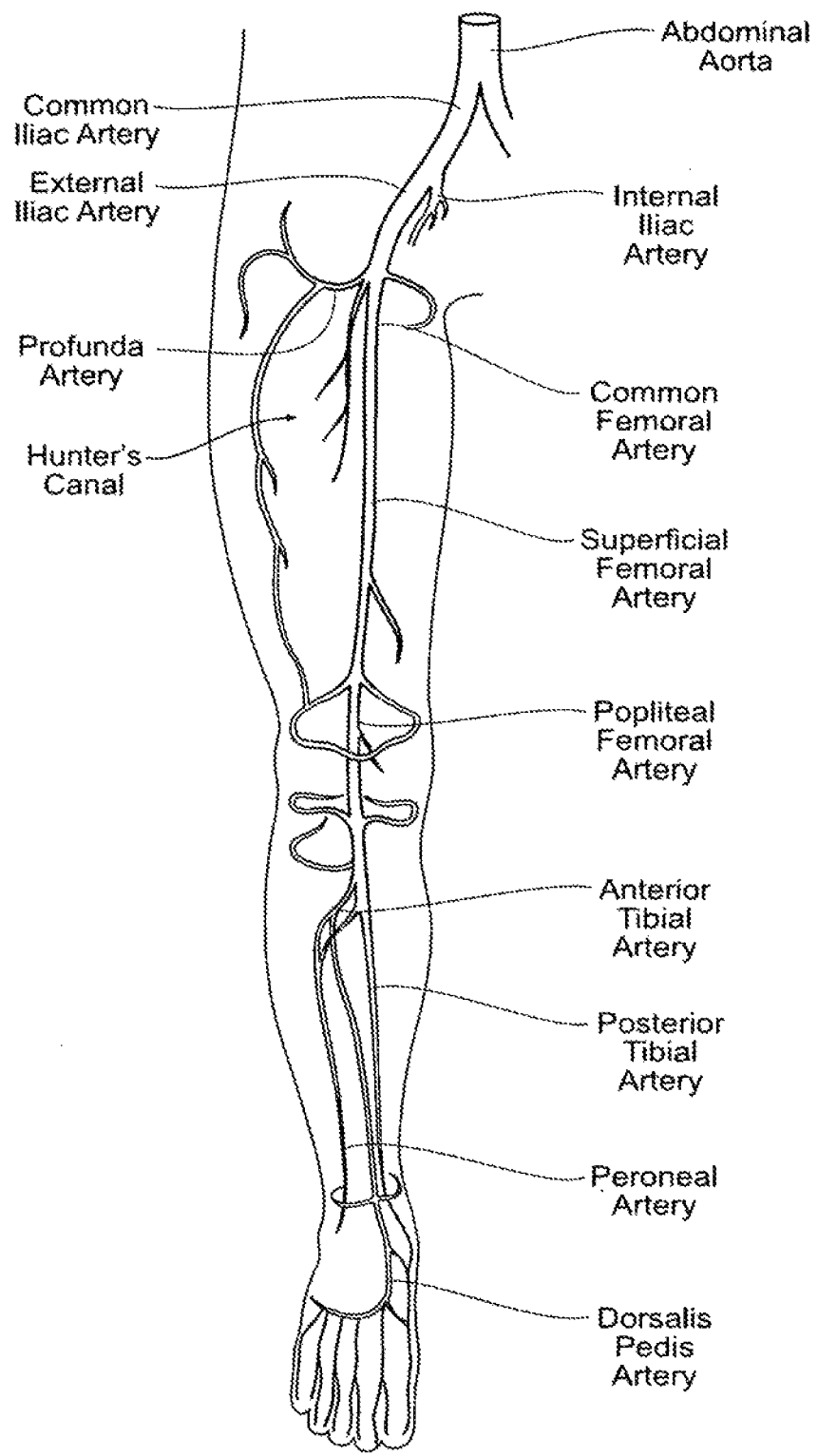
FIG. 36 shows an anatomic view of the lower limb of an animal, including a human, and showing a representation of the arteries within the lower limbs.

FIG. 36 shows the arteries of the pelvis and the lower limbs. As previously described, the devices, systems, and methods are well suited for use in this peripheral region. The main artery extending from the pelvis is the iliac artery, with the internal iliac artery supplying most of the blood to the pelvic viscera and wall.

The external iliac arteries diverge through the greater (false) pelvis and enter the thighs to become the right and left femoral arteries. Both femoral arteries send branches superiorly to the genitals and the wail of the abdomen. The profunda femoris artery (also known as the deep femoral artery) branches off of the proximal superficial femoral artery soon after its origin. The profunda travels down the thigh closer to the femur than the femoral artery, running between the pectineus and the adductor longus muscles.

The femoral passes through the hunter's canal and continues down the medial and posterior side of the thigh posterior to the knee joint, a very flexible region, where it becomes the popliteal artery. Between the knee and ankle, the popliteal runs down on the posterior aspect of the leg and is called the posterior tibial artery. Inferior to the knee, the peroneal artery branches off the posterior tibial to supply structures on the medial side of the fibula and calcaneus bones (both not shown). In the calf, the anterior tibial artery branches off the popliteal and runs along the anterior surface of the leg. At the ankle it becomes the dorsalis pedis artery. At the ankle, the posterior tibial divides into the medial and lateral plantar arteries. The lateral plantar artery and the dorsalis pedis artery unite to form the plantar arch. From this arch, digital arteries supply the toes.

A. Representative Uses of the Atherectomy System

The debulking system 100 as described makes possible a single insertion of the catheter 120 for providing treatment of occluded body lumens, including the removal of lesions from arteries in the lower extremity, the single insertion of the catheter 120 including removal of the debulked material. The debulking system 100 is adapted to perform debulking in a wide range of vessels, including arteries in the upper and lower extremity, representative examples of which will be described for the purpose of illustration.

The system 100 may be used in a wide range of artery configurations found in the leg, including tortuous and straight, and may be used in short and long vessels, i.e., 20 cm or longer. The system 100 is well suited for use above the knee up to the common femoral artery, although it is to he appreciated that the system may be used in arteries proximal to the common femoral artery. The system is also well suited for use in arteries below the knee, and may be used all the way down to the ankle and/or foot.

A wide range of vessel sizes may be found in the leg, all of which may be accessible for use with the system 100. A typical diameter for the catheter 120 ranges from about 1.0 mm to about 3.0 mm, providing access for a wide range of target sites. For example, the common femoral artery ranges in diameter between about 6 mm to about 7 mm; the superficial femoral artery ranges between about 4 mm to about 7 mm; the popliteal artery ranges between about 3 mm to about 5 mm; and the tibial artery ranges between about 2 mm to about 4 mm.

The profunda and the common femoral arteries have been found to be less than desirable areas for stenting and/or ballooning, for example, because this area should remain available for bypass graft of the femoral artery. The devices, systems, and methods for atherectomy in these regions provide a good solution for debulking.

A variety of options exists for access to target sites within the leg. Based on access and desired target area, a variety of possible working lengths exist for the system 100. For example, four size options may be available: 1) ipsilateral (same side) access and down to a site above the knee; 2)

ipsilateral access and down to a site below the knee; 3) contralateral (opposite side) access and across and down to a site above the knee; and 4) contralateral access and across and down to a site below the knee. The size options take into account access from various anatomical access points such as femoral artery, brachial artery, etc.

Figures 37A, 37B:
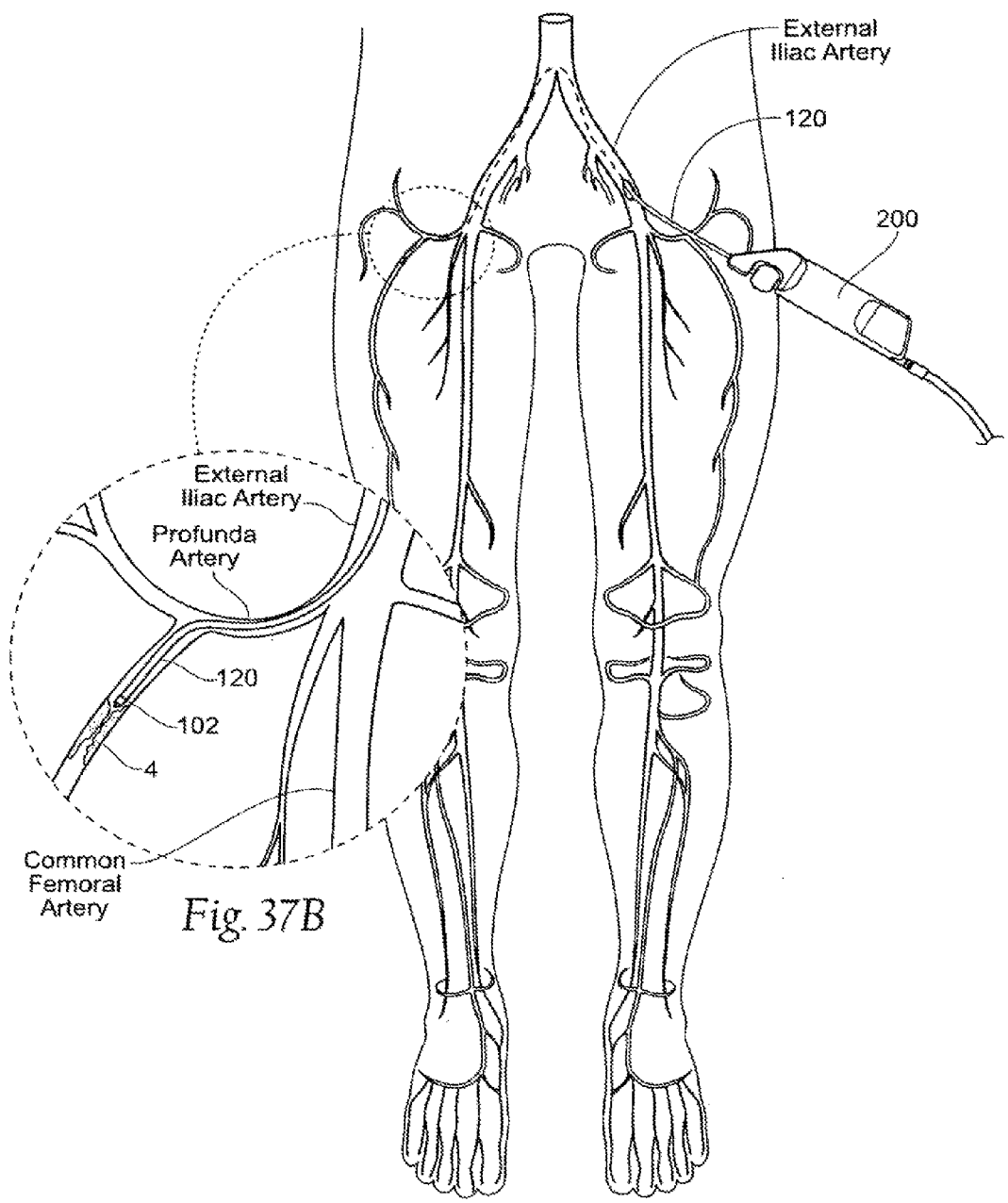
FIG. 37A shows an anatomic view similar to FIG. 36, and showing a contralateral configuration for a possible access site for the system to be used in the vasculature for the removal of lesions.
FIG. 37B shows a detail view of FIG. 37A, the detail view showing the catheter 120 extending through the external iliac artery, through tortuous vessels, and into the profunda artery for debulking of an occlusion.
Figures 38A, 38B:
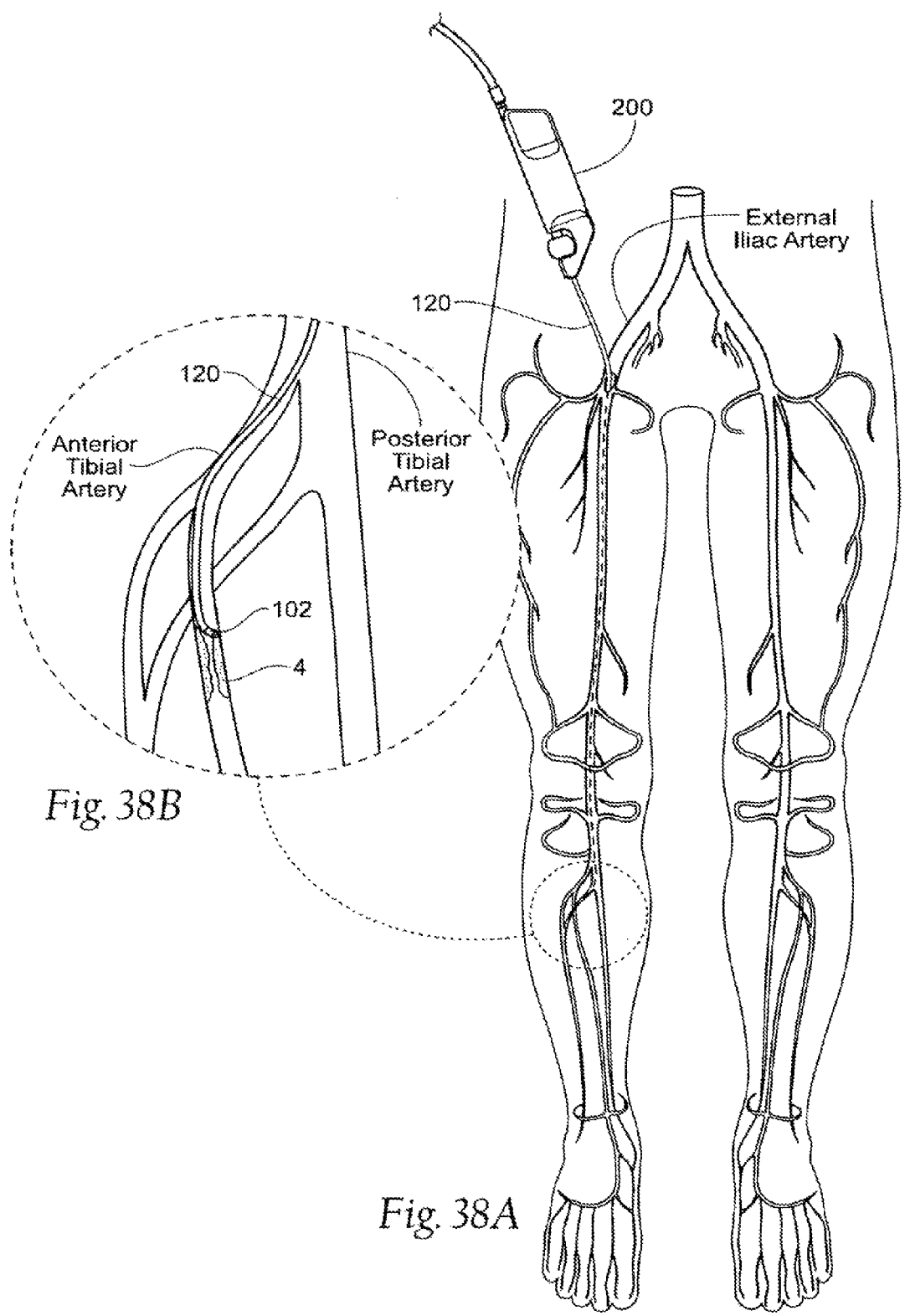
FIG. 38A shows an anatomic view similar to FIG. 35, and showing an additional possible ipsilateral access site for the system to be used in the vasculature for the removal of lesions.
FIG. 38B shows a detail view of FIG. 38A, the detail view showing the catheter 120 extending through the popliteal femoral artery, through tortuous vessels, and into the anterior tibial artery for debulking of an occlusion.

A typical working length of the system 100 ranges from about 110 cm to about 130 cm for ipsilateral approaches (see FIG. 37), and from about 130 cm to about 150 cm for contralateral approaches (see FIG. 38) possibly extending below the knee. Contralateral access may be desired and/or necessary because the introducer may be blocking the treatment area.

V. Instructions for Use of the System

The instructions for use 404 can direct use of the catheter-based system 100 via a peripheral intravascular access site, such as in the femoral artery, optionally with the assistance of image guidance. Image guidance includes but is not limited to fluoroscopy, ultrasound, magnetic resonance, computed tomography, optical coherence tomography, or combinations thereof.

The system 100 may be used in a procedure that takes less time than prior debulking devices, e.g., a debulking procedure may be performed in 45 minutes or less. In addition, only a single insertion of the system 100 is needed for a procedure (i.e., no catheter exchange), as compared to requiring multiple catheter exchanges for prior debulking devices. This is because the system 100 is adapted to "sweep" the lumen of materials, the sweep feature allowing the single system 100 to create a passage in the lumen having a ratio ranging from about one to up to about four times the diameter of the catheter 120. The system is adapted to debulk vessels ranging in diameter from about one mm to about ten mm, although smaller and larger diameter vessels are within the scope of the invention.

Prior to use, a clinician identifies the particular vascular region to which a prescribed treatment using the atherectomy system 100 will be applied. The site is prepped for vascular access to the artery to be treated. The debulking system 100 may be removed from the sterile package. The distal portion 122 of the system 100 is inserted into the artery and advanced to the target site. A guidewire may also be used during this phase of the procedure. The steering capabilities of the system 100 may be used to assist the surgeon to steer the system through tortuous vessels to the target site. Once the cutting assembly is at the target site, the surgeon powers the system 100 by pressing or activating the on/off means 234. The surgeon is able to control the operation of the system 100 with only one hand on the ergonomic handle 200. With the cutter 108 rotating at a desired RPM, under image guidance, the surgeon slowly advances the catheter 120 distally to cut and remove plaque. The surgeon is able to use the sweeping capabilities of the system 100 to create a sweeping motion of the cutting assembly 102 to sweep and cut the lesion in an arcing path, thereby producing a diameter clearing in the vessel that may be up to four times the diameter of the catheter 120. As the cutting is taking place, system first cuts the material with the first cutting edge 112, and then further cuts or grinds the cut material into smaller pieces for easier transportation through the length of the catheter 120, through the catheter chassis 204, and out the aspiration port 209 to a container.

Depending on the desired treatment, the system 100 may be used for combination treatments as previously described. For example, the guidewire, if used, may be removed and replace with additional treatment options, such as UV radiation. Or, the flushing system as previously described may be used to infuse drugs into the target site, possibly before, during, or after the debulking procedure.

After the lesion has been removed from the vessel, the surgeon powers down the system, and slowly withdraws the catheter from the vessel. The entry location is cleaned and bandaged. The system 100 may be disposed of per hospital or facility guidelines.

Additional or alternative instructions may describe various procedures and uses of the system. For example, the instructions for use may describe the use of the catheter, the instructions comprising the operations of introducing the catheter assembly into the blood vessel and positioning the tissue cutting assembly at our near a site in need of tissue debulking, manipulating the tissue removal assembly to debulk tissue in the blood vessel, creating a cleared tissue diameter within the vessel of at least two times the diameter of the tissue removal assembly, and removing the cleared tissue.

Instructions for use describing the use of the catheter may also comprise the operations of introducing the catheter assembly into the blood vessel and positioning the tissue cutting assembly at or near a site in need of tissue debulking, manipulating the deflection control device thereby deflecting a distal portion of the catheter, and manipulating the rotation control device thereby rotating the distal portion of the catheter in an arcuate path.

Additional instructions for use describing the operation of the catheter may comprise introducing the catheter assembly into the blood vessel and positioning the tissue cutting assembly at or near a site in need of tissue debulking, deflecting the bending frame in a direction of a first radial side of the bending frame by moving a sweep member at or near the proximal end of the catheter, thereby causing the tissue cutting assembly to deflect in the direction of the first radial side, rotating a torque shaft extending through the catheter and coupled to at least the rotatable cutter, moving the sweep member independently of the torque shaft for rotating the bending frame and causing the tissue cutting assembly to sweep in an arcuate path relative to an axis of a proximal end of the bending frame, and removing the occlusive material.

Additional instructions for use describing the operation of the catheter may comprise providing a catheter sized and configured to be introduced into the blood vessel, the catheter including a tissue cutting assembly at or near a distal end of the catheter, the tissue cutting assembly including a rotatable cutter for debulking the tissue from the blood vessel, providing a control handle coupled to the catheter assembly, the control handle including steering means for steering the tissue cutting assembly, introducing the catheter into an iliac artery, advancing the catheter into a femoral artery, a profunda femoris artery, an artery in the hunter's canal, a popliteal artery, a tibial artery, a peroneal artery, a dorsalis pedis artery, a medial plantar artery, a lateral plantar artery, or a digital artery, positioning the tissue cutting assembly at or near a target site in the femoral artery, the profunda femoris artery, the artery in the hunter's canal, the popliteal artery, the tibial artery, the peroneal artery, the dorsalis pedis artery, the medial plantar artery, the lateral plantar artery, or the digital artery, operating the steering means by applying a first force to the steering means, the first force causing the distal portion of the catheter to deflect in a radial direction, operating the steering means by applying a second force to the steering means, the second force causing the distal portion of the catheter to rotate in an arcuate path while the distal portion is deflected in the radial direction, advancing the catheter distally to sweep the target site thereby allowing the rotatable cutter to debulk tissue from the target site in the arcuate path, and removing the debulked tissue from the target site, thereby treating the blood vessel.

VI. System Kit

Figure 39:
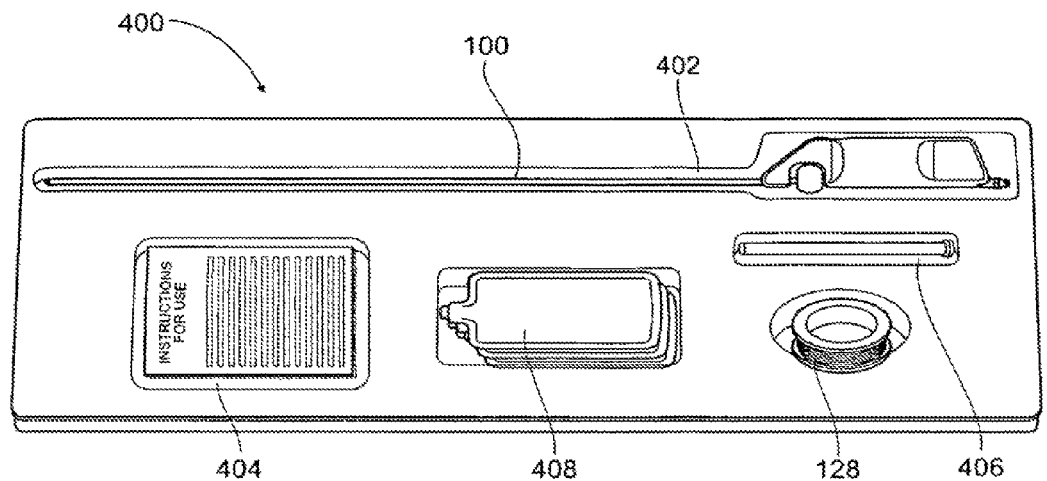
FIG. 39 is a view of a set of components of the system consolidated for use in a multiple piece kit, along with instructions for their use.

As FIG. 39 shows, the system 100 and devices as just described can be consolidated for use in a multiple piece functional kit 400. It is to be appreciated that the system 100 and devices are not necessarily shown to scale.

The kit 400 can take various forms. In the illustrated embodiment, the kit 400 comprises an individual package comprising a sterile, wrapped, peel-open assembly. The kit 400 may include an interior tray 402 made, e.g., from die cut cardboard, plastic sheet, or thermo-formed plastic material, which hold the contents. The kit 400 also preferably includes instructions or directions 404 for using the contents of the kit 400 to carry out a desired procedure, as described above.

The kit 400 provides the main components of the debulking system 100 as described, including the cutting assembly 102, the catheter 120, and the handle 200, assembled and ready for use. In one embodiment the handle base 201 may not be coupled to the catheter chassis 204. The remaining components may be optional ancillary components used in the deployment of the system 100, e.g., a conventional vascular access sheath 406; a conventional (e.g., 0.014 inch) guide wire 128; and bags containing heparinized saline for catheter flushing and contrast for angiography 408.

The instructions for use 404 can, of course vary. The instructions for use 404 can be physically present in the kit, but can also be supplied separately. The instructions for use 404 can be embodied in separate instruction manuals, or in video or audio recordings. The instructions for use 404 can also be available through an internet web page.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of treating a region of a blood vessel comprising:
   identifying a first arterial site at or below the knee having occlusive material forming a lesion;
   introducing a distal end of a catheter at an access site above the knee, wherein the catheter comprises a cutting assembly at the distal end of the catheter and a slotted tube comprising a first slot pattern in a proximal portion of the catheter and a second slot pattern in a distal portion of the catheter, the cutting assembly comprising:
   a distal cutter with one or more fluted cutting edges;
   a cutting core adapter having a number of fluted cutting edges greater than that of the distal cutter; and
   a housing comprising a forward cutting surface, wherein the cutter is located concentrically within the housing;
   advancing the cutting assembly to the first arterial site;
   rotating the distal cutter of the cutting assembly to remove occlusive material from the lesion;
   cutting or grinding the occlusive material into smaller pieces using the cutter core adapter; and
   removing the occlusive material through an aspiration port.

2. The method of claim 1 wherein the catheter comprises a torque shaft, wherein the torque shaft is connected to the cutting assembly.

3. The method of claim 2 wherein the catheter comprises a lumen extending through the torque shaft and the cutting assembly accommodating passage of a guide wire.

4. The method of claim 2 wherein the torque shaft has at least one helical conveyor member wound about an exterior such that rotation of the torque shaft conveys material across a length of the torque shaft.

5. The method of claim 1 wherein introducing the distal end of the catheter comprises advancing the distal end over a guide wire.

6. The method of claim 1 wherein the catheter further comprises a burr located on a distal tip of the cutter.

* * * * *